(12) United States Patent
Youngman et al.

(10) Patent No.: US 7,589,204 B2
(45) Date of Patent: Sep. 15, 2009

(54) INDANE COMPOUNDS AS CCR5 ANTAGONISTS

(75) Inventors: Michael Youngman, Durham, NC (US); Wieslaw Mieczyslaw Kazmierski, Durham, NC (US); Hanbiao Yang, Standord, CA (US); Christopher Joseph Aquino, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 12/416,178

(22) Filed: Apr. 1, 2009

(65) Prior Publication Data

US 2009/0187021 A1  Jul. 23, 2009

Related U.S. Application Data

(62) Division of application No. 10/538,183, filed as application No. PCT/US03/39975 on Dec. 12, 2003, now Pat. No. 7,531,661.

(60) Provisional application No. 60/433,378, filed on Dec. 13, 2002.

(51) Int. Cl.
*C07D 471/10* (2006.01)
*C07D 211/58* (2006.01)

(52) U.S. Cl. .................. 546/20; 546/205; 546/199; 546/194

(58) Field of Classification Search .................. 546/20, 546/194, 199, 205
See application file for complete search history.

(56) References Cited

U.S. PATENT DOCUMENTS 6,096,780 A  8/2000  Shiraishi et al.

FOREIGN PATENT DOCUMENTS

WO  WO 2004/009584  1/2004

*Primary Examiner*—Charanjit S Aulakh
(74) *Attorney, Agent, or Firm*—Bonnie L. Deppenbrock

(57) ABSTRACT

The present invention relates to compounds of formula (I), or pharmaceutically acceptable derivatives thereof, useful in the treatment of CCR5-related diseases and disorders, for example, useful in the inhibition of HIV replication, the prevention or treatment of an HIV infection, and in the treatment of the resulting acquired immune deficiency syndrome (AIDS).

1 Claim, No Drawings

INDANE COMPOUNDS AS CCR5 ANTAGONISTS

This application is a divisional of U.S. Ser. No. 10/538,183 filed on Jun. 9, 2005, now U.S. Pat. No. 7,531,661 which was filed pursuant to 35 U.S.C. §371 as a United States National Phase Application of International Application No. PCT/US2003/039975 filed Dec. 12, 2003, which claims priority from 60/433,378 filed Dec. 13, 2002.

BACKGROUND OF THE INVENTION

The human immunodeficiency virus ("HIV") is the causative agent for acquired immunodeficiency syndrome ("AIDS"), a disease characterized by the destruction of the immune system, particularly of CD4+ T-cells, with attendant susceptibility to opportunistic infections, and its precursor AIDS-related complex ("ARC"), a syndrome characterized by symptoms such as persistent generalized lymphadenopathy, fever and weight loss.

In addition to CD4, HIV requires a co-receptor for entry into target cells. The chemokine receptors function together with CD4 as co-receptors for HIV. The chemokine receptors CXCR4 and CCR5 have been identified as the main co-receptors for HIV-1. CCR5 acts as a major co-receptor for fusion and entry of macrophage-tropic HIV into host cells. These chemokine receptors are thought to play an essential role in the establishment and dissemination of an HIV infection. Therefore, CCR5 antagonists are thought to be useful as therapeutic agents active against HIV.

We have now discovered a series of small molecule non-peptide compounds that are useful as inhibitors of HIV replication.

BRIEF DESCRIPTION OF THE INVENTION

The present invention features compounds that are useful in the inhibition of HIV replication, the prevention of infection by HIV, the treatment of infection by HIV and in the treatment of AIDS and/or ARC, either as pharmaceutically acceptable salts or pharmaceutical composition ingredients. The present invention further features methods of treating AIDS, methods of preventing infection by HIV, and methods of treating infection by HIV as monotherapy or in combination with other antivirals anti-infectives, immunomodulators, antibiotics or vaccines. The present invention also features pharmaceutical compositions, comprising the above-mentioned compounds that are suitable for the prevention or treatment of CCR5-related diseases and conditions. The present invention further features processes for making the above-mentioned compounds.

SUMMARY OF THE INVENTION

The present invention includes compounds of formula (I)

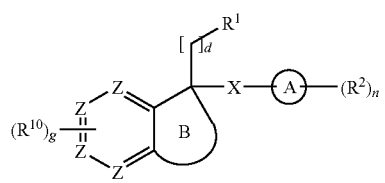

or pharmaceutically acceptable derivatives thereof, wherein:

X is a $C_{1-5}$ alkylene chain, wherein said X is optionally substituted by one or more =O, =S, —S(O)$_r$—, alkyl or halogen and wherein said $C_{1-5}$ alkylene chain may optionally have 0-3 heteroatoms selected from oxygen, phosphorus, sulfur, or nitrogen;

Ring A is a saturated, partially saturated, or aromatic 3-7 monocyclic or 8-10 membered bicyclic ring having one ring nitrogen and 0-4 additional heteroatoms selected from oxygen, phosphorus, sulfur, or nitrogen;

Ring B is a 4-7 membered saturated, partially saturated, or aromatic carbocyclic ring optionally containing one or two heteroatoms selected from oxygen, phosphorus, sulfur, or nitrogen; each Z may be carbon or nitrogen, provided that at least one Z is carbon;

$R^1$ is selected from the group consisting of (a) a saturated, partially saturated, or aromatic 4-7 monocyclic or 8-10 membered bicyclic ring having one ring nitrogen and 0-4 additional heteroatoms selected from oxygen, phosphorus, sulfur, or nitrogen, optionally attached through a $C_{1-6}$ alkylene chain, and optionally substituted by one or more $R^8$; or (b)

$$\text{—N}(R_9)\text{—}(Y)_m\text{—}R^3;$$

(c)

$$\text{—C}(=\text{N—}R^8)\text{—N}(R^9)\text{—}(Y)_m\text{—}R^3;$$

(d)

$$\text{—C}(=\text{O})\text{—N}(R^9)\text{—}(Y)_m\text{—}R^3;$$

(e)

$$\text{—S}(=\text{O})_2\text{—N}(R^9)\text{—}(Y)_m\text{—}R^3; \text{ and}$$

(f)

$$\text{—C}(=\text{N—}R^8)\text{—Q—}(R^0)_w;$$

Q is carbon, oxygen, or —S(O)$_t$;

w is 1 or 2;

each $R^2$ is independently selected from —OR$^0$, —C(O)—R$^0$, —S(O)$_2$—R$^0$, —C(O)—N(R$^0$)$_2$, —S(O)$_2$—N(R$^0$)$_2$, —(CH$_2$)$_a$—N(R$^0$)(—V$_b$—R$^+$), —(CH$_2$)$_a$—(—V$_b$—R$^+$), halogen, alkyl optionally substituted by one or more R$^7$, alkenyl optionally substituted by one or more R$^7$, alkynyl optionally substituted by one or more R$^7$, aryl optionally substituted by one or more R$^6$, heteroaryl optionally substituted by one or more R$^6$, cycloalkyl optionally substituted by one or more R$^8$, or heterocyclyl optionally substituted by one or more R$^8$; and two adjacent R$^2$s on Ring A are optionally taken together to form a fused, saturated, partially saturated or aromatic 5-6 membered ring having 0-3 heteroatoms selected from oxygen, phosphorus, sulfur, or nitrogen; or two geminal $R^2$s are optionally taken together to form a spiro, saturated, partially saturated or aromatic 5-6 membered ring having 0-3 heteroatoms selected from oxygen, phosphorus, sulfur, or nitrogen, said fused or spiro ring being optionally substituted by one or more $R^8$;

each a independently is 0-3;

each b independently is 0 or 1;

V is —C(O)—, —C(O)O—, —S(O)$_2$—, or —C(O)—N($R^0$)—;

$R^+$ is alkyl, cycloalkyl, aralkyl, aryl, heteroaryl, heteroaralkyl, or heterocyclyl, wherein said $R^+$ is optionally substituted by one or more $R^8$;

d is 1-3;

m is 0 or 1;

n is 0-5;

$R^3$ is H, —N($R^0$)$_2$, —N($R^0$)C(O)$R^0$, —CN, halogen, CF$_3$, alkyl optionally substituted by one or more groups selected from $R^7$ or —S-aryl optionally substituted by —(CH$_2$)$_{1-6}$—N($R^0$)SO$_2$($R^0$) alkenyl optionally substituted by one or more groups selected from $R^7$ or —S-aryl optionally substituted by —(CH$_2$)$_{1-6}$—N($R^0$)SO$_2$($R^0$), alkynyl optionally substituted by one or more groups selected from $R^7$ or —S-aryl optionally substituted by —(CH$_2$)$_{1-6}$—N($R^0$)SO$_2$($R^0$), cycloalkyl or carbocyclyl optionally substituted by one or more $R^8$, aryl optionally substituted by one or more $R^6$, heteroaryl optionally substituted by one or more $R^6$, or heterocyclyl optionally substituted by one or more $R^8$;

Y is alkyl, alkenyl, alkynyl, —(CR$^4$R$^5$)$_p$—, —C(O)—, —C(O)C(O)—, —C(S)—, —O—(CH$_2$)$_{0-4}$—C(O)—, —(CH$_2$)$_{0-4}$—C(O)—O—, —N($R^0$)—C(O)—, —C(O)—N($R^0$)—, —N($R^0$)—C(S)—, —S(O)$_t$—, —O—C(=N—CN)—, —O—C(=N—$R^0$)—, —C(=N—CN)—O—, —C(=N—CN)—S—, —C(=N—$R^0$)—O—, —S—C(=N—CN)—, —N($R^0$)—C(=N—CN)—, —C(=N—CN)—, —N($R^0$)—C[=N—C(O)—$R^0$], —N($R^0$)—C[=N—S(O)$_t$—R], —N($R^0$)—C(=N—O$R^0$)—, —N($R^0$)—C(=N—$R^0$)— or —C(=N—$R^0$)—;

each $R^4$ is independently H, alkyl optionally substituted by $R^7$, alkenyl optionally substituted by $R^7$, or alkynyl optionally substituted by $R^7$;

each $R^5$ is independently selected from H, —C(O)—O$R^6$, —C(O)—N($R^0$)$_2$, —S(O)$_2$—N($R^0$)$_2$, —S(O)$_2$$R^0$, aryl optionally substituted by $R^6$, or heteroaryl optionally substituted by $R^6$;

p is 1-5;

each t independently is 1 or 2;

each $R^6$ is independently selected from halogen, —CF$_3$, —OCF$_3$, —O$R^0$, —(CH$_2$)$_{1-6}$—O$R^0$, —S$R^0$, —(CH$_2$)$_{1-6}$—S$R^0$, —SCF$_3$, —$R^0$, methylenedioxy, ethylenedioxy, —NO$_2$, —CN, —(CH$_2$)$_{1-6}$—CN, —N($R^0$)$_2$, —(CH$_2$)$_{1-6}$—N($R^0$)$_2$, —NR$^0$C(O)$R^0$, —NR$^0$(CN), —NR$^0$C(O)N($R^0$)$_2$, —NR$^0$C(S)N($R^0$)$_2$, —NR$^0$CO$_2$$R^0$, —NR$^0$NR$^0$C(O)$R^0$, —NR$^0$NR$^0$C(O)N($R^0$)$_2$—NR$^0$NR$^0$CO$_2$$R^0$, —C(O)C(O)$R^0$, —C(O)CH$_2$C(O)$R^0$, —(CH$_2$)$_{0-6}$CO$_2$$R^0$, —O—C(O)$R^0$, —C(O)$R^0$, —C(O)N($R^0$)N($R^0$)$_2$, —C(O)N($R^0$)$_2$, —C(O)N($R^0$)OH, —C(O)N($R^0$)SO$_2$$R^0$, —OC(O)N($R^0$)$_2$, —S(O)$_t$$R^0$, —S(O)$_t$—O$R^0$, —S(O)$_t$N($R^0$)C(O)$R^0$, —S(O)$_t$N($R^0$)O$R^0$, —NR$^0$SO$_2$N($R^0$)$_2$, —NR$^0$SO$_2$$R^0$, —C(=S)N($R^0$)$_2$, —C(=NH)—N($R^0$)$_2$, —(CH$_2$)$_{1-6}$—C(O)$R^0$, —C(=N—OR$^0$)—N($R^0$)$_2$, —O—(CH$_2$)$_{0-6}$—SO$_2$N($R^0$)$_2$, —(CH$_2$)$_{1-6}$NHC(O)$R^0$, or —SO$_2$N($R^0$)$_2$ wherein the two $R^0$s on the same nitrogen are optionally taken together to form a 5-8 membered saturated, partially saturated, or aromatic ring having additional 0-4 heteroatoms selected from oxygen, phosphorus, nitrogen, or sulfur;

each $R^7$ is independently selected from halogen, —CF$_3$, —$R^0$, —O$R^0$, —OCF$_3$, —(CH$_2$)$_{1-6}$—O$R^0$, —S$R^0$, —SCF$_3$, —(CH$_2$)$_{1-6}$—S$R^0$, aryl optionally substituted by $R^6$, methylenedioxy, ethylenedioxy, —NO$_2$, —CN, —(CH$_2$)$_{1-6}$—CN, —N($R^0$)$_2$, —(CH$_2$)$_{1-6}$—N($R^0$)$_2$, NR$^0$C(O)$R^0$, —NR$^0$(CN), —NR$^0$C(O)N($R^0$)$_2$, —N($R^0$)C(S)N($R^0$)$_2$, —NR$^0$CO$_2$$R^0$, —NR$^0$NR$^0$C(O)$R^0$, —NR$^0$NR$^0$C(O)N($R^0$)$_2$, —NR$^0$NR$^0$CO$_2$$R^0$, —C(O)C(O)$R^0$, —C(O)CH$_2$C(O)$R^0$, —(CH$_2$)$_{0-6}$—CO$_2$$R^0$, —C(O)$R^0$, —C(O)N($R^0$)N($R^0$)$_2$, —C(O)N($R^0$)$_2$, —C(O)N($R^0$)OH, —OC(O)$R^0$, —C(O)N($R^0$)SO$_2$$R^0$, —OC(O)N($R^0$)$_2$, —S(O)$_t$$R^0$, —S(O)$_t$—O$R^0$, —S(O)$_t$N($R^0$)C(O)$R^0$, —S(O)$_t$N($R^0$)O$R^0$, —NR$^0$SO$_2$N($R^0$)$_2$, —NR$^0$SO$_2$$R^0$, —C(=S)N($R^0$)$_2$, —C(=NH)—N($R^0$)$_2$, —(CH$_2$)$_{1-6}$—C(O)$R^0$, —C(=N—OR$^0$)—N($R^0$)$_2$, —O—(CH$_2$)$_{0-6}$—SO$_2$N($R^0$)$_2$, —(CH$_2$)$_{1-6}$—NHC(O)$R^0$, or —SO$_2$N($R^0$)$_2$ wherein the two $R^0$s on the same nitrogen are optionally taken together to form a 5-8 membered saturated, partially saturated, or aromatic ring having additional 0-4 heteroatoms selected from oxygen, phosphorus, nitrogen, or sulfur;

each $R^8$ is independently selected from $R^7$=O, =S, =N($R^0$), or =N(CN);

$R^9$ is hydrogen, alkyl optionally substituted by one or more $R^7$, alkenyl optionally substituted by one or more $R^7$, alkynyl optionally substituted by one or more $R^7$, cycloalkyl optionally substituted by one or more $R^8$, heterocyclyl optionally substituted by one or more $R^8$, heteroaryl optionally substituted by one or more $R^6$, or aryl optionally substituted by one or more $R^6$;

—(Y)$_m$—$R^3$ and $R^9$ may combine with the nitrogen atom with which they are attached to form a saturated, partially saturated, or aromatic 5-7 membered monocyclic or 8-10 membered bicyclic ring that optionally contains 1 to 3 additional heteroatoms selected from oxygen, phosphorus, nitrogen, or sulfur, wherein said ring may be optionally substituted with one or more $R^8$;

each $R^{10}$ is $R^7$ or two $R^{10}$ optionally may be taken together to form a 3-7 member saturated, partially saturated, or aromatic carbocyclic ring, optionally containing one or more heteroatom selected from oxygen, phosphorus, nitrogen, or sulfur that is fused with the depicted ring;

g is 0 to 4;

each $R^0$ is independently selected from hydrogen, alkyl, alkenyl, alkynyl, cycloalkyl, carbocyclylalkyl, aryl, heteroaryl, aralkyl, heteroaralkyl, heterocyclyl, or heterocyclylalkyl, wherein each member of $R^0$ except H is optionally substituted by one or more R*, OR*, N(R*)$_2$, =O, =S, halogen, CF$_3$, NO$_2$, CN, —C(O)R*, —CO$_2$R*, —C(O)-aryl, —C(O)-heteroaryl, —C(O)-aralkyl, —S(O)$_t$-aryl, —S(O)$_t$-heteroaryl, —NR*SO$_2$R*, —NR*C(O)R*, —NR*C(O)N(R*)$_2$, —N(R*)C(S)N(R*)$_2$, —NR*CO$_2$R*, —NR*NR*C(O)R*, —NR*NR*C(O)N(R*)$_2$, —NR*NR*CO$_2$R*, —C(O)C(O)R*, —C(O)CH$_2$C(O)R*, —C(O)N(R*)N(R*)$_2$, —C(O)N(R*)$_2$, —C(O)NR*SO$_2$R*, —OC(O)N(R*)$_2$, —S(O)$_t$R*, —NR*SO$_2$N(R*)$_2$, and —SO$_2$N(R*)$_2$ wherein the two R*s on the same nitrogen are optionally taken together to form a 5-8 membered saturated, partially saturated, or aromatic ring having additional 0-4 heteroatoms selected from oxygen, phosphorus, nitrogen or sulfur; and each R* is independently H, alkyl alkenyl, alkynyl, cycloalkyl, aryl, or heteroaryl.

In one embodiment, $R^1$ is
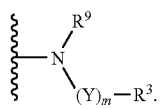
In one embodiment $R^9$ is alkyl and preferably $R^9$ is methyl.
In one embodiment —$(Y)_m$—$R^3$ suitably is
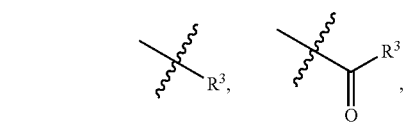
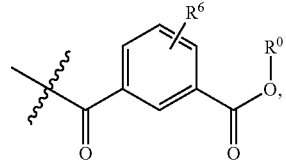
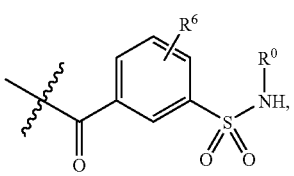
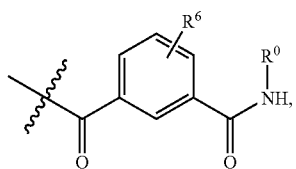 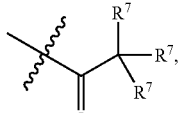
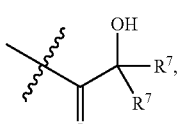 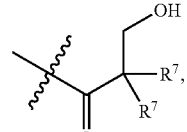
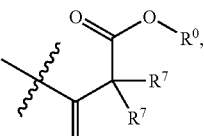 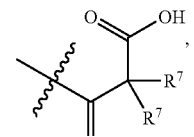
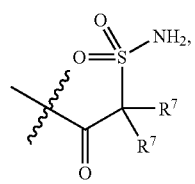 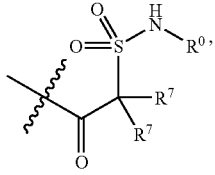
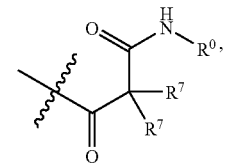
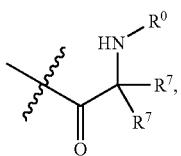 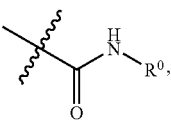
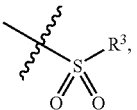
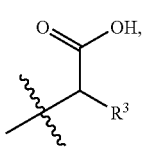
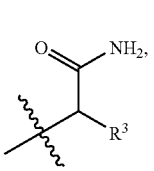
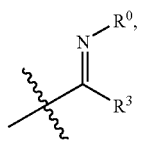
More suitably —$(Y)_m$—$R^3$ is
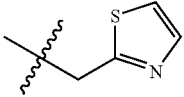 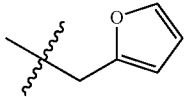
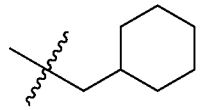 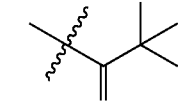
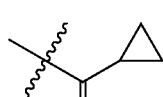 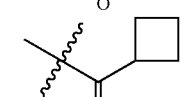
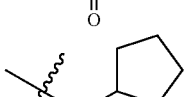 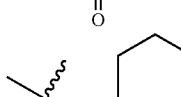
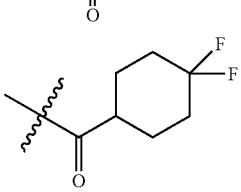 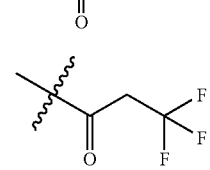

-continued
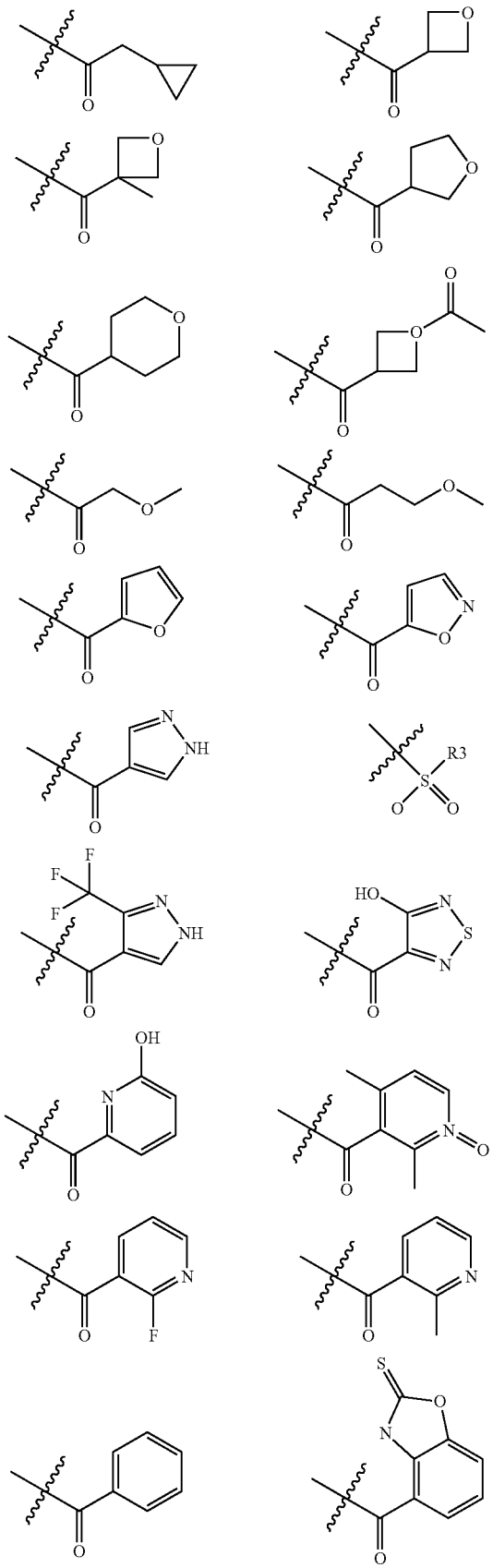
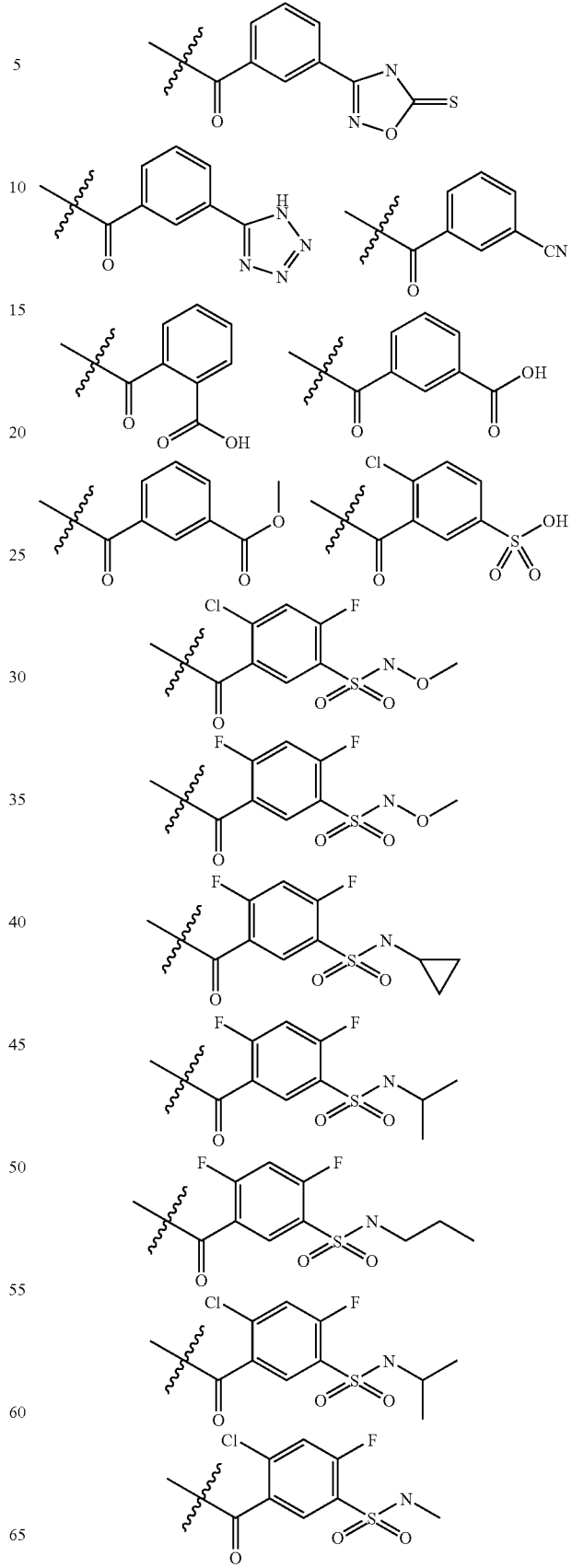

-continued
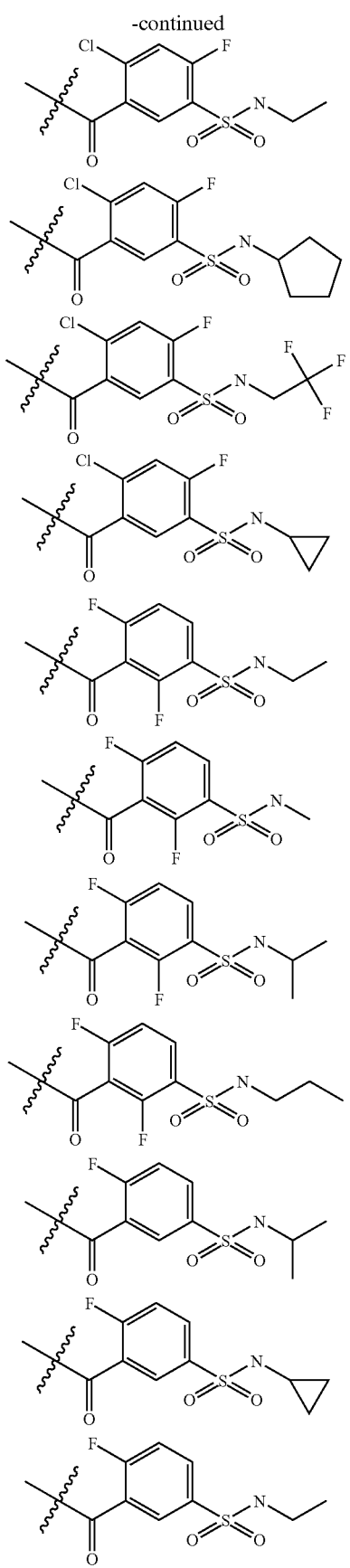
-continued
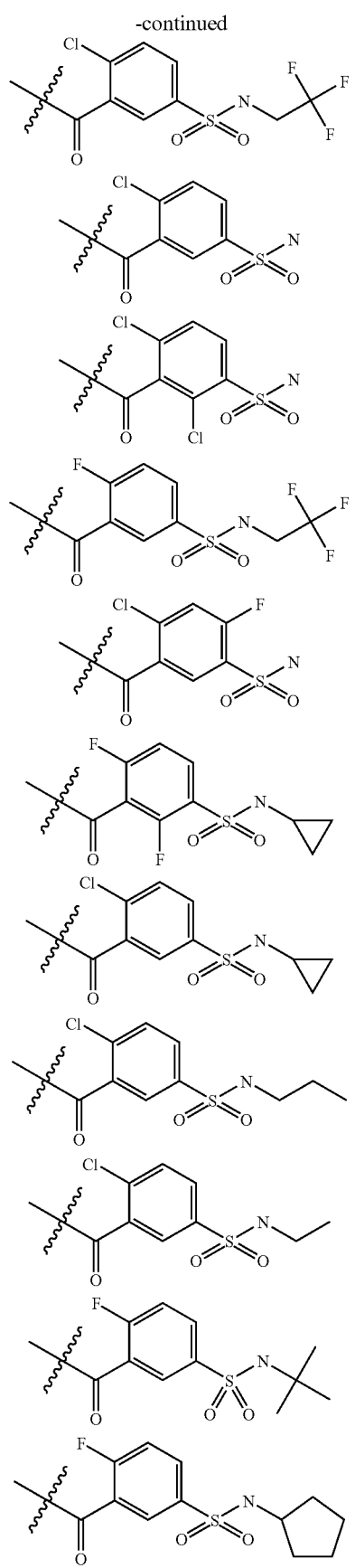

-continued
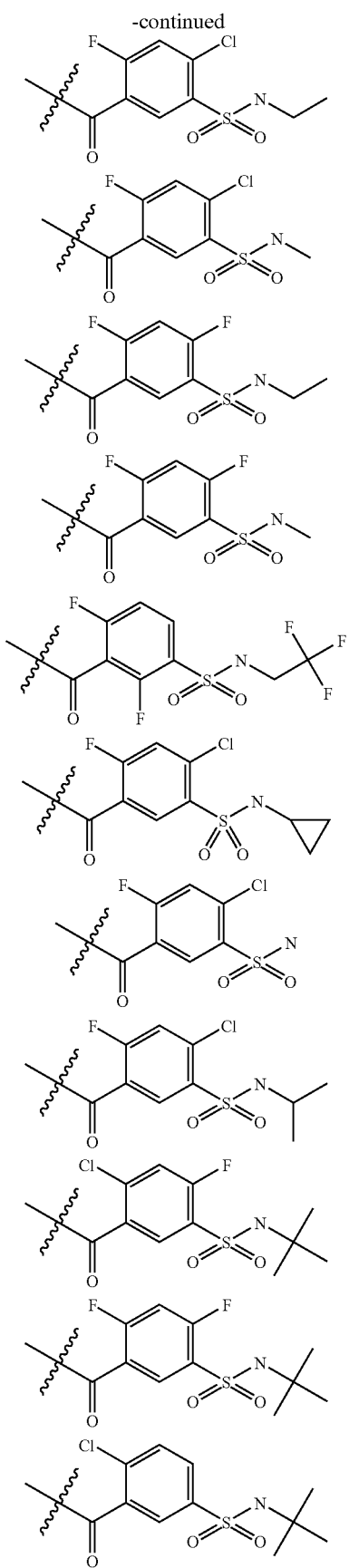
-continued
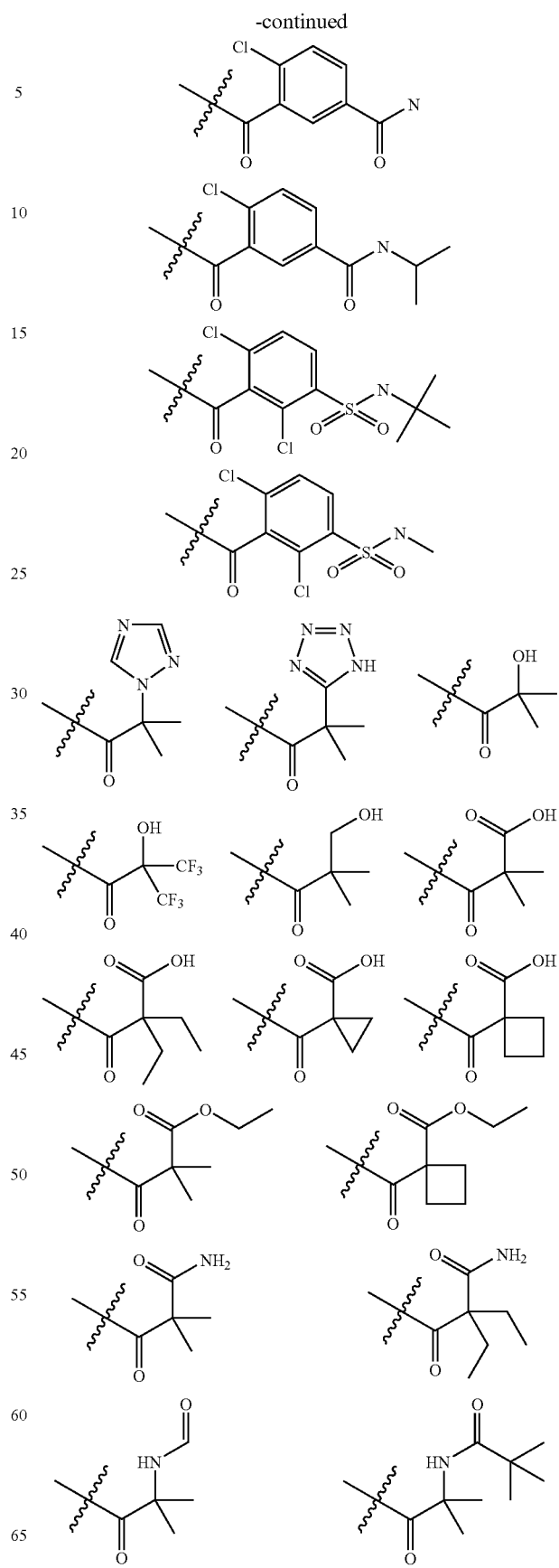

-continued
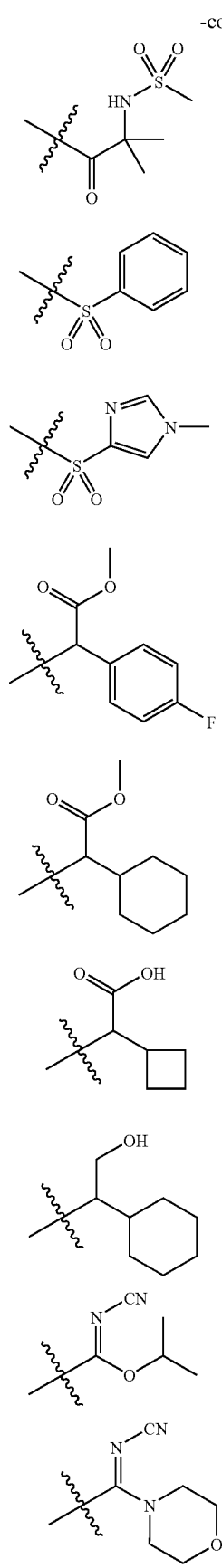
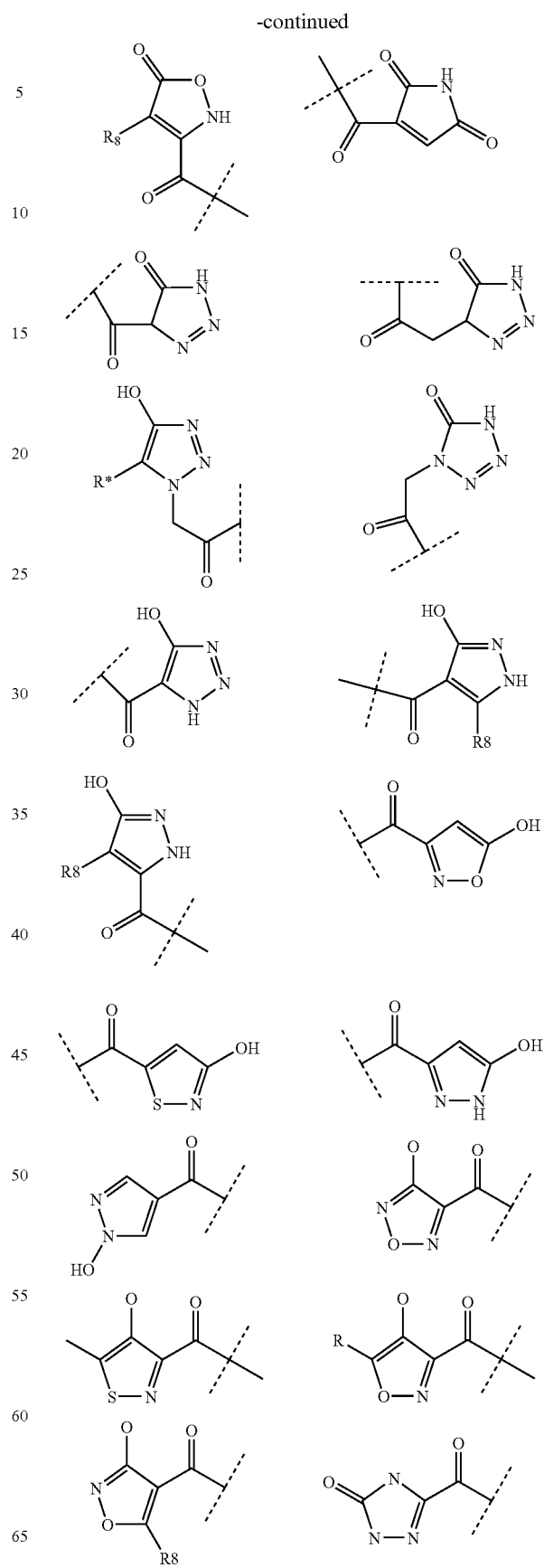

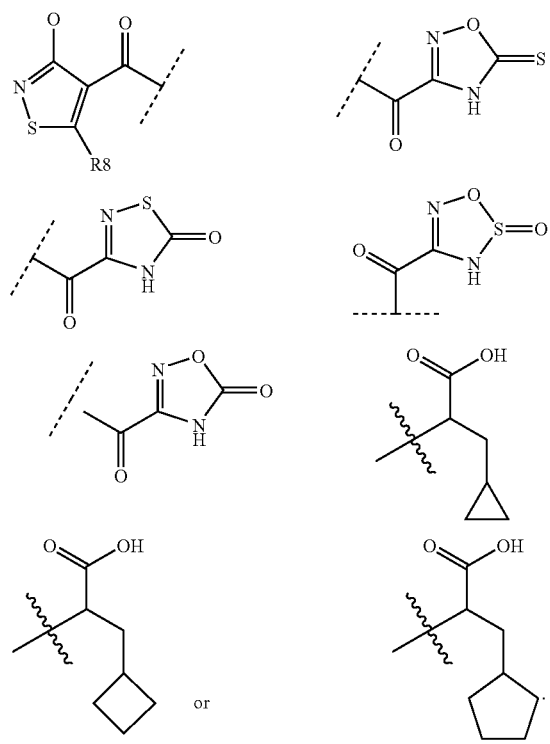
In another embodiment —(Y)$_m$—R$^3$ and —R$^9$ combine with the nitrogen atom to which they are attached to form
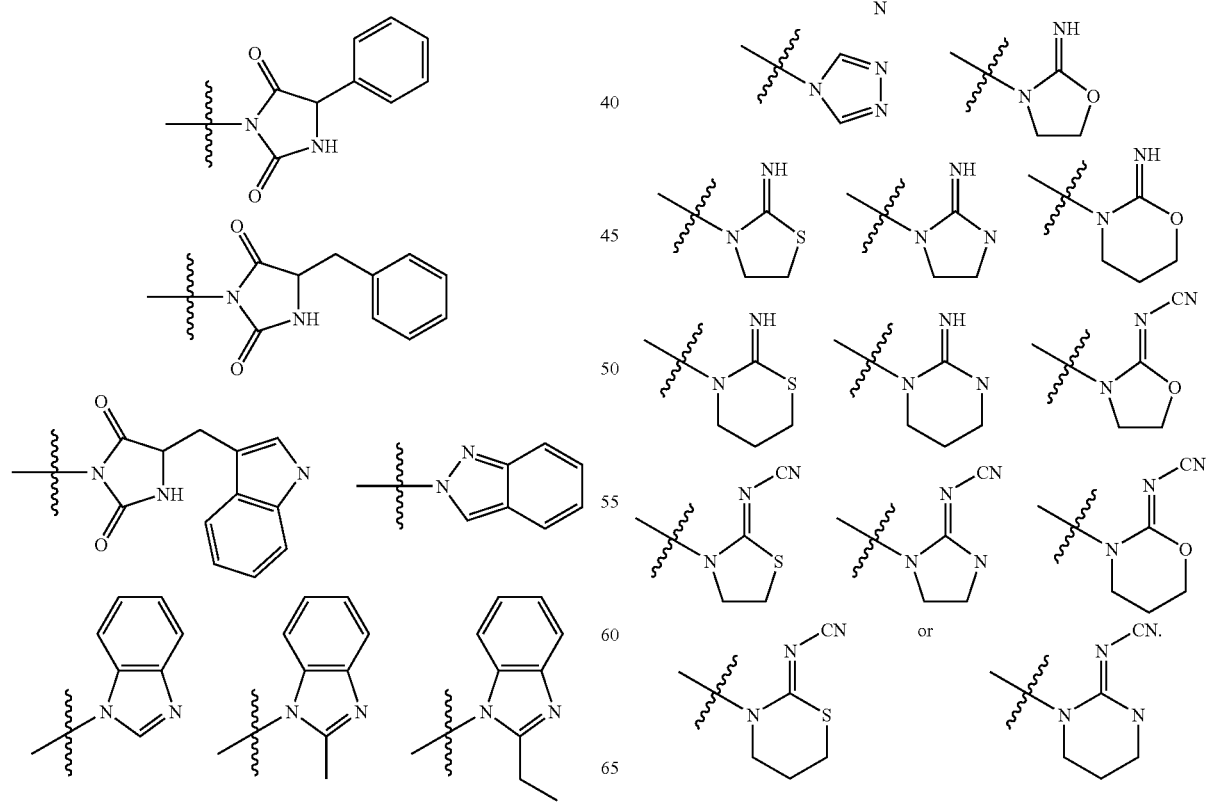
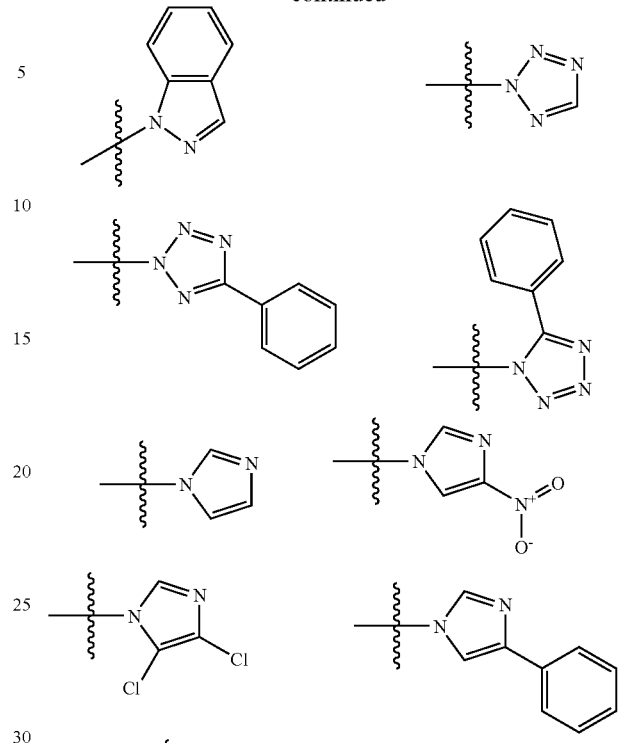

In one embodiment R¹ is selected from

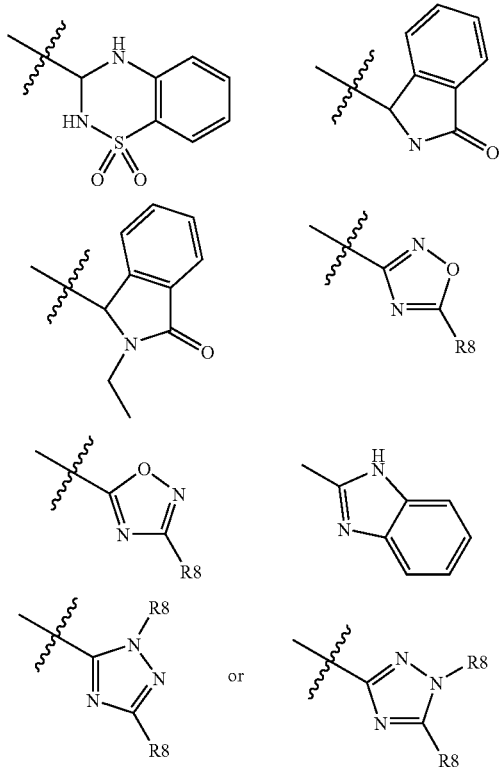

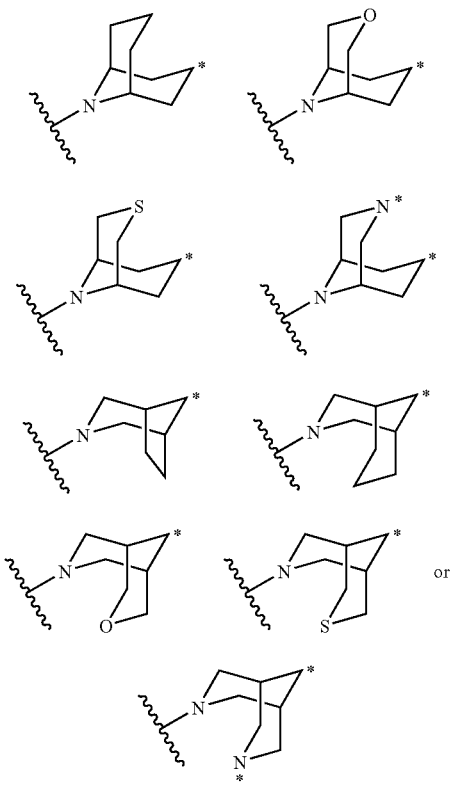

In one embodiment X is —(CH₂)—, —(CH₂—CH₂)—, or —(CH₂—CH₂—CH₂)—. Suitably X is optionally substituted by one or more halogen or oxo. Further X optionally has 1-3 heteroatoms selected from oxygen, phosphorus, sulfur, or nitrogen.

In one embodiment the A ring is selected from the following, where the asterisk (*) indicates the preferred, but not limiting, point(s) of substitution:

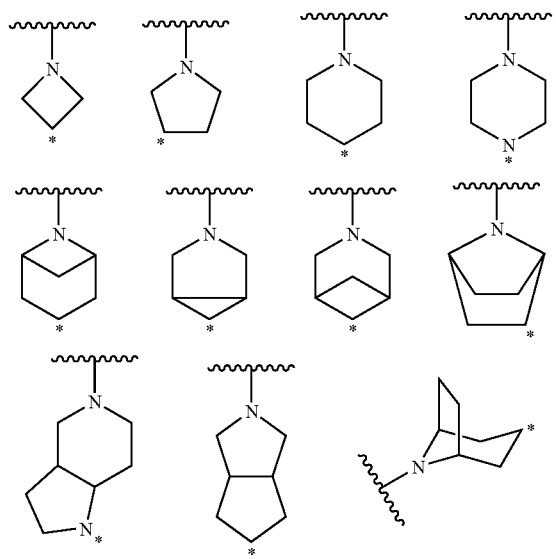

Suitably each R², with the asterisk (*) indicating a preferred, but not limiting, point of substitution from Ring A, independently is selected from

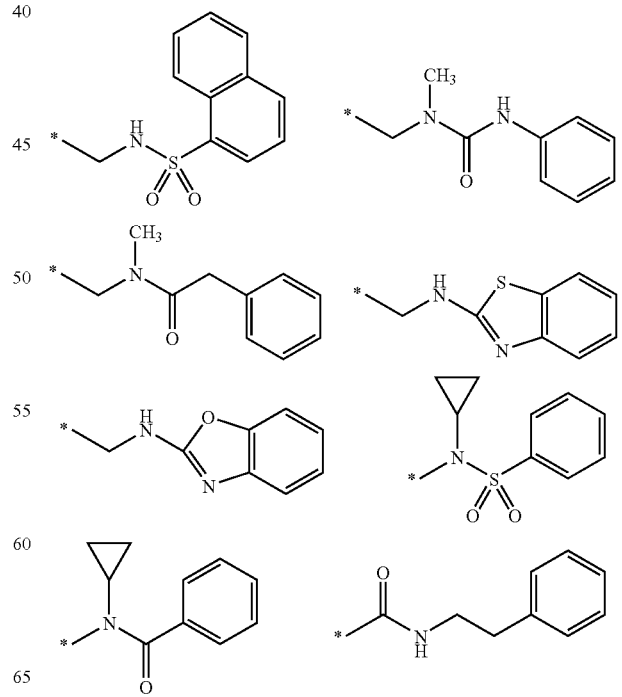

-continued
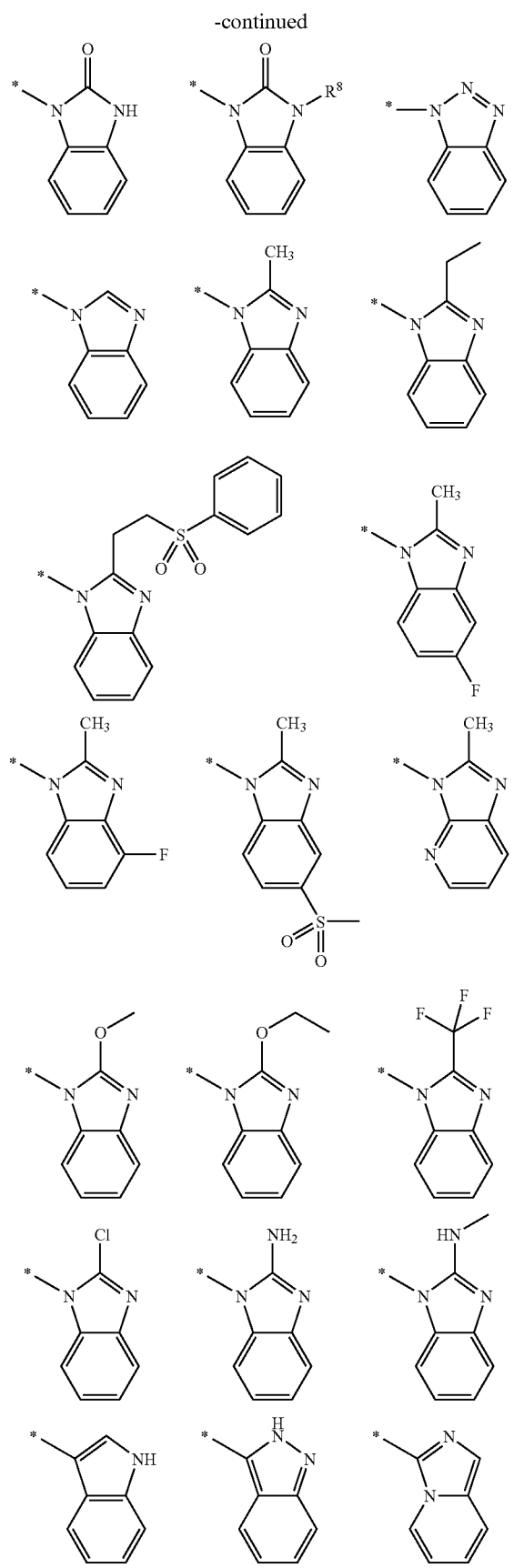
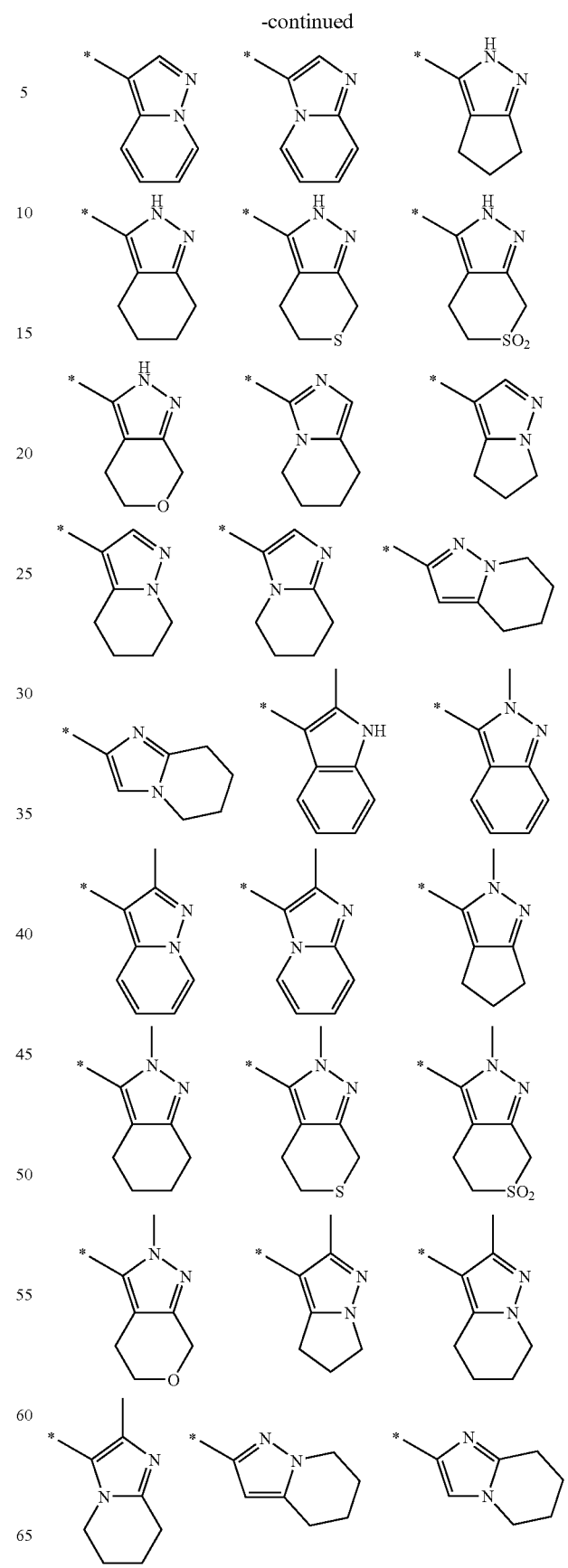

-continued
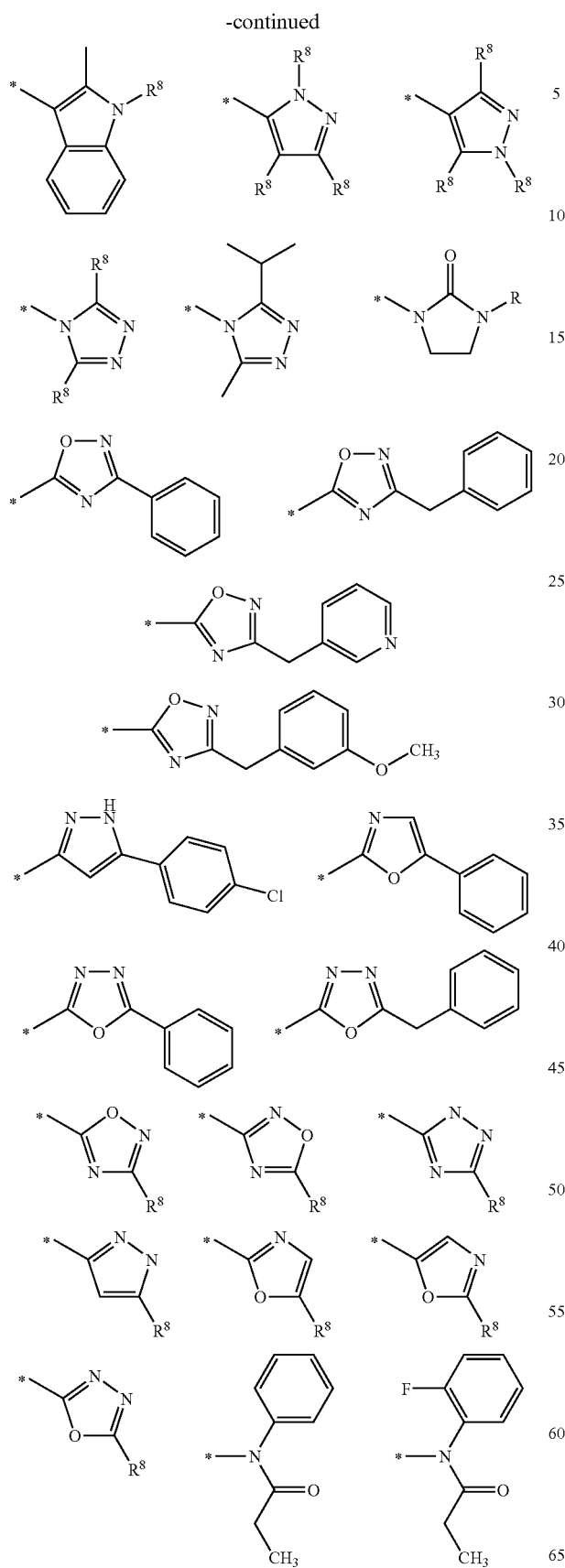
-continued
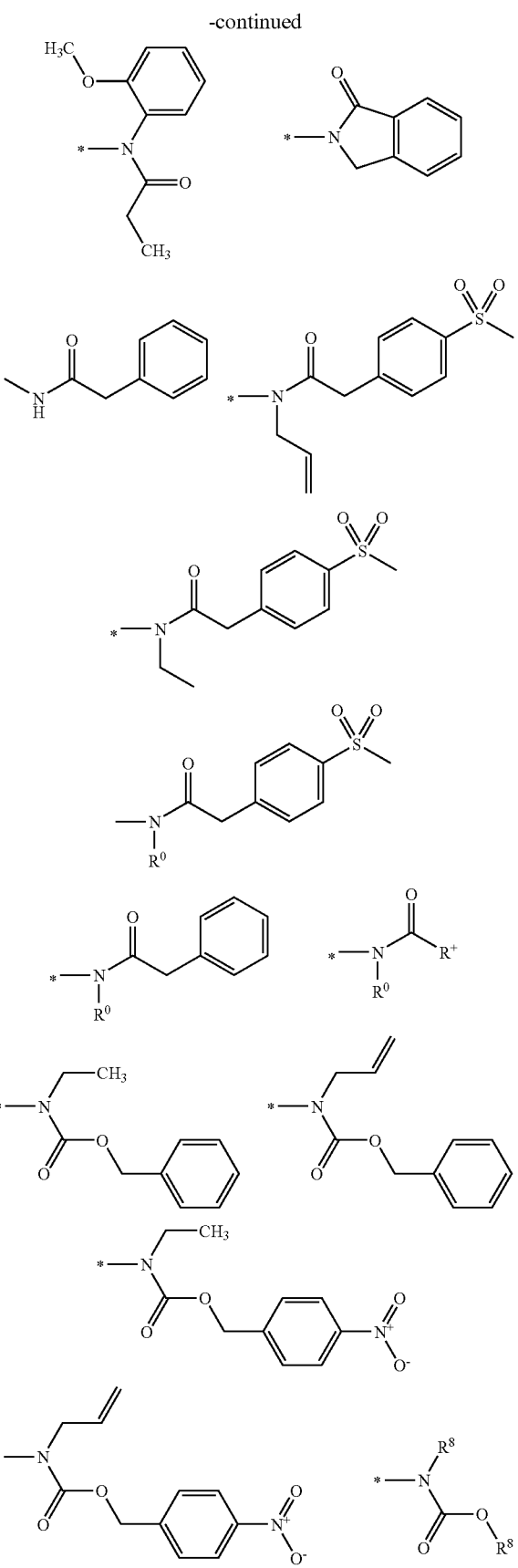

-continued

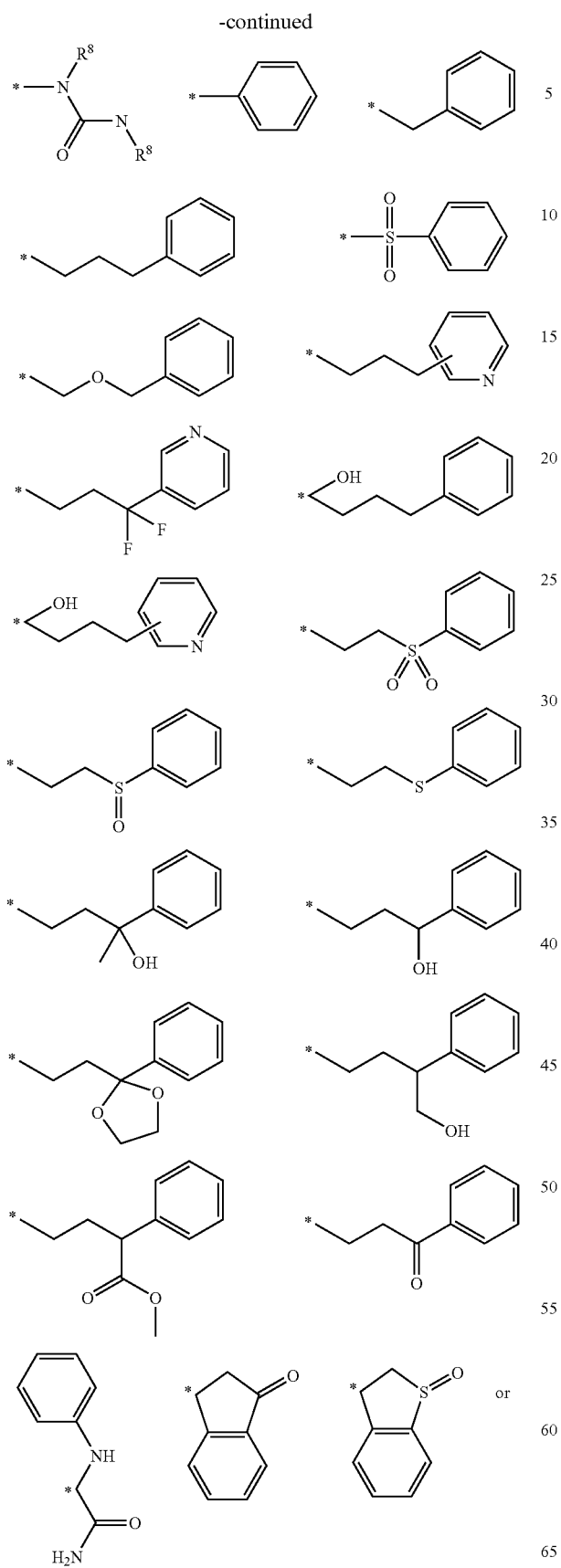

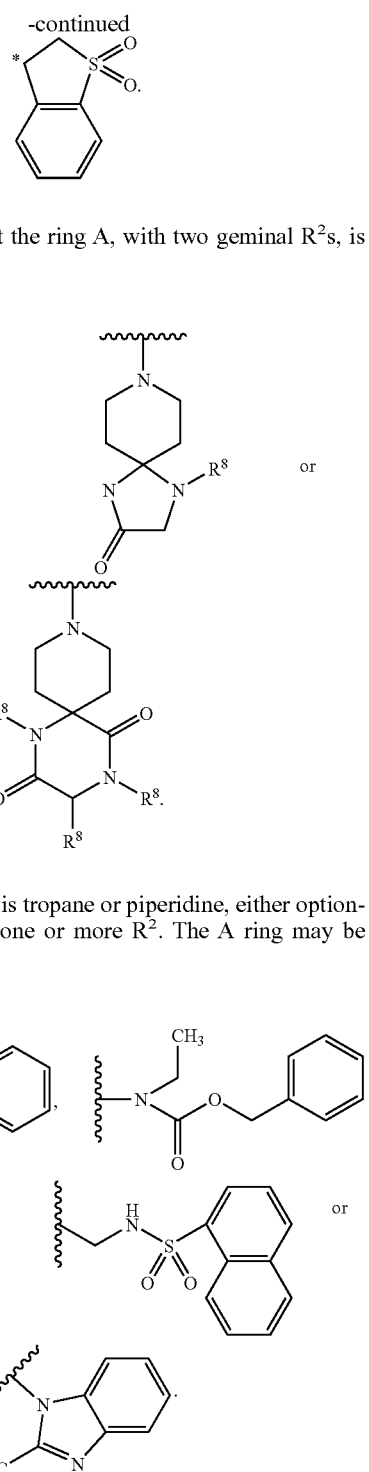

In one embodiment the ring A, with two geminal R²s, is selected from:

Suitably the A ring is tropane or piperidine, either optionally substituted with one or more R². The A ring may be substituted with In one embodiment the A ring contains at least one additional nitrogen atom and said A ring optionally is N-substituted. Suitably the A ring is N-substituted with —(CH$_2$)$_a$—(V$_b$—R+).

In one embodiment Ring B is a 4-7 membered saturated carbocyclic ring.

Another aspect of the present invention includes a method of treatment, including prevention, of a viral infection in a mammal comprising administering to said mammal an antiviral effective amount of a compound of the present invention. Preferably the viral infection is an HIV infection.

Another aspect of the present invention includes a method of treatment, including prevention, of a bacterial infection in a mammal comprising administering to said mammal an effective amount of a compound of the present invention. Preferably the bacterium is *Yersinia pestis*.

Another aspect of the present invention includes a method of treatment, including prevention, of multiple sclerosis, rheumatoid arthritis, autoimmune diabetes, chronic implant rejection, asthma, rheumatoid arthritis, Crohns Disease, inflammatory bowel disease, chronic inflammatory disease, glomerular disease, nephrotoxic serum nephritis, kidney disease, Alzheimer's Disease, autoimmune encephalomyelitis, arterial thrombosis, allergic rhinitis, arteriosclerosis, Sjogren's syndrome (dermatomyositis), systemic lupus erythematosus, graft rejection, cancers with leukocyte infiltration of the skin or organs, infectious disorders including bubonic and pnuemonic plague, human papilloma virus infection, prostate cancer, wound healing, amyotrophic lateral sclerosis and immune mediated disorders in a mammal comprising administering to said mammal a pharmaceutically effective amount of a compound of the present invention.

Another aspect of the present invention includes a compound of the present invention for use in medical therapy.

Another aspect of the present invention includes the use of a compound of the present invention in the manufacture of a medicament for the treatment including prophylaxis of a viral infection. Preferably the viral infection is a HIV infection.

Another aspect of the present invention includes the use of a compound of the present invention in the manufacture of a medicament for the treatment including prophylaxis of a bacterial infection. Preferably the bacterium is *Yersinia pestis*.

Another aspect of the present invention includes the use of a compound of the present invention in the manufacture of a medicament for the treatment including prophylaxis of multiple sclerosis, rheumatoid arthritis, autoimmune diabetes, chronic implant rejection, asthma, rheumatoid arthritis, Crohns Disease, inflammatory bowel disease, chronic inflammatory disease, glomerular disease, nephrotoxic serum nephritis, kidney disease, Alzheimer's Disease, autoimmune encephalomyelitis, arterial thrombosis, allergic rhinitis, arteriosclerosis, Sjogren's syndrome (dermatomyositis), systemic lupus erythematosus, graft rejection, cancers with leukocyte infiltration of the skin or organs, infectious disorders including bubonic and pnuemonic plague, human papilloma virus infection, prostate cancer, wound healing, amyotrophic lateral sclerosis and immune mediated disorders.

Another aspect of the present invention includes a pharmaceutical composition comprising a pharmaceutically effective amount of a compound of the present invention together with a pharmaceutically acceptable carrier. Preferably the pharmaceutical composition is in the form of a tablet, capsule, or liquid.

Another aspect of the present invention includes a method of treatment including prevention of a viral infection in a mammal comprising administering to said mammal a composition comprising a compound of the present invention and another therapeutic agent. Preferably, one or more other therapeutic agent is selected from the group consisting of (1-alpha, 2-beta, 3-alpha)-9-[2,3-bis(hydroxymethyl)cyclobutyl]guanine [(−)BHCG, SQ-34514, lobucavir], 9-[(2R,3R,4S)-3,4-bis(hydroxymethyl)-2-oxetanosyl]adenine (oxetanocin-G), acyclic nucleosides, acyclovir, valaciclovir, famciclovir, ganciclovir, penciclovir, acyclic nucleoside phosphonates, (S)-1-(3-hydroxy-2-phosphonyl-methoxypropyl)cytosine (HPMPC), [[[2-(6-amino-9H-purin-9-yl)ethoxy]methyl]phosphinylidene]bis(oxymethylene)-2,2-dimethylpropanoic acid (bis-POM PMEA, adefovir dipivoxil), [[(1R)-2-(6-amino-9H-purin-9-yl)-1-methylethoxy]methyl]phosphonic acid (tenofovir), (R)-[[2-(6-Amino-9H-purin-9-yl)-1-methylethoxy]methyl]phosphonic acid bis-(isopropoxycarbonyloxymethyl)ester (bis-POC-PMPA), ribonucleotide reductase inhibitors, 2-acetylpyridine 5-[(2-chloroanilino)thiocarbonyl) thiocarbonohydrazone and hydroxyurea, nucleoside reverse transcriptase inhibitors, 3'-azido-3'-deoxythymidine (AZT, zidovudine), 2',3'-dideoxycytidine (ddC, zalcitabine), 2',3'-dideoxyadenosine, 2',3'-dideoxyinosine (ddI, didanosine), 2',3'-didehydrothymidine (d4T, stavudine), (−)-beta-D-2,6-diaminopurine dioxolane (DAPD), 3'-azido-2',3'-dideoxythymidine-5'-H-phosphonate (phosphonovir), 2'-deoxy-5-iodo-uridine (idoxuridine), (−)-cis-1-(2-hydroxymethyl)-1,3-oxathiolane 5-yl)-cytosine (lamivudine), cis-1-(2-(hydroxymethyl)-1,3-oxathiolan-5-yl)-5-fluorocytosine (FTC), 3'-deoxy-3'-fluorothymidine, 5-chloro-2',3'-dideoxy-3'-fluorouridine, (−)-cis-4-[2-amino-6-(cyclopropylamino)-9H-purin-9-yl]-2-cyclopentene-1-methanol (abacavir), 9-[4-hydroxy-2-(hydroxymethyl)but-1-yl]-guanine (H2G), ABT-606 (2HM-H2G) ribavirin, protease inhibitors, indinavir, ritonavir, nelfinavir, amprenavir, saquinavir, fosamprenavir, (R)—N-tert-butyl-3-[(2S,3S)-2-hydroxy-3-N-[(R)-2-N-(isoquinolin-5-yloxyacetyl)amino-3-methylthiopropanoyl]amino-4-phenylbutanoyl]-5,5-dimethyl-1,3-thiazolidine-4-carboxamide (KNI-272), 4R-(4alpha,5alpha,6beta)]-1,3-bis[(3-aminophenyl)methyl]hexahydro-5,6-dihydroxy-4,7-bis(phenylmethyl)-2H-1,3-diazepin-2-one dimethanesulfonate (mozenavir), 3-[1-[3-[2-(5-trifluoromethylpyridinyl)-sulfonylamino]phenyl]propyl]-4-hydroxy-6alpha-phenethyl-6beta-propyl-5,6-dihydro-2-pyranone (tipranavir), N'-[2(S)-Hydroxy-3(S)-[N-(methoxycarbonyl)-I-tert-leucylamino]-4-phenylbutyl-N-alpha-(methoxycarbonyl)-N'-[4-(2-pyridyl)benzyl]-L-tert-leucylhydrazide (BMS-232632), 3-(2(S)-Hydroxy-3(S)-(3-hydroxy-2-methylbenzamido)-4-phenylbutanoyl)-5,5-dimethyl-N-(2-methylbenzyl)thiazolidine-4(R)-carboxamide (AG-1776), N-(2(R)-hydroxy-1(S)-indanyl)-2(R)-phenyl-methyl-4(S)-hydroxy-5-(1-(1-(4-benzo[b]furanylmethyl)-2(S)-N'-(tert-butylcarboxamido)piperazinyl)pentanamide (MK-944A), interferons, α-interferon, renal excretion inhibitors, probenecid, nucleoside transport inhibitors, dipyridamole, pentoxifylline, N-acetylcysteine (NAC), Procysteine, α-trichosanthin, phosphonoformic acid, immunomodulators, interleukin II, thymosin, granulocyte macrophage colony stimulating factors, erythropoetin, soluble $CD_4$ and genetically engineered derivatives thereof, non-nucleoside reverse transcriptase inhibitors (NNRTIs), nevirapine (BI-RG-587), alpha-((2-acetyl-5-methylphenyl)amino)-2,6-dichloro-benzeneacetamide (Ioviride), 1-[3-(isopropylamino)-2-pyridyl]-4-[5-(methanesulfonamido)-1H-indol-2-ylcarbonyl]piperazine monomethanesulfonate (delavirdine), (10R,11S,12S)-12-hydroxy-6,6,10,11-tetramethyl-4-propyl-11,12-dihydro-2H,6H, 10H-benzo(1,2-b:3,4-b':5,6-b")tripyran-2-one ((+) calanolide A), (4S)-6-Chloro-4-[1E)-cyclopropylethenyl)-3,4-dihydro-4-(trifluoromethyl)-2(1H)-quinazolinone (DPC-083), (S)-6-chloro-4-(cyclopropylethynyl)-1,4-dihydro-4-(trifluoromethyl)-2H-3,1-benzoxazin-2-one (efavirenz, DMP 266),1-(ethoxymethyl)-5-(1-methylethyl)-6-(phenylmethyl)-2,4(1H,3H)-pyrimidinedione (MKC-442), and 5-(3,5-dichlorophenyl)thio-4-isopropyl-1-(4-pyridyl)methyl-1H-imidazol-2-ylmethyl carbamate (capravirine), glycoprotein 120 antagonists, PRO-2000, PRO-542, 1,4-bis[3-[(2,4- dichlorophenyl)carbonylamino]-2-oxo-5,8-disodiumsulfa-nyl]naphthalyl-2,5-dimethoxyphenyl-1,4-dihydrazone (FP-21399), cytokine antagonists, reticulose (Product-R), 1,1'-azobis-formamide (ADA), 1,11-(1,4-phenylenebis(methylene))bis-1,4,8,11-tetraazacyclotetradecane octahydrochloride (AMD-3100), integrase inhibitors, and fusion inhibitors.

Another aspect of the present invention includes a method of treatment including prevention of a viral infection in a mammal comprising administering to said mammal a composition comprising a compound of the present invention and ritonavir.

Particular compounds of the present invention, and salts thereof, include:

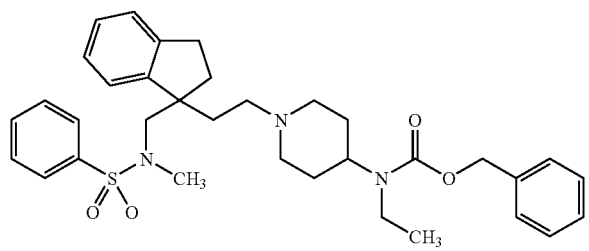

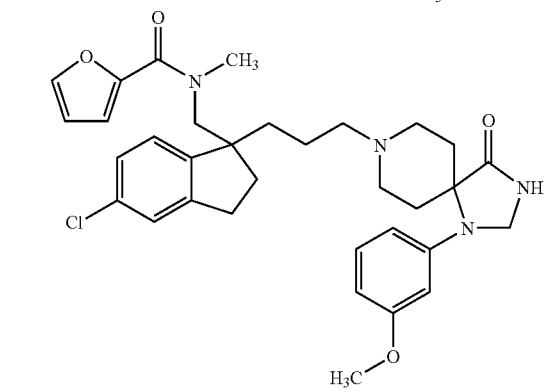

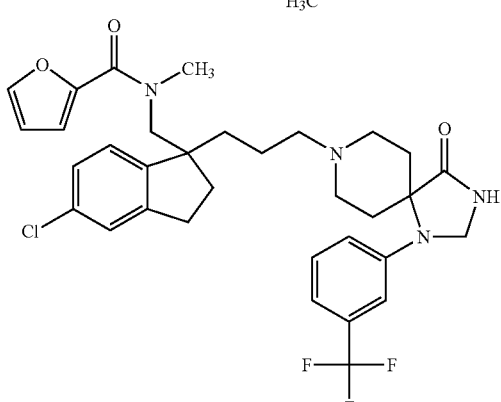

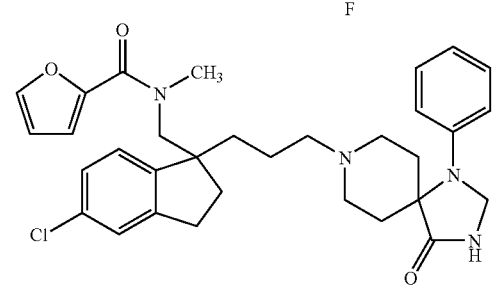

-continued

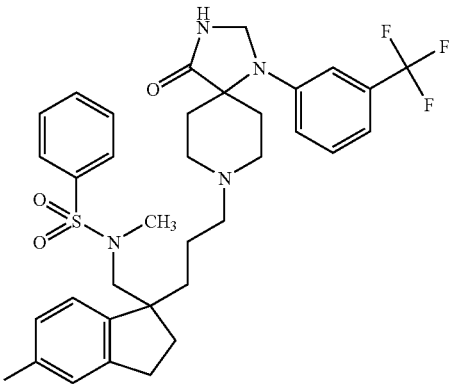

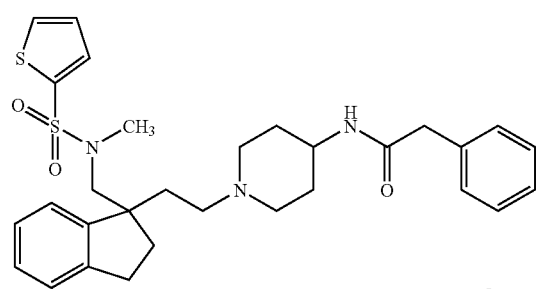

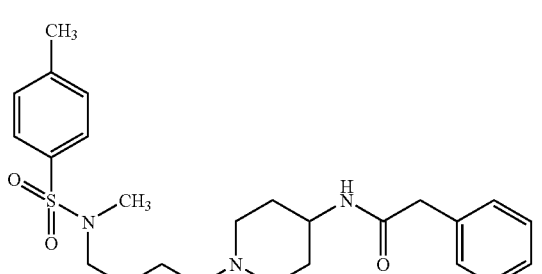

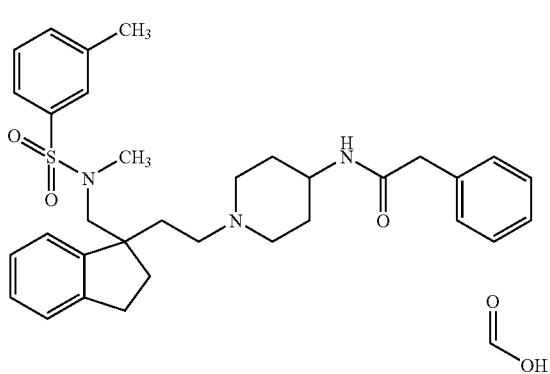

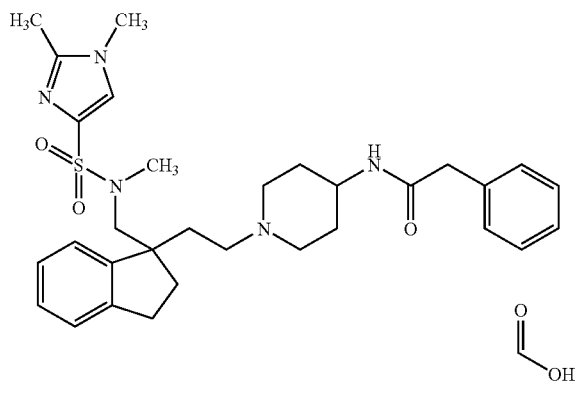
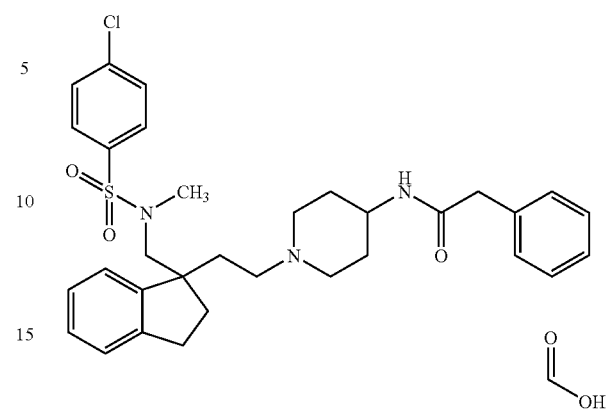
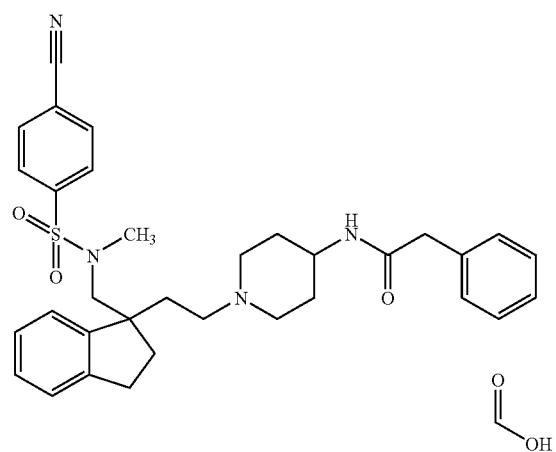
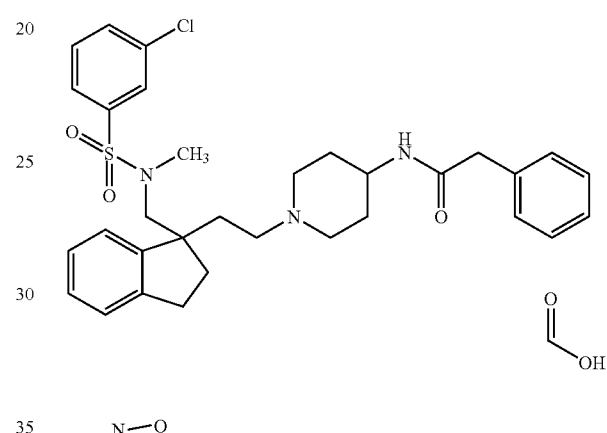
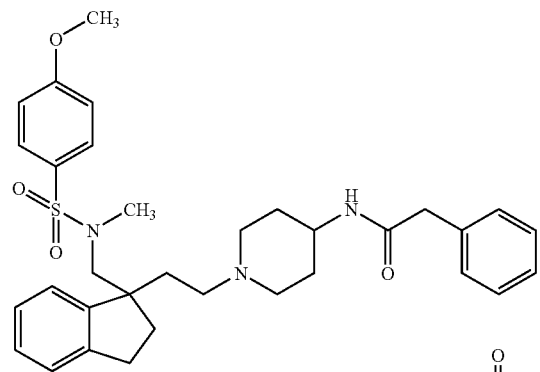
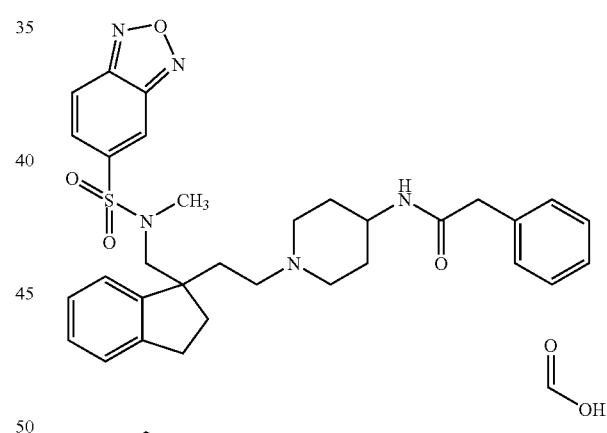
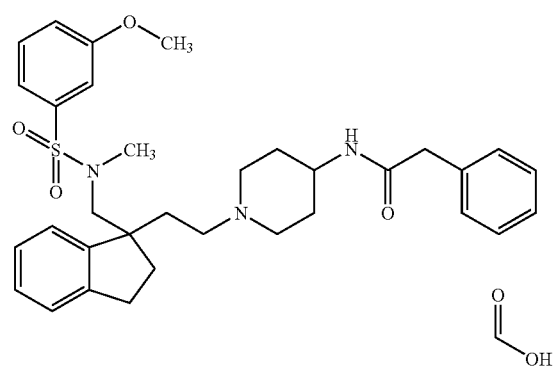
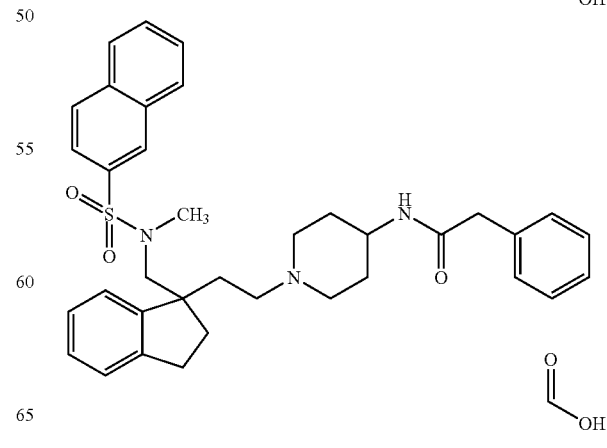

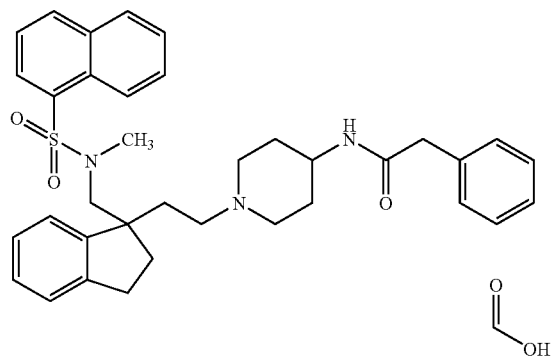
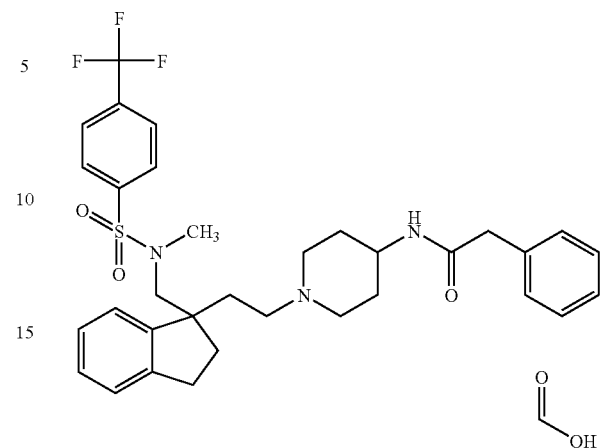
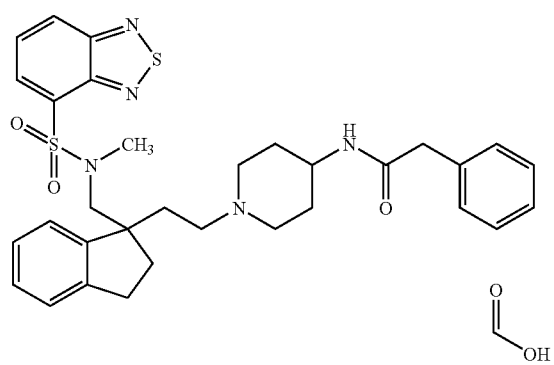
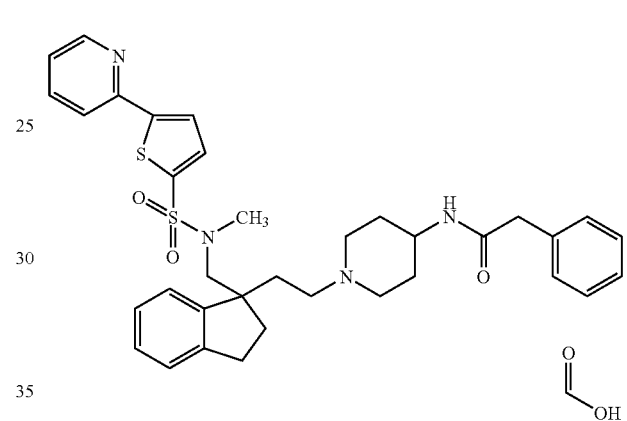
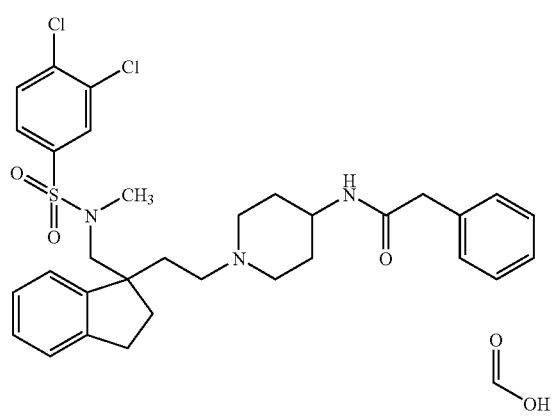
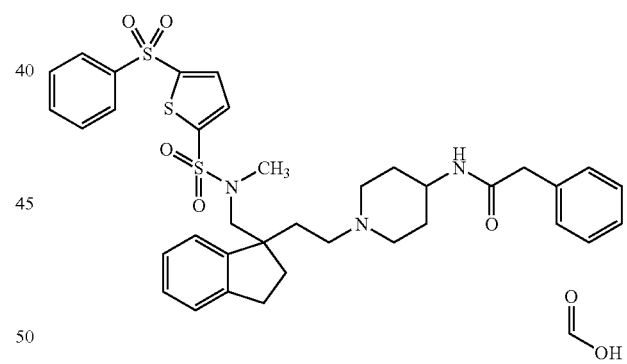
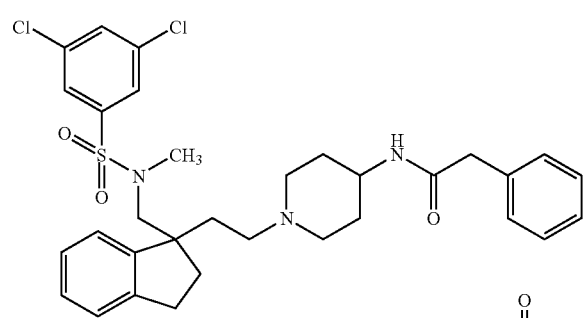
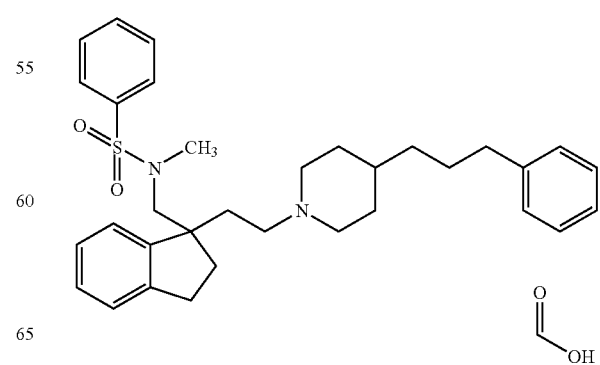

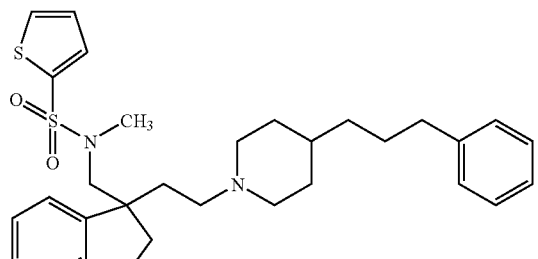
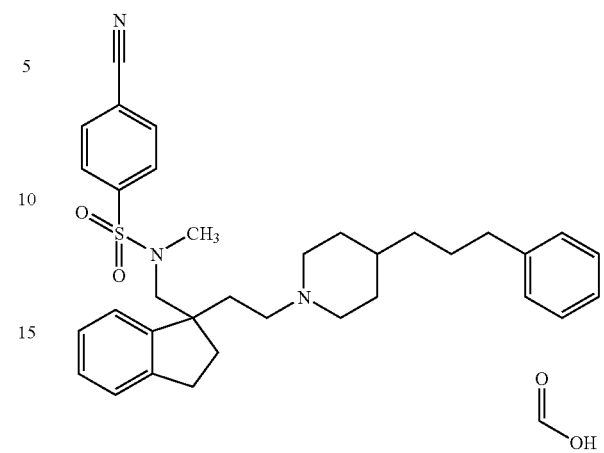
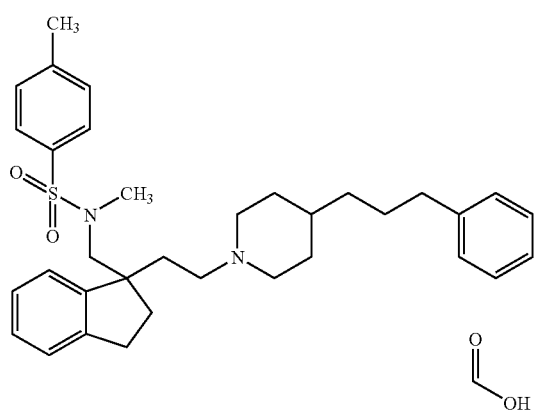
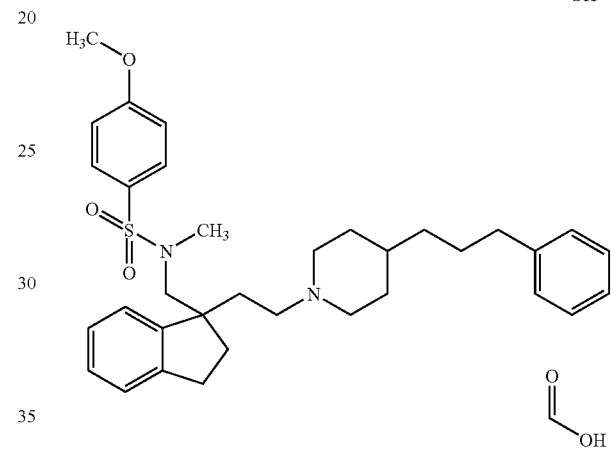
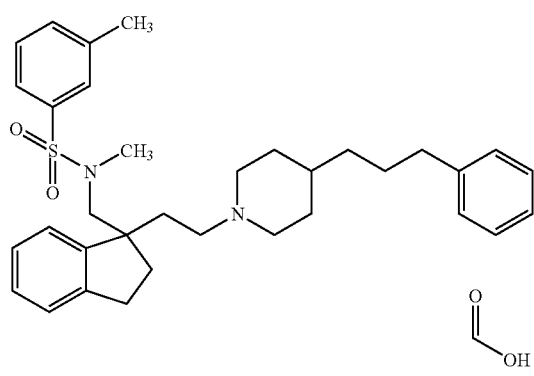
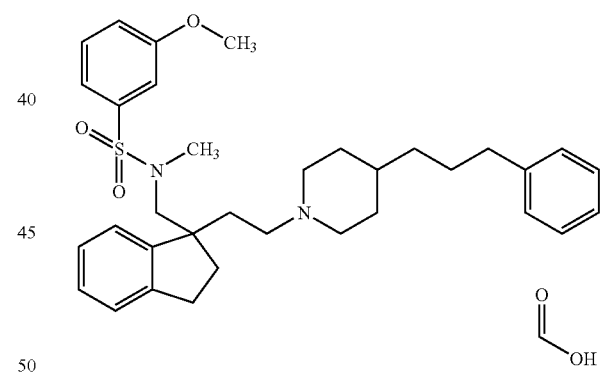
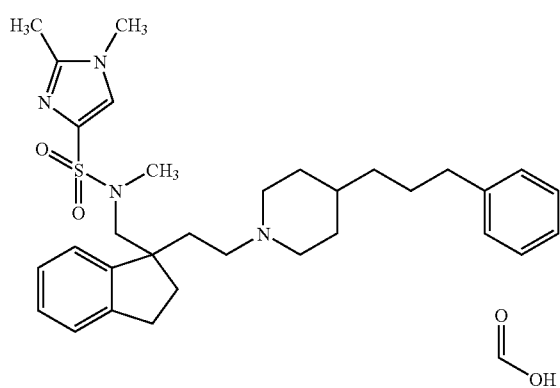
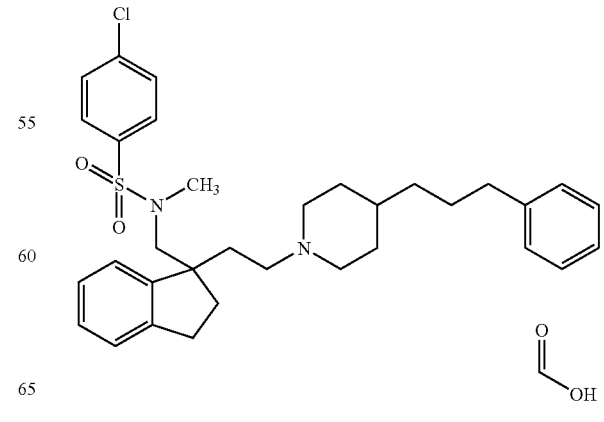

35
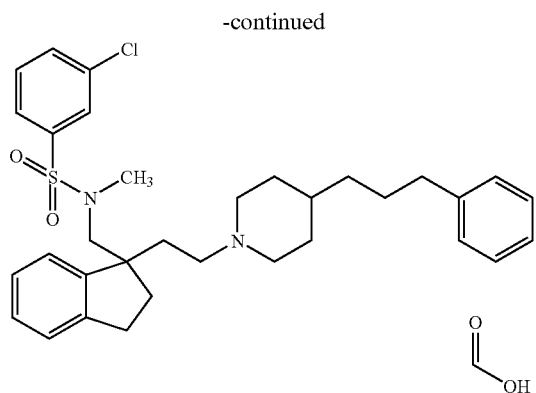
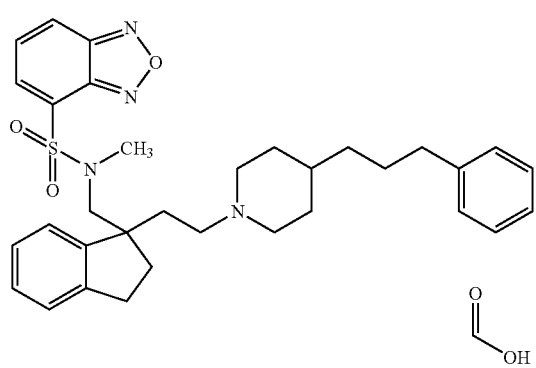
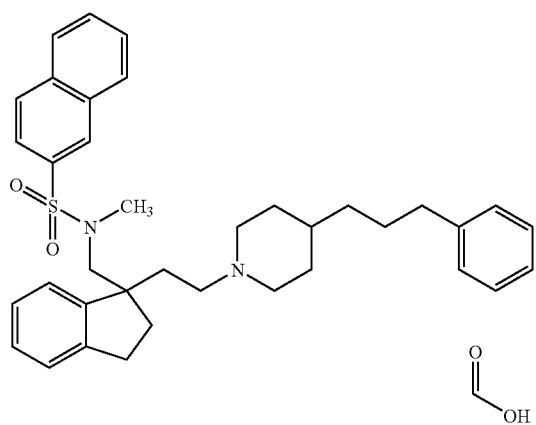
36
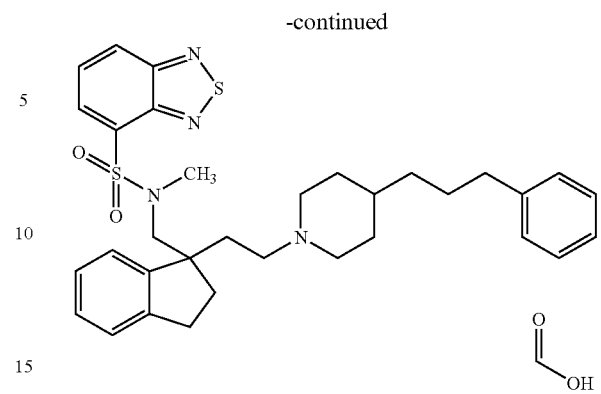
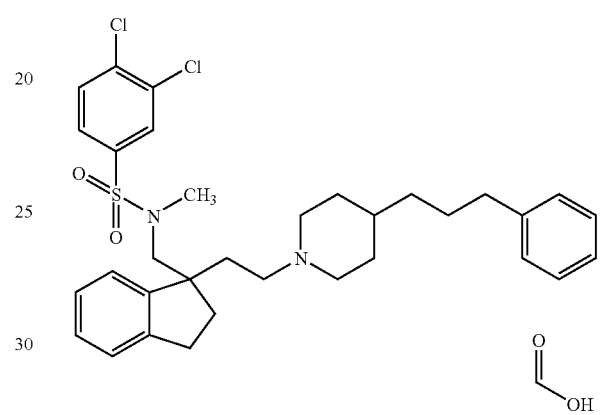

-continued

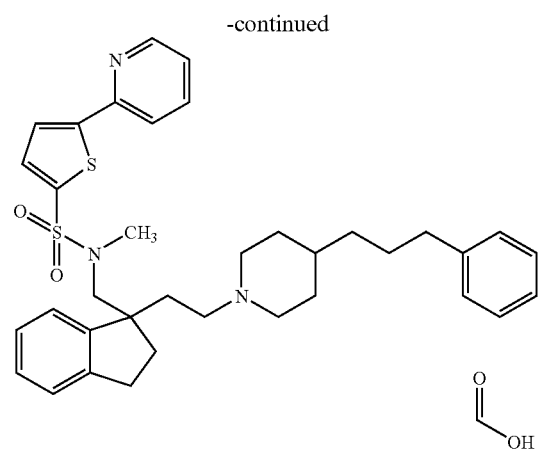

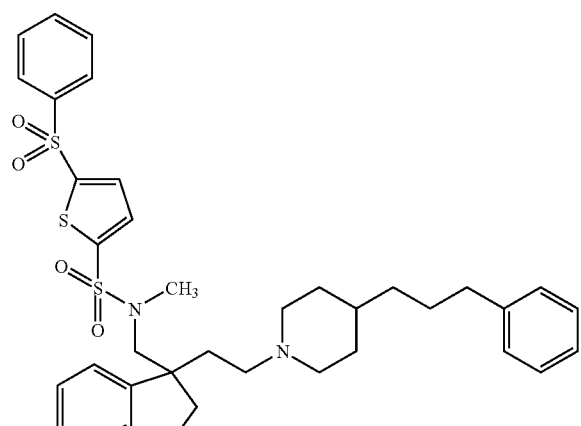

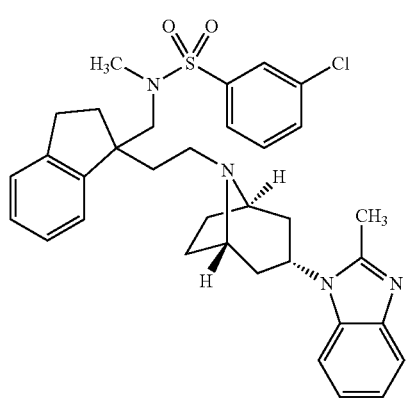

-continued

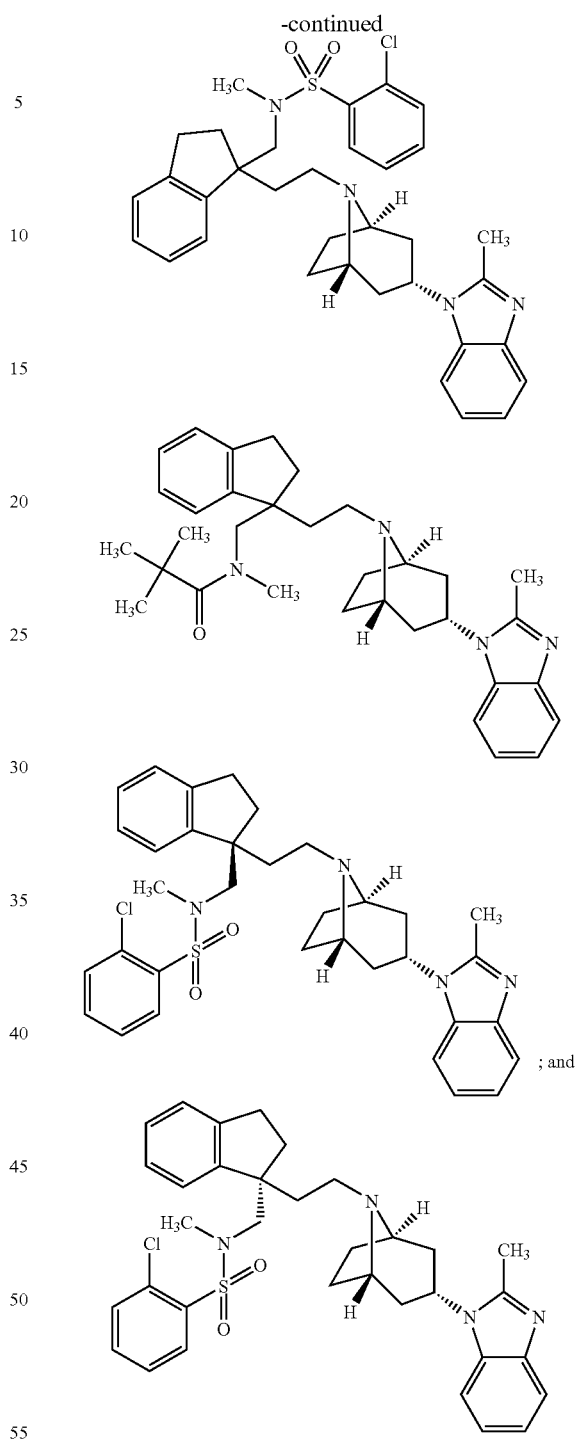

DETAILED DESCRIPTION OF THE INVENTION

The phrase "optionally substituted" is used interchangeably with the phrase "substituted or unsubstituted" or with the term "(un)substituted." Unless otherwise indicated, an optionally substituted group may have a substituent at each substitutable position of the group, and each substitution is independent of the other.

The term "alkyl", alone or in combination with any other term, refers to a straight chain or branched-chain saturated aliphatic hydrocarbon radical containing the specified number of carbon atoms. Examples of alkyl radicals include, but are not limited to, methyl, ethyl, n-propyl, isopropyl, n-butyl, isobutyl, sec-butyl, tert-butyl, pentyl, isoamyl, n-hexyl and the like.

The term "cycloalkyl", "carbocyclyl", "carbocyclic", or "carbocycle", or "carbocyclo", alone or in combination with any other term, refers to a monocyclic or polycyclic non-aromatic hydrocarbon ring radical having three to twenty carbon atoms, preferably from three to twelve carbon atoms, and more preferably from three to ten carbon atoms. If polycyclic, each ring in a carbocyclyl radical is non-aromatic unless otherwise indicated. A carbocyclyl radical is either completely saturated or contains one or more units of unsaturation but is not aromatic. The unsaturation, if present, may occur in any point in the ring that may result in any chemically stable configuration. The term "cycloalkyl", "carbocyclyl", "carbocyclic", or "carbocycle", or "carbocyclo" also includes hydrocarbon rings that are fused to one or more aromatic rings, such as in tetrahydronaphthyl, where the radical or point of attachment is on the non-aromatic ring.

Unless otherwise indicated, the term "cycloalkyl", "carbocyclyl", "carbocyclic", or "carbocycle", or "carbocyclo" also includes each possible positional isomer of a non-aromatic hydrocarbon radical, such as in 1-decahydronaphthyl, 2-decahydronaphthyl, 1-tetrahydronaphthyl and 2-tetrahydronaphthyl. Examples of suitable cycloalkyl groups include, but are not limited to, cyclopropyl, cyclobutyl, cyclopentyl, cyclohexyl, cyclohexenyl, decahydronaphthyl, tetrahydronaphthyl and the like.

The term "alkenyl," alone or in combination with any other term, refers to a straight chain or branched-chain alkyl group with at least one carbon-carbon double configuration with one or more carbon-carbon triple bonds which may occur in any stable point along the chain, such as ethynyl, propynyl, butynyl, pentynyl, and the like.

The term "alkoxy" refers to an alkyl ether radical, wherein the term "alkyl" is defined above. Examples of suitable alkyl ether radicals include, but are not limited to, methoxy, ethoxy, n-propoxy, isopropoxy, n-butoxy, isobutoxy, sec-butoxy, tert-butoxy and the like.

The term "aryl", alone or in combination with any other term, refers to an aromatic monocyclic or polycyclic hydrocarbon ring radical containing five to twenty carbon atoms, preferably from six to fourteen carbon atoms, and more preferably from six to ten carbon atoms. Also included within the scope of the term "aryl", as it is used herein, is a group in which an aromatic hydrocarbon ring is fused to one or more non-aromatic carbocyclic or heteroatom-containing rings, such as in an indanyl, phenanthridinyl or tetrahydronaphthyl, where the radical or point of attachment is on the aromatic hydrocarbon ring.

Unless otherwise indicated, the term "aryl" also includes each possible positional isomer of an aromatic hydrocarbon radical, such as in 1-naphthyl, 2-naphthyl, 5-tetrahydronaphthyl, 6-tetrahydronaphthyl, 1-phenanthridinyl, 2-phenanthridinyl, 3-phenanthridinyl, 4-phenanthridinyl, 7-phenanthridinyl, 8-phenanthridinyl, 9-phenanthridinyl and 10-phenanthridinyl. Examples of aryl radicals include, but are not limited to, phenyl, naphthyl, indenyl, azulenyl, fluorenyl, anthracenyl, phenanthrenyl, tetrahydronaphthyl, indanyl, phenanthridinyl and the like.

The term "aralkyl" further refers to groups of —$R_aR_b$, where $R_a$ is an alkylene as defined herein and $R_b$ is an aryl as defined herein.

The term "heterocycle", "heterocyclic", and "heterocyclyl", alone or in combination with any other term, refers to a non-aromatic monocyclic or polycyclic ring radical containing three to twenty carbon atoms, preferably three to seven carbon atoms if monocyclic and eight to eleven carbon atoms if bicyclic, and in which one or more ring carbons, preferably one to four, are each replaced by a heteroatom such as N, O and S. If polycyclic, each ring in a heterocyclyl radical is non-aromatic unless otherwise indicated. A heterocyclic ring may be fully saturated or may contain one or more units of unsaturation but is not aromatic. The unsaturation, if present, may occur in any point in the ring that may result in any chemically stable configuration. The heterocyclic ring may be attached at a carbon or heteroatom that results in the creation of a stable structure. Preferred heterocycles include 5-7 membered monocyclic heterocycles and 8-10 membered bicyclic heterocycles.

Also included within the scope of the term "heterocycle", "heterocyclic", or "heterocyclyl" is a group in which a non-aromatic heteroatom-containing ring is fused to one or more aromatic rings, such as in an indolinyl, chromanyl, phenanthridinyl or tetrahydroquinolinyl, where the radical or point of attachment is on the non-aromatic heteroatom-containing ring. Unless otherwise indicated, the term "heterocycle", "heterocyclic", or "heterocyclyl" also includes each possible positional isomer of a heterocyclic radical, such as in 1-decahydroquinoline, 2-decahydroquinoline, 3-decahydroquinoline, 4-decahydroquinoline, 5-decahydroquinoline, 6-decahydroquinoline, 7-decahydroquinoline, 7-decahydroquinoline, 8-decahydroquinoline, 4a-decahydroquinoline, 8a-decahydroquinoline, 1-indolinyl, 2-indolinyl, 3-indolinyl, 1-tetrahydroquinoline, 2-tetrahydroquinoline, 3-tetrahydroquinoline and 4-tetrahydroquinoline. The term "heterocyclylalkyl" refers to an alkyl group substituted by a heterocyclyl.

Examples of heterocyclic groups include, but are not limited to, imidazolinyl, 2,3-dihydro-1H-imidazolyl, imidazolidinyl, indazolinolyl, perhydropyridazyl, pyrrolinyl, pyrrolidinyl, 4H-pyrazolyl, piperidinyl, pyranyl, pyrazolinyl, piperazinyl, morpholinyl, thiamorpholinyl, thiazolidinyl, thiamorpholinyl, oxopiperidinyl, oxopyrrolidinyl, azepinyl, tetrahydrofuranyl, oxoazepinyl, tetrahydropyranyl, thiazolyl, dioxolyl, dioxinyl, oxathiolyl, benzodioxolyl, dithiolyl, dithiolanyl, tetrahydrothiophenyl, sulfolanyl, dioxanyl, dioxolanyl, tetrahydrofurodihydrofuranyl, dihydropyranyl, tetrahydropyranodihydrofuranyl, tetradyrofurofuranyl, tetrahydropyranofuranyl, diazolonyl, phthalimidinyl, benzoxanyl, benzopyrrolidinyl, benzopiperidinyl, benzoxolanyl, benzothiolanyl and benzothianyl.

The term "heteroaryl", alone or in combination with any other term, refers to an aromatic monocyclic or polycyclic ring radical containing five to twenty carbon atoms, preferably five to ten carbon atoms, in which one or more ring carbons, preferably one to four, are each replaced by a heteroatom such as N, O, and S. Preferred heteroaryl groups include 5-6 membered monocyclic heteroaryls and 8-10 membered bicyclic heteroaryls.

Also included within the scope of the term "heteroaryl" is a group in which a heteroaromatic ring is fused to one or more aromatic or non-aromatic rings where the radical or point of attachment is on the heteroaromatic ring. Examples include, but are not limited to, pyrido[3,4-d]pyrimidinyl, 7,8-dihydro-pyrido[3,4-d]pyrimidine and 5,6,7,8-tetrahydro-pyrido[3,4-d]pyrimidine. Unless otherwise indicated, the term "heteroaryl" also includes each possible positional isomer of a heteroaryl radical, such as in 2-pyrido[3,4-d]pyrimidinyl and 4-pyrido[3,4-d]pyrimidinyl.

Examples of heteroaryl groups include, but are not limited to, imidazolyl, quinolyl, isoquinolyl, indolyl, indazolyl, pyridazyl, pyridyl, pyrrolyl, pyrazolyl, pyrazinyl, quinoxalyl, pyrimidinyl, pyridazinyl, furyl, thienyl, triazolyl, thiazolyl, carbazolyl, carbolinyl, tetrazolyl, benzofuranyl, oxazolyl, benzoxazolyl, isoxazolyl, isothiazolyl, thiadiazolyl, furazanyl, oxadiazolyl, benzimidazolyl, benzothienyl, quinolinyl, benzotriazolyl, benzothiazolyl, isoquinolinyl, isoindolyl, acridinyl and benzoisoxazolyl.

The term "heteroarkyl" further refers to groups of —$R_a R_b$, where $R_a$ is an alkylene as defined herein and $R_b$ is a heteroaryl as defined herein.

The term "heteroatom" means nitrogen, oxygen, phosphorus, or sulfur and includes any oxidized forms thereof, including as non-limiting examples oxidized forms of nitrogen such as $N(O)$ {$N^+$—$O^-$}, oxidized forms of sulfur such as $S(O)$ and $S(O)_2$, and the quaternized form of any basic nitrogen.

The term "halogen" refers to fluorine, chlorine, bromine or iodine.

The term "pharmaceutically effective amount" refers to an amount of a compound of the invention that is effective in treating a CCR5-related disease, for example a virus infection, for example an HIV infection, in a patient either as monotherapy or in combination with other agents. The term "treatment" as used herein refers to the alleviation of symptoms of a particular disorder in a patient, or the improvement of an ascertainable measurement associated with a particular disorder, and may include the suppression of symptom recurrence in an asymptomatic patient such as a patient in whom a viral infection has become latent. The term "prophylaxis" refers to preventing a disease or condition or preventing the occurrence of symptoms of such a disease or condition, in a patient. As used herein, the term "patient" refers to a mammal, including a human.

The term "pharmaceutically acceptable carrier" refers to a carrier that may be administered to a patient, together with a compound of this invention, and which does not destroy the pharmacological activity thereof and is nontoxic when administered in doses sufficient to deliver a therapeutic amount of the therapeutic agent.

The term "pharmaceutically acceptable derivative" means any pharmaceutically acceptable salt, ester, salt of an ester, or other derivative of a compound of this invention which, upon administration to a recipient, is capable of providing (directly or indirectly) a compound of this invention or an inhibitorily active metabolite or residue thereof. Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species.

Pharmaceutically acceptable salts of the compounds according to the invention include those derived from pharmaceutically acceptable inorganic and organic acids and bases. Examples of suitable acids include hydrochloric, hydrobromic, sulfuric, nitric, perchloric, fumaric, maleic, phosphoric, glycollic, lactic, salicylic, succinic, toluene-p-sulfonic, tartaric, acetic, citric, methanesulfonic, ethanesulfonic, formic, benzoic, malonic, naphthalene-2-sulfonic and benzenesulfonic acids. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g. sodium), alkaline earth metal (e.g., magnesium), ammonium, $NW_4^+$ (wherein W is $C_{1-4}$ alkyl) and other amine salts. Physiologically acceptable salts of a hydrogen atom or an amino group include salts of organic carboxylic acids such as acetic, lactic, tartaric, malic, isethionic, lactobionic and succinic acids; organic sulfonic acids such as methanesulfonic, ethanesulfonic, benzenesulfonic and p-toluenesulfonic acids and inorganic acids such as hydrochloric, sulfuric, phosphoric and sulfamic acids. Physiologically acceptable salts of a compound with a hydroxy group include the anion of said compound in combination with a suitable cation such as $Na^+$, $NH_4^+$, and $NW_4^+$ (wherein W is a $C_{1-4}$alkyl group).

Any reference to any of the above compounds also includes a reference to a pharmaceutically acceptable salt thereof.

Salts of the compounds of the present invention may be made by methods known to a person skilled in the art. For example, treatment of a compound of the present invention with an appropriate base or acid in an appropriate solvent will yield the corresponding salt.

Esters of the compounds of the present invention are independently selected from the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted by, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

In such esters, unless otherwise specified, any alkyl moiety present advantageously contains from 1 to 18 carbon atoms, particularly from 1 to 6 carbon atoms, more particularly from 1 to 4 carbon atoms, Any cycloalkyl moiety present in such esters advantageously contains from 3 to 6 carbon atoms. Any aryl moiety present in such esters advantageously comprises a phenyl group.

The compounds according to the invention contain one or more asymmetric carbon atoms and thus occur as racemates and racemic mixtures, single enantiomers, diastereomeric mixtures and individual diastereoisomers. All such isomeric forms of these compounds are expressly included in the present invention. Each stereogenic carbon may be of the R or S configuration. Although the specific compounds exemplified in this application may be depicted in a particular stereochemical configuration, compounds having either the opposite stereochemistry at any given chiral center or mixtures thereof are also envisioned.

Unless otherwise stated, structures depicted herein are also meant to include compounds that differ only in the presence of one or more isotopically enriched atoms. For example, compounds having the present structures except for the replacement of a hydrogen by a deuterium or tritium, or the replacement of a carbon by a $^{13}C$— or $^{14}C$-enriched carbon are also within the scope of this invention.

Certain compounds of this invention may exist in alternative tautomeric forms. All such tautomeric forms of the present compounds are within the scope of the invention. Unless otherwise indicated, the representation of either tautomer is meant to include the other.

The present invention features compounds according to the invention for use in medical therapy, for example for the treatment or prophylaxis of viral infections such as an HIV infections and associated conditions. Reference herein to treatment extends to prophylaxis as well as the treatment of established infections, symptoms, and associated clinical conditions such as AIDS related complex (ARC), Kaposi's sarcoma, and AIDS dementia.

The present invention features use of the compounds of the present invention in the manufacture of a medicament for the treatment or prophylaxis of a CCR5-related disease or condition, for example, a viral infection, for example, an HIV infection.

According to another aspect, the present invention provides a method for the treatment or prevention of the symptoms or effects of a viral infection in an infected animal, for example, a mammal including a human, which comprises treating said animal with a pharmaceutically effective amount of a compound according to the invention. According to one aspect of the invention, the viral infection is a retroviral infection, in particular an HIV infection. A further aspect of the invention includes a method for the treatment or prevention of the symptoms or effects of an HBV infection.

The compounds according to the invention may also be used in adjuvant therapy in the treatment of HIV infections or HIV-associated symptoms or effects, for example Kaposi's sarcoma.

The compounds of the present invention may also be used in the prevention or treatment of other CCR5-related diseases and conditions, including multiple sclerosis, rheumatoid arthritis, autoimmune diabetes, chronic implant rejection, asthma, rheumatoid arthritis, Crohns Disease, inflammatory bowel disease, chronic inflammatory disease, glomerular disease, nephrotoxic serum nephritis, kidney disease, Alzheimer's Disease, autoimmune encephalomyelitis, arterial thrombosis, allergic rhinitis, arteriosclerosis, Sjogren's syndrome (dermatomyositis), systemic lupus erythematosus, graft rejection, cancers with leukocyte infiltration of the skin or organs, infectious disorders including bubonic and pneumonic plague, human papilloma virus infection, prostate cancer, wound healing, amyotrophic lateral sclerosis, immune mediated disorders.

The present invention further provides a method for the treatment of a clinical condition in an animal, for example, a mammal including a human which clinical condition includes those which have been discussed hereinbefore, which comprises treating said animal with a pharmaceutically effective amount of a compound according to the invention. The present invention also includes a method for the treatment or prophylaxis of any of the aforementioned diseases or conditions.

In yet a further aspect, the present invention provides the use of a compound according to the invention in the manufacture of a medicament for the treatment or prophylaxis of any of the above mentioned viral infections or conditions.

The above compounds according to the invention and their pharmaceutically acceptable derivatives may be employed in combination with other therapeutic agents for the treatment of the above infections or conditions. Combination therapies according to the present invention comprise the administration of a compound of the present invention or a pharmaceutically acceptable derivative thereof and another pharmaceutically active agent. The active ingredient(s) and pharmaceutically active agents may be administered simultaneously in either the same or different pharmaceutical compositions or sequentially in any order. The amounts of the active ingredient(s) and pharmaceutically active agent(s) and the relative timings of administration will be selected in order to achieve the desired combined therapeutic effect.

Examples of such therapeutic agents include agents that are effective for the treatment of viral infections or associated conditions. Among these agents are (1-alpha, 2-beta, 3-alpha)-9-[2,3-bis(hydroxymethyl)cyclobutyl]guanine [(−)BHCG, SQ-34514, lobucavir], 9-[(2R,3R,4S)-3,4-bis(hydroxymethyl)-2-oxetanosyl]adenine (oxetanocin-G), acyclic nucleosides, for example acyclovir, valaciclovir, famciclovir, ganciclovir, and penciclovir, acyclic nucleoside phosphonates, for example (S)-1-(3-hydroxy-2-phosphonyl-methoxypropyl)cytosine (HPMPC), [[[2-(6-amino-9H-purin-9-yl)ethoxy]methyl]phosphinylidene]bis(oxymethylene)-2,2-dimethylpropanoic acid (bis-POM PMEA, adefovir dipivoxil), [[(1R)-2-(6-amino-9H-purin-9-yl)-1-methylethoxy]methyl]phosphonic acid (tenofovir), and (R)-[[2-(6-Amino-9H-purin-9-yl)-1-methylethoxy]methyl]phosphonic acid bis-(isopropoxycarbonyloxymethyl)ester (bis-POC-PMPA), ribonucleotide reductase inhibitors, for example 2-acetylpyridine 5-[(2-chloroanilino)thiocarbonyl) thiocarbonohydrazone and hydroxyurea, nucleoside reverse transcriptase inhibitors, for example 3'-azido-3'-deoxythymidine (AZT, zidovudine), 2',3'-dideoxycytidine (ddC, zalcitabine), 2',3'-dideoxyadenosine, 2',3'-dideoxyinosine (ddI, didanosine), 2',3'-didehydrothymidine (d4T, stavudine), (−)-beta-D-2,6-diaminopurine dioxolane (DAPD), 3'-azido-2',3'-dideoxythymidine-5'-H-phosphophosphonate (phosphonovir), 2'-deoxy-5-iodo-uridine (idoxuridine), (−)-cis-1-(2-hydroxymethyl)-1,3-oxathiolane 5-yl)-cytosine (lamivudine), cis-1-(2-(hydroxymethyl)-1,3-oxathiolan-5-yl)-5-fluorocytosine (FTC), 3'-deoxy-3'-fluorothymidine, 5-chloro-2',3'-dideoxy-3'-fluorouridine, (−)-cis-4-[2-amino-6-(cyclopropylamino)-9$\underline{H}$-purin-9-yl]-2-cyclopentene-1-methanol (abacavir), 9-[4-hydroxy-2-(hydroxymethyl)but-1-yl]-guanine (H2G), ABT-606 (2HM-H2G) and ribavirin, protease inhibitors, for example indinavir, ritonavir, nelfinavir, amprenavir, saquinavir, fosamprenavir, (R)—N-tert-butyl-3-[(2S,3S)-2-hydroxy-3-N-[(R)-2-N-(isoquinolin-5-yloxyacetyl)amino-3-methylthiopropanoyl]amino-4-phenylbutanoyl]-5,5-dimethyl-1,3-thiazolidine-4-carboxamide (KNI-272), 4R-(4alpha,5alpha,6beta)]-1,3-bis[(3-aminophenyl)methyl] hexahydro-5,6-dihydroxy-4,7-bis(phenylmethyl)-2H-1,3-diazepin-2-one dimethanesulfonate (mozenavir), 3-[1-[3-[2-(5-trifluoromethylpyridinyl)-sulfonylamino]phenyl]propyl]-4-hydroxy-6alpha-phenethyl-6beta-propyl-5,6-dihydro-2-pyranone (tipranavir), N'-[2(S)-Hydroxy-3(S)-[N-(methoxycarbonyl)-I-tert-leucylamino]-4-phenylbutyl-N$^{alpha}$-(methoxycarbonyl)-N'-[4-(2-pyridyl)benzyl]-L-tert-leucylhydrazide (BMS-232632), 3-(2(S)-Hydroxy-3(S)-(3-hydroxy-2-methylbenzamido)-4-phenylbutanoyl)-5,5-dimethyl-N-(2-methylbenzyl)thiazolidine-4(R)-carboxamide (AG-1776), N-(2(R)-hydroxy-1(S)-indanyl)-2(R)-phenyl-methyl-4(S)-hydroxy-5-(1-(1-(4-benzo[b] furanylmethyl)-2(S)—N'-(tert-butylcarboxamido) piperazinyl)pentanamide (MK-944A), interferons such as α-interferon, renal excretion inhibitors such as probenecid, nucleoside transport inhibitors such as dipyridamole; pentoxifylline, N-acetylcysteine (NAC), Procysteine, α-trichosanthin, phosphonoformic acid, as well as immunomodulators such as interleukin II or thymosin, granulocyte macrophage colony stimulating factors, erythropoetin, soluble $CD_4$ and genetically engineered derivatives thereof, non-nucleoside reverse transcriptase inhibitors (NNRTIs), for example nevirapine (BI-RG-587), alpha-((2-acetyl-5-methylphenyl)amino)-2,6-dichloro-benzeneacetamide (Ioviride), 1-[3-(isopropylamino)-2-pyridyl]-4-[5-(methanesulfonamido)-1H-indol-2-ylcarbonyl]piperazine monomethanesulfonate (delavirdine), (10R,11S,12S)-2-Hydroxy-6,6,10,11-tetramethyl-4-propyl-11,12-dihydro-2H, 6H, 10H-benzo(1,2-b:3,4-b':5,6-b")tripyran-2-one ((+) calanolide A), (4S)-6-Chloro-4-[1E)-cyclopropylethenyl]-3,4- dihydro-4-(trifluoromethyl)-2(1H)-quinazolinone (DPC-083), (S)-6-chloro-4-(cyclopropylethynyl)-1,4-dihydro-4-(trifluoromethyl)-2H-3,1-benzoxazin-2-one (efavirenz, DMP 266), 1-(ethoxymethyl)-5-(1-methylethyl)-6-(phenylmethyl)-2,4(1H,3H)-pyrimidinedione (MKC-442), and 5-(3,5-dichlorophenyl)thio-4-isopropyl-1-(4-pyridyl)methyl-1H-imidazol-2-ylmethyl carbamate (capravirine), glycoprotein 120 antagonists, for example PRO-2000, PRO-542 and 1,4-bis[3-[(2,4-dichlorophenyl)carbonylamino]-2-oxo-5,8-disodiumsulfanyl]naphthalyl-2,5-dimethoxyphenyl-1,4-dihydrazone (FP-21399), cytokine antagonists, for example reticulose (Product-R), 1,1'-azobis-formamide (ADA), 1,11-(1,4-phenylenebis(methylene))bis-1,4,8,11-tetraazacyclotetradecane octahydrochloride (AMD-3100), integrase inhibitors, or fusion inhibitors, for example T-20 and T-1249.

The present invention further includes the use of a compound according to the invention in the manufacture of a medicament for simultaneous or sequential administration with at least another therapeutic agent, such as those defined hereinbefore.

Compounds of the present invention may be administered with an agent known to inhibit or reduce the metabolism of compounds, for example ritonavir. Accordingly, the present invention features a method for the treatment or prophylaxis of a disease as hereinbefore described by administration of a compound of the present invention in combination with a metabolic inhibitor. Such combination may be administered simultaneously or sequentially.

In general a suitable dose for each of the above-mentioned conditions will be in the range of 0.01 to 250 mg per kilogram body weight of the recipient (e.g. a human) per day, preferably in the range of 0.1 to 100 mg per kilogram body weight per day and most preferably in the range 0.5 to 30 mg per kilogram body weight per day and particularly in the range 1.0 to 20 mg per kilogram body weight per day. Unless otherwise indicated, all weights of active ingredient are calculated as the parent compound of formula (I); for salts or esters thereof, the weights would be increased proportionally. The desired dose may be presented as one, two, three, four, five, six or more sub-doses administered at appropriate intervals throughout the day. In some cases the desired dose may be given on alternative days. These sub-doses may be administered in unit dosage forms, for example, containing 10 to 1000 mg or 50 to 500 mg, preferably 20 to 500 mg, and most preferably 50 to 400 mg of active ingredient per unit dosage form.

While it is possible for the active ingredient to be administered alone it is preferable to present it as a pharmaceutical composition. The compositions of the present invention comprise at least one active ingredient, as defined above, together with one or more acceptable carriers thereof and optionally other therapeutic agents. Each carrier must be acceptable in the sense of being compatible with the other ingredients of the composition and not injurious to the patient.

Pharmaceutical compositions include those suitable for oral, rectal, nasal, topical (including transdermal, buccal and sublingual), vaginal or parenteral (including subcutaneous, intramuscular, intravenous, intradermal, and intravitreal) administration. The compositions may conveniently be presented in unit dosage form and may be prepared by any methods well known in the art of pharmacy. Such methods represent a further feature of the present invention and include the step of bringing into association the active ingredients with the carrier, which constitutes one or more accessory ingredients. In general, the compositions are prepared by uniformly and intimately bringing into association the active ingredients with liquid carriers or finely divided solid carriers or both, and then if necessary shaping the product.

The present invention further includes a pharmaceutical composition as hereinbefore defined wherein a compound of the present invention or a pharmaceutically acceptable derivative thereof and another therapeutic agent each are presented separately from one another as a kit of parts.

Compositions suitable for transdermal administration may be presented as discrete patches adapted to remain in intimate contact with the epidermis of the recipient for a prolonged period of time. Such patches suitably contain the active compound 1) in an optionally buffered, aqueous solution or 2) dissolved and/or dispersed in an adhesive or 3) dispersed in a polymer. A suitable concentration of the active compound is about 1% to 25%, preferably about 3% to 15%. As one particular possibility, the active compound may be delivered from the patch by electrotransport or iontophoresis as generally described in Pharmaceutical Research 3 (6), 318 (1986).

Pharmaceutical compositions of the present invention suitable for oral administration may be presented as discrete units such as capsules, caplets, cachets or tablets each containing a predetermined amount of the active ingredients; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredients in a free-flowing form such as a powder or granules, optionally mixed with a binder (e.g. povidone, gelatin, hydroxypropylmethyl cellulose), lubricant, inert diluent, preservative, disintegrant (e.g. sodium starch glycollate, cross-linked povidone, cross-linked sodium carboxymethyl cellulose) surface-active or dispersing agent. Molded tablets may be made by molding a mixture of the powdered compound moistened with an inert liquid diluent in a suitable machine. The tablets may optionally be coated or scored and may be formulated so as to provide slow or controlled release of the active ingredients therein using, for example, hydroxypropylmethyl cellulose in varying proportions to provide the desired release profile. Tablets may optionally be provided with an enteric coating, to provide release in parts of the gut other than the stomach.

Pharmaceutical compositions suitable for topical administration in the mouth include lozenges comprising the active ingredients in a flavored base, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions suitable for vaginal administration may be presented as pessaries, tampons, creams, gels, pastes, foams or spray Pharmaceutical compositions containing in addition to the active ingredient such carriers as are known in the art to be appropriate.

Pharmaceutical compositions for rectal administration may be presented as a suppository with a suitable carrier comprising, for example, cocoa butter or a salicylate or other materials commonly used in the art. The suppositories may be conveniently formed by admixture of the active combination with the softened or melted carrier(s) followed by chilling and shaping in molds.

Pharmaceutical compositions suitable for parenteral administration include aqueous and non-aqueous isotonic sterile injection solutions which may contain anti-oxidants, buffers, bacteriostats and solutes which render the pharmaceutical composition isotonic with the blood of the intended recipient; and aqueous and non-aqueous sterile suspensions which may include suspending agents and thickening agents; and liposomes or other microparticulate systems which are designed to target the compound to blood components or one or more organs. The pharmaceutical compositions may be presented in unit-dose or multi-dose sealed containers, for example, ampoules and vials, and may be stored in a freeze-dried (lyophilized) condition requiring only the addition of the sterile liquid carrier, for example water for injection, immediately prior to use. Extemporaneous injection solutions and suspensions may be prepared from sterile powders, granules and tablets of the kind previously described.

Unit dosage pharmaceutical compositions include those containing a daily dose or daily subdose of the active ingredients, as hereinbefore recited, or an appropriate fraction thereof.

It should be understood that in addition to the ingredients particularly mentioned above the pharmaceutical compositions of this invention may include other agents conventional in the art having regard to the type of pharmaceutical composition in question, for example, those suitable for oral administration may include such further agents as sweeteners, thickeners and flavoring agents.

EXAMPLES

The following examples are intended for illustration only and are not intended to limit the scope of the invention in any way.

Low resolution, open-access LC-MS data were acquired in either ESI pos/neg or APCI pos/neg mode with scanning from 100-1100 amu@ 0.5 sec/scan. LC conditions: flowrate 0.8 mL/min. 85% H2O (0.1% formic acid) to 100% MeOH (0.075% formic acid) in 6 minutes. Phenomenex Max-RP column, 2.0×50 mm.

High Resolution Mass Spectra were acquired using Micromass LCT mass spectrometer (time-of-flight) with flow injection (FIA-MS) at 0.3 mL/min with 100% MeOH (0.1% formic acid), run time of 2 minutes, in ESI+ mode, scanning from 100-1100 amu@ 0.5 sec/scan. Reserpine was used as the lock mass (m/z 609.2812) and to adjust mass scale.

As will be appreciated by those skilled in the art, the following scheme may be followed in preparing the compounds of the present invention. The variability depicted within the scheme(s) illustrated herein, for example the variability for the substituent labeled R1, should be limited to the particular scheme and not necessarily extended throughout the rest of the present specification.

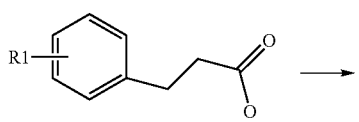

indane m = x = 1
tetralin m = x = 2
cyclobutylbenzyl m = 0

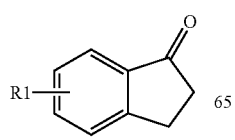

-continued

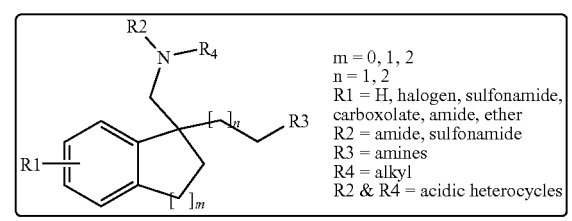

m = 0, 1, 2
n = 1, 2
R1 = H, halogen, sulfonamide, carboxolate, amide, ether
R2 = amide, sulfonamide
R3 = amines
R4 = alkyl
R2 & R4 = acidic heterocycles

LDA (0.1 eq)
diethylcyano-phosphonate (1.1 eq)
THF -10° C. to RT

1

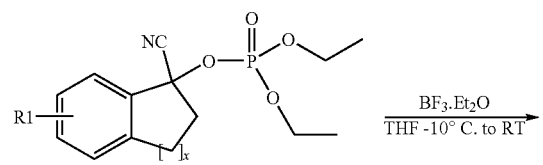

BF$_3$.Et$_2$O
THF -10° C. to RT

2

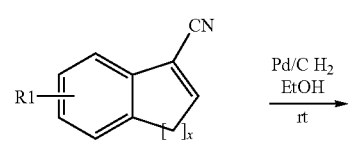

Pd/C H$_2$
EtOH
rt

3

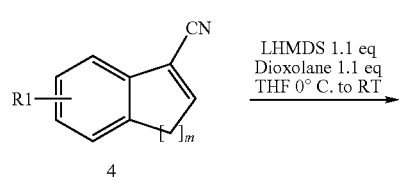

LHMDS 1.1 eq
Dioxolane 1.1 eq
THF 0° C. to RT

4

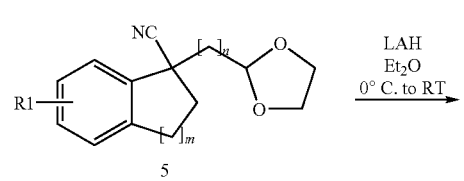

LAH
Et$_2$O
0° C. to RT

5

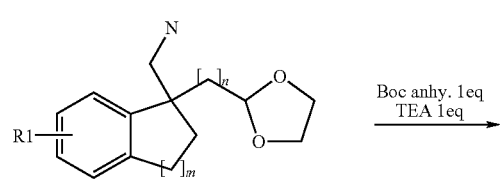

Boc anhy. 1eq
TEA 1eq

6

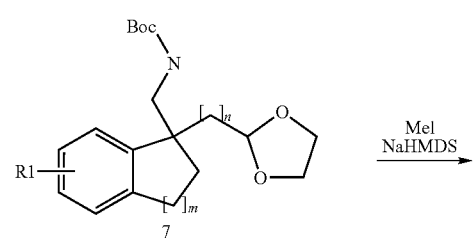

MeI
NaHMDS

7

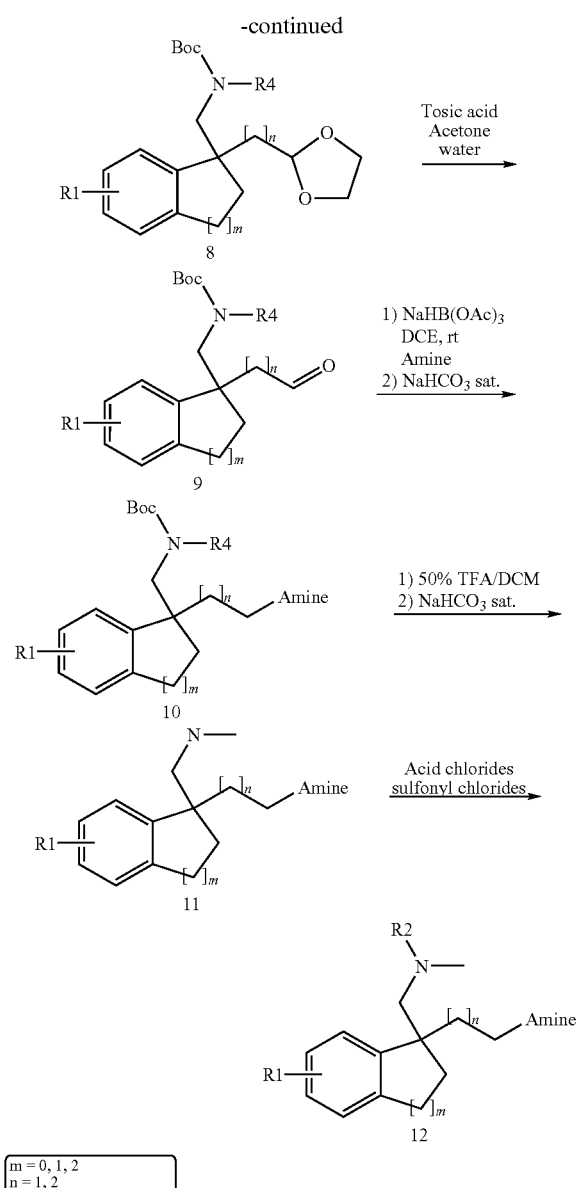

```
m = 0, 1, 2
n = 1, 2
R1 = H, Cl
R2 = amide, sulfonamide
```

Scheme 1 illustrates the methods used to make the cyclobutylbenzyl, indane, and tetralin scaffolds and final products. Starting from a fused ring precursor, in the case of indane, and tetralin the synthesis starts at the commercially available indanone and tetralone respectively, while the bicyclo[4.2.0]octa-1,3,5-triene-7-carbonitrile was commercially available and allowed the cyclobutylbenzyl synthesis to start at the saturated nitrile stage. The following description will focus on the indane scaffold though all three scaffolds are made in the same fashion from their respective starting points.

Indanone 1 is reacted with diethylcyanophosphonate and a catalytic amount of lithium diisopropylamide to afford the cyanophosphonate 2. The unsaturated nitrile 3 is then formed by the addition of borontrifluoride diethyletherate to 2, which will eliminate the phosphonate group. Unsaturated nitrile 3 is then hydrogenated with palladium on carbon to afford the saturated nitrile 4. Alkylation of nitrile 4 with 2-bromomethyl-1,3-dioxolane by the slow addition of lithium bis(trimethylsilyl)amide affords the 1-methyl-1,3-dioxolane substituted nitrile 5. Lithium aluminum hydride is added to 5 to reduce the nitrile to methylamine 6, followed by protection of the amine with di-tert-butyl dicarbonate to afford 7. To obtain 8 a solution of 7 with Methyl Iodide was treated with sodium bis(trimethylsilyl)amide. Deprotection of the dioxalane group on 8 with tosic acid in acetone and water afforded the aldehyde 9. Array chemistry was then used to make several compounds through a reductive amination of 9 with secondary amines to give compounds of structure 10. Following deprotection of the tert-butyl carbamate with trifluoroacetic acid yielding secondary amines of structure 11, they were acylated or sulfonylated to give the final products of general structure 12. Additionally, the following specific compounds were prepared to demonstrate the above general scheme:

Example 1

1H-indene-3-carbonitrile

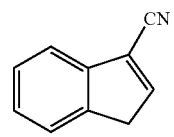

A solution of 1-indanone (100 g, 0.756 mole) in 1 L of dry THF was cooled to −10° C. followed by the addition of 38.7 ml of 2M LDA (75.6 mmole). After 20 min of stirring at −10° C. diethyl cyanophosphonate (126.28 ml, 0.8323 moles) was added over 1 hour. The reaction was warmed to room temperature until no indanone was visible by TLC. The reaction was again cooled to −10° C. and borotrifluoride diethyl etherate (191 ml, 1.513 moles) was added dropwise. After warming to room temperature THF was evaporated and the resulting dark oil dissolved in EtOAc, washed with water and dried over MgSO$_4$. Evaporation of the EtOAc and distillation of the resulting oil afforded 88.4908 g of 1H-indene-3-carbonitrile (83% yield).

1H NMR (400 MHz, DMSO-D6) δ ppm 3.7 (m, 2H) 7.3 (m, 1H) 7.4 (m, 1H) 7.5 (m, 1H) 7.5 (d, J=7.2 Hz, 1H) 7.6 (t, J=2.1 Hz, 1H).

Example 2

3,4-dihydro-1-naphthalenecarbonitrile

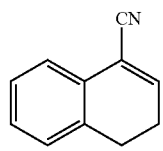

Starting from α-tetralone (50.00 g, 0.342 mole) and using the procedure described in Example 1, 41.6512 g of 3,4-dihydro-1-naphthalenecarbonitrile (78% yield) was afforded.

1H NMR (400 MHz, DMSO-D6) δ ppm 2.4 (td, J=8.2, 4.8 Hz, 2H) 2.8 (t, J=8.2 Hz, 2H) 7.1 (t, J=4.8 Hz, 1H) 7.2 (m, 1H) 7.3 (m, 3H).

Example 3

6-chloro-1H-indene-3-carbonitrile

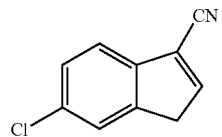

Starting from 6-chloro-1-indanone (25.56 g, 0.1534 mole) and using the procedure described in Example 1, 20.2540 g of 6-chloro-1H-indene-3-carbonitrile (75% yield) was afforded.

1H NMR (300 MHz, DMSO-D6) δ ppm 3.8 (s, 2H) 7.5 (m, 2H) 7.7 (s, 1H) 7.7 (t, J=1.9 Hz, 1H).

Example 4

1-indanecarbonitrile

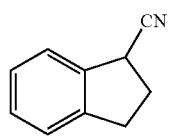

A suspension of 5% Pd on carbon in a solution of 1H-indene-3-carbonitrile in EtOH (200 ml) was placed under an atmosphere of hydrogen with vigorous stirring overnight. After removal of excess hydrogen from the reaction the solution as filtered through celite and concentrated to an oil. The resulting oil was re-dissolved in EtOH and filtered a second time to remove the remaining carbon and catalyst. Evaporation of solvent afforded 12.0108 g of 1-indanecarbonitrile (95% yield) as an oil.

1H NMR (400 MHz, DMSO-D6) δ ppm 2.2 (m, 1H) 2.5 (m, 1H) 2.9 (m, 1H) 3.0 (m, 1H) 4.4 (t, J=8.0 Hz, 1H) 7.2 (m, 2H) 7.3 (m, 1H) 7.4 (m, J=7.7, 4.9 Hz, 1H).

Example 5

1,2,3,4-tetrahydro-1-naphthalenecarbonitrile

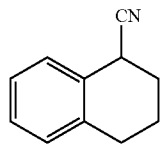

3,4-dihydro-1-naphthalenecarbonitrile (41.65 g, 0.2684 mole) was hydrogenated according to the procedure described in Example 4 to afford 41.78 g of 1,2,3,4-tetrahydro-1-naphthalenecarbonitrile (99% yield).

1H NMR (400 MHz, DMSO-D6) δ ppm 1.1 (m, 2H) 1.5 (d, 2H) 1.9 (m, 1H) 2.5 (m, 2H) 7.6 (d, J=8.1 Hz, 1H) 7.7 (d, J=8.8 Hz, 1H) 7.7 (d, J=8.8 Hz, 1H) 8.0 (d, J=1.7 Hz, 1H).

Example 6

5-chloro-1-indanecarbonitrile

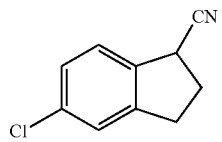

6-chloro-1H-indene-3-carbonitrile (20.25 g, 0.1153 mole) was hydrogenated according to the procedure described in Example 4 to afford 8.5 g of 5-chloro-1-indanecarbonitrile (61% yield).

1H NMR (400 MHz, DMSO-D6) δ ppm 2.2 (m, 1H) 2.5 (m, 1H) 2.9 (m, 1H) 3.0 (m, 1H) 4.4 (t, J=7.9 Hz, 1H) 7.3 (m, 2H) 7.4 (m, 1H).

Example 7

1-(1,3-dioxolan-2-ylmethyl)-1-indanecarbonitrile

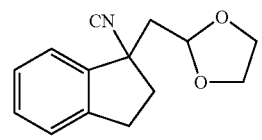

2-bromomethyl-1,3-dioxolane (12.94 ml, 125.0 mmole) was added to a solution of 1-indanecarbonitrile (16.27 g, 113.6 mmole) in 100 ml of THF and cooled to 0° C. After the dropwise addition of 1M LHMDS (125 ml) the solution was stirred at 0° C. for 20 min then at room temperature for 20 min. After the removal of solvent the residue was flashed of silica using 15% EtOAc and Hexanes to afford 19.23 g of 1-(1,3-dioxolan-2-ylmethyl)-1-indanecarbonitrile (74% yield) as a thick oil.

1H NMR (300 MHz, DMSO-D6) δ ppm 2.0 (dd, J=14.3, 5.8 Hz, 1H) 2.5 (m, 3H) 3.0 (t, J=7.2 Hz, 2H) 3.8 (m, 2H) 3.9 (m, 2H) 5.0 (m, 1H) 7.3 (m, 3H) 7.5 (m, 1H).

Example 8

7-(1,3-dioxolan-2-ylmethyl)bicyclo[4.2.0]octa-1,3,5-triene-7-carbonitrile

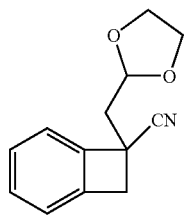

Using the commercially available bicyclo[4.2.0]octa-1,3,5-triene-7-carbonitrile and the method described in Example 7 7-(1,3-dioxolan-2-ylmethyl)bicyclo[4.2.0]octa-1,3,5-triene-7-carbonitrile was afforded.

1H NMR (400 MHz, DMSO-D6) δ ppm 2.3 (m, J=24.8, 14.3, 4.7 Hz, 2H) 3.5 (m, J=9.2, 5.3 Hz, 1H) 3.7 (m, 1H) 3.8 (m, 2H) 3.9 (m, 2H) 5.1 (t, J=4.8 Hz, 1H) 7.2 (m, J=6.9 Hz, 1H) 7.3 (m, 3H).

Example 9

1-(1,3-dioxolan-2-ylmethyl)-1,2,3,4-tetrahydro-1-naphthalenecarbonitrile

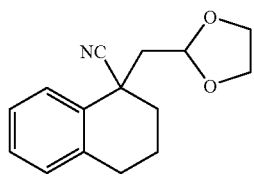

Utilizing the procedure from Example 7 and the product obtained in Example 5,1-(1,3-dioxolan-2-ylmethyl)-1,2,3,4-tetrahydro-1-naphthalenecarbonitrile was afforded.

$^1$H-NMR (300 MHz, DMSO-d$_6$) δ 7.57-7.54 (m, 1H), 7.30-7.25 (m, 2H), 7.21-7.18 (m, 1H), 5.02-4.99 (m, 1H), 4.00-3.91 (m, 2H), 3.89-3.81 (m, 2H), 2.83-2.79 (m, 2H), 2.55-2.41 (m, 1H), 2.39-2.20 (m, 3H), 2.03-1.78 (m, 2H).

Example 10

1-[2-(1,3-dioxolan-2-yl)ethyl]-1-indanecarbonitrile

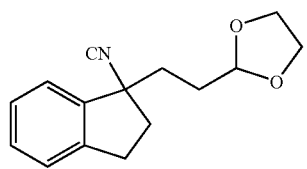

2(2-bromoethyl)-1,3-dioxolane (14.09 ml, 120.1 mmole) was added to a solution of 1-indanecarbonitrile (15.63 g, 109.2 mmole) in 100 ml of THF and cooled to 0° C. After the dropwise addition of 1M LHMDS (120 ml) the solution was stirred at 0° C. for 20 min then at room temperature for 20 min. After the removal of solvent the residue was flashed of silica using 15% EtOAc and Hexanes to afford 1-[2-(1,3-dioxolan-2-yl)ethyl]-1-indanecarbonitrile as a thick oil.

1H NMR (300 MHz, CHLOROFORM-D) δ ppm 1.9 (m, 3H) 2.1 (m, 1H) 2.3 (m, 1H) 2.6 (m, 1H) 3.0 (m, 2H) 3.9 (m, 2H) 4.0 (m, 2H) 4.9 (t, J=4.1 Hz, 1H) 7.3 (m, 3H) 7.4 (m, 1H).

Example 11

7-[2-(1,3-dioxolan-2-yl)ethyl]bicyclo[4.2.0]octa-1,3,5-triene-7-carbonitrile

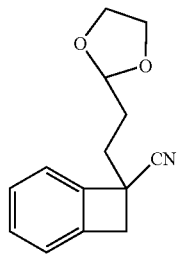

Using the commercially available bicyclo[4.2.0]octa-1,3,5-triene-7-carbonitrile and the method described in Example 107-[2-(1,3-dioxolan-2-yl)ethyl]bicyclo[4.2.0]octa-1,3,5-triene-7-carbonitrile was afforded.

1H NMR (400 MHz, DMSO-D6) δ ppm 1.8 (m, 2H) 2.0 (m, 2H) 3.4 (d, J=14.3 Hz, 1H) 3.7 (d, J=14.3 Hz, 1H) 3.8 (m, 2H) 3.9 (m, 2H) 4.9 (t, J=4.4 Hz, 1H) 7.2 (m, 1H) 7.3 (m, 3H).

Example 12

1-[2-(1,3-dioxolan-2-yl)ethyl]-1,2,3,4-tetrahydro-1-naphthalenecarbonitrile

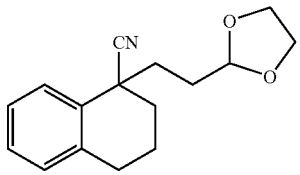

Utilizing the procedure from Example 10 and the product obtained in Example 5, 1-[2-(1,3-dioxolan-2-yl)ethyl]-1,2,3,4-tetrahydro-1-naphthalenecarbonitrile was afforded. 1H NMR (300 MHz, DMSO-D6) δ ppm 2.0 (m, 7H) 2.8 (d, J=6.1 Hz, 2H) 3.4 (s, 1H) 3.8 (m, 2H) 3.9 (m, 2H) 4.9 (t, J=4.6 Hz, 1H) 7.3 (m, 3H) 7.5 (m, J=6.5, 2.6 Hz, 1H).

Example 13

5-chloro-1-[2-(1,3-dioxolan-2-yl)ethyl]-1-indanecarbonitrile

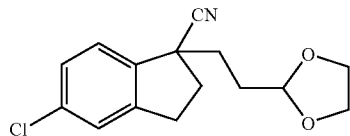

5-chloro-1-indanecarbonitrile (3.55 g, 0.0199 mole) was alkylated according to the procedure described in example U16370/169/1 to afford 3.65 g of 5-chloro-1-[2-(1,3-dioxolan-2-yl)ethyl]-1-indanecarbonitrile (66% yield).

1H NMR (400 MHz, DMSO-D6) δ ppm 1.7 (m, 2H) 2.0 (m, 1H) 2.3 (m, 1H) 2.5 (m, 1H) 3.0 (t, J=7.1 Hz, 2H) 3.7 (m, 2H) 3.8 (m, 2H) 4.8 (t, J=4.2 Hz, 1H) 7.3 (dd, J=8.1, 2.1 Hz, 1H) 7.4 (m, 2H).

Example 14

[1-(1,3-dioxolan-2-ylmethyl)-2,3-dihydro-1H-inden-1-yl]methanamine

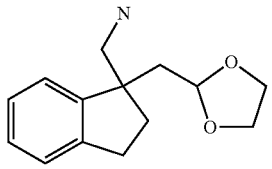

A 1M solution of lithium aluminum hydride in Et$_2$O was added dropwise to a solution of 1-(1,3-dioxolan-2-ylmethyl)-1-indanecarbonitrile (9.9376 g, 43.343 mmole) in Et$_2$O at 0° C. After warming to room temperature overnight the reaction was quenched by the dropwise addition of water resulting in a fine white precipitate. The solid was filtered of and washed 4 times with 100 ml of Et$_2$O. The combined ether layers were evaporated to afford 8.1770 g of [1-(1,3-dioxolan-2-ylmethyl)-2,3-dihydro-1H-inden-1-yl]methanamine (81% yield) as an oil.

1H NMR (400 MHz, DMSO-D6) δ ppm 1.8 (dd, J=14.3, 3.8 Hz, 1H) 1.9 (m, J=13.0, 7.3 Hz, 1H) 2.0 (d, J=5.9 Hz, 1H) 2.0 (m, 1H) 2.6 (m, 2H) 2.8 (t, J=7.5 Hz, 2H) 3.6 (m, 2H) 3.8 (m, 2H) 4.6 (dd, J=5.8, 3.7 Hz, 1H) 7.1 (m, 4H).

Example 15

[7-(1,3-dioxolan-2-ylmethyl)bicyclo[4.2.0]octa-1,3,5-trien-7-yl]methanamine

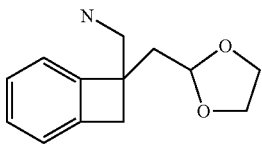

Utilizing the procedure from Example 14 and the product obtained in Example 8, [7-(1,3-dioxolan-2-ylmethyl)bicyclo[4.2.0]octa-1,3,5-trien-7-yl]methanamine was afforded in 79% yield.

1H NMR (400 MHz, DMSO-D6) δ ppm 2.0 (m, 2H) 2.8 (s, 2H) 2.9 (m, 2H) 3.7 (m, 2H) 3.8 (m, 2H) 4.8 (t, J=4.9 Hz, 1H) 7.1 (d, J=6.7 Hz, 1H) 7.1 (m, 3H).

Example 16

[1-(1,3-dioxolan-2-ylmethyl)-1,2,3,4-tetrahydro-1-naphthalenyl]methanamine

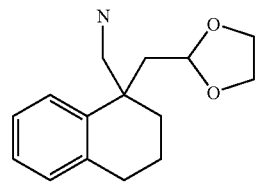

Utilizing the procedure from Example 14 and the product obtained in Example 9, [1-(1,3-dioxolan-2-ylmethyl)-1,2,3,4-tetrahydro-1-naphthalenyl]methanamine was afforded.

$^1$H-NMR (300 MHz, DMSO-d$_6$) δ 7.32-7.29 (m, 1H), 7.17-7.08 (m, 3H), 4.57-4.54 (m, 1H), 3.91-3.81 (m, 2H), 3.79-3.61 (m, 2H), 2.81-2.60 (m, 4H), 2.22-1.70 (m, 6H). ES-LCMS m/z 248 (M+H)$^+$.

Example 17

{1-[2-(1,3-dioxolan-2-yl)ethyl]-2,3-dihydro-1H-inden-1-yl}methanamine

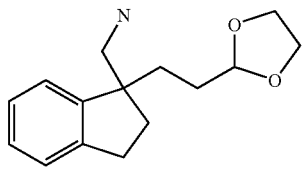

Utilizing the procedure from Example 14 and the product obtained in Example 10, {1-[2-(1,3-dioxolan-2-yl)ethyl]-2,3-dihydro-1H-inden-1-yl}methanamine was afforded in 92% yield.

1H NMR (400 MHz, CHLOROFORM-D) δ ppm 1.5 (m, 1H) 1.6 (m, 1H) 1.7 (m, 2H) 2.0 (m, 2H) 2.7 (d, J=13.1 Hz, 1H) 2.8 (m, 1H) 2.9 (t, J=7.7 Hz, 2H) 3.8 (m, 2H) 3.9 (m, 2H) 4.8 (t, J=4.6 Hz, 1H) 7.1 (m, 4H).

Example 18

{7-[2-(1,3-dioxolan-2-yl)ethyl]bicyclo[4.2.0]octa-1,3,5-trien-7-yl}methanamine

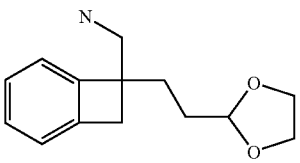

Utilizing the procedure from Example 14 and the product obtained in Example 11, {7-[2-(1,3-dioxolan-2-yl)ethyl]bicyclo[4.2.0]octa-1,3,5-trien-7-yl}methanamine was afforded in 91% yield.

1H NMR (400 MHz, DMSO-D6) δ ppm 1.5 (m, 2H) 1.7 (m, 1H) 1.8 (m, 1H) 2.7 (s, 2H) 2.8 (m, 1H) 2.9 (m, 1H) 3.7 (m, 2H) 3.8 (m, 2H) 4.7 (t, J=4.7 Hz, 1H) 7.1 (m, 4H).

Example 19

{1-[2-(1,3-dioxolan-2-yl)ethyl]-1,2,3,4-tetrahydro-1-naphthalenyl}methanamine

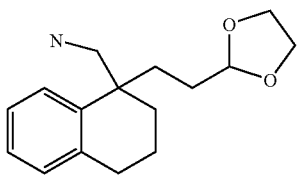

Utilizing the procedure from Example 14 and the product obtained in Example 12, {1-[2-(1,3-dioxolan-2-yl)ethyl]-1,2,3,4-tetrahydro-1-naphthalenyl}methanamine was afforded.

1H NMR (300 MHz, DMSO-D6) δ ppm 1.2 (m, 1H) 1.5 (m, 4H) 1.7 (m, 3H) 1.9 (s, 1H) 2.7 (t, J=6.1 Hz, 2H) 2.8 (d, J=13.0 Hz, 1H) 3.4 (m, 2H) 3.8 (m, 2H) 3.8 (dd, J=4.3, 2.3 Hz, 2H) 4.7 (t, J=4.7 Hz, 1H) 7.1 (m, 3H) 7.2 (m, 1H).

Example 20

{5-chloro-1-[2-(1,3-dioxolan-2-yl)ethyl]-2,3-dihydro-1H-inden-1-yl}methanamine

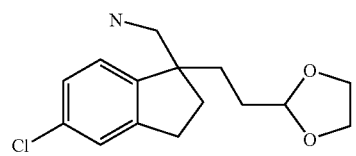

Utilizing the procedure from Example 14 and the product obtained in Example 13, {5-chloro-1-[2-(1,3-dioxolan-2-yl)ethyl]-2,3-dihydro-1H-inden-1-yl}methanamine was afforded in 87% yield.

1H NMR (400 MHz, DMSO-D6) δ ppm 1.2 (s, 1H) 1.2 (m, J=17.2, 8.5, 4.3, 4.2 Hz, 2H) 1.4 (m, 1H) 1.5 (td, J=12.7, 4.0 Hz, 1H) 1.7 (td, J=12.9, 4.5 Hz, 1H) 1.8 (ddd, J=12.9, 8.6, 7.1 Hz, 1H) 2.0 (ddd, J=13.0, 8.4, 6.1 Hz, 1H) 2.6 (m, 2H) 2.8 (m, 2H) 3.7 (m, 2H) 3.8 (m, 2H) 4.7 (t, J=4.8 Hz, 1H) 7.1 (d, J=8.1 Hz, 1H) 7.2 (m, 1H) 7.2 (d, J=1.6 Hz, 1H).

Example 21 tert-butyl [1-(1,3-dioxolan-2-ylmethyl)-2,3-dihydro-1H-inden-1-yl]methylcarbamate

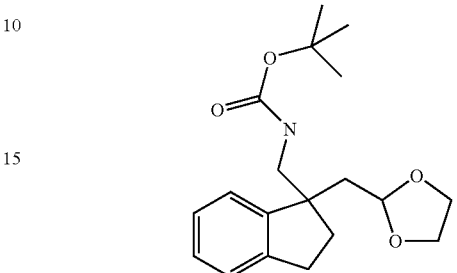

Boc anhydride (8.49 g, 38.9 mmole) was added to a solution of [1-(1,3-dioxolan-2-ylmethyl)-2,3-dihydro-1H-inden-1-yl]methanamine (9.08 g, 38.9 mmole) and triethylamine (10.8 ml, 77.8 mmole) in 100 ml of THF. After stirring for 1 hour at room temperature the solvent was evaporated and the residue dissolved in Et$_2$O and washed with water and saturated NaCl solution. After evaporation of the ether 13.53 g of tert-butyl [1-(1,3-dioxolan-2-ylmethyl)-2,3-dihydro-1H-inden-1-yl]methylcarbamate was obtained as a crude oil and used with no further purification.

1H NMR (400 MHz, DMSO-D6) δ ppm 1.3 (s, 3H) 1.9 (m, 4H) 2.7 (m, 2H) 3.0 (m, 2H) 3.6 (m, 2H) 3.7 (m, 2H) 4.4 (m, 1H) 6.6 (m, 1H) 7.1 (m, 3H) 7.2 (m, 1H).

Example 22 tert-butyl [7-(1,3-dioxolan-2-ylmethyl)bicyclo[4.2.0]octa-1,3,5-trien-7-yl]methylcarbamate

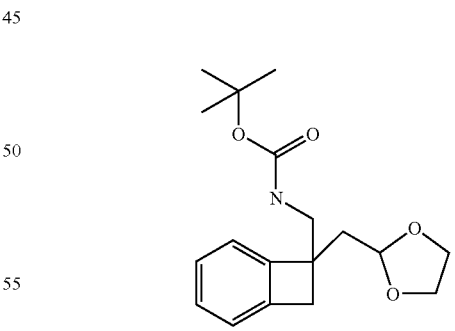

Utilizing the procedure from Example 21 and the product obtained in Example 15, tert-butyl [7-(1,3-dioxolan-2-ylmethyl)bicyclo[4.2.0]octa-1,3,5-trien-7-yl]methylcarbamate was afforded.

1H NMR (400 MHz, DMSO-D6) δ ppm 1.3 (m, 9H) 1.9 (m, J=14.4, 5.6 Hz, 1H) 2.0 (m, 1H) 3.0 (m, 2H) 3.3 (m, 2H) 3.7 (m, 2H) 3.8 (m, 2H) 4.8 (t, 1H) 6.9 (t, J=6.1 Hz, 1H) 7.1 (m, 4H).

Example 23 tert-butyl [1-(1,3-dioxolan-2-ylmethyl)-1,2,3,4-tetrahydro-1-naphthalenyl]methylcarbamate

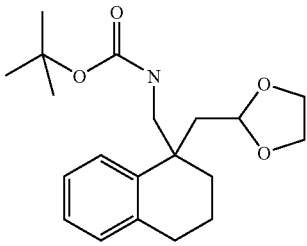

Utilizing the procedure from example U16370/184/1 and the product obtained in example U17436-50-1, tert-butyl [1-(1,3-dioxolan-2-ylmethyl)-1,2,3,4-tetrahydro-1-naphthalenyl]methylcarbamate was afforded.

¹H-NMR (300 MHz, CDCl₃) δ 7.32-7.22 (m, 1H), 7.19-7.12 (m, 3H), 4.80-4.77 (m, 1H), 4.63 (br s, 1H), 4.08-3.91 (m, 2H), 3.88-3.72 (m, 2H), 3.58-3.43 (m, 2H), 2.90-2.75 (m, 2H), 2.25-1.80 (m, 6H), 1.45 (s, 9H). ES-LCMS m/z 248 (M-Boc+H)⁺.

Example 24 tert-butyl {1-[2-(1,3-dioxolan-2-yl)ethyl]-2,3-dihydro-1H-inden-1-yl}methylcarbamate

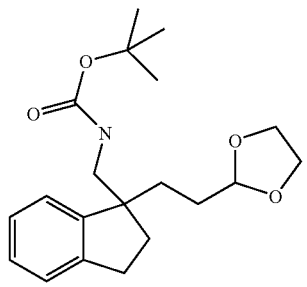

Utilizing the procedure from Example 21 and the product obtained in Example 17, tert-butyl {1-[2-(1,3-dioxolan-2-yl)ethyl]-2,3-dihydro-1H-inden-1-yl}methylcarbamate was afforded.

1H NMR (400 MHz, DMSO-D6) δ ppm 1.3 (s, 9H) 1.4 (m, 1H) 1.4 (s, 2H) 1.6 (m, 1H) 1.7 (m, 1H) 1.9 (m, 1H) 2.8 (m, 2H) 3.0 (dd, J=13.6, 6.0 Hz, 1H) 3.1 (m, 1H) 3.7 (m, 2H) 3.8 (m, 2H) 4.6 (t, J=4.7 Hz, 1H) 6.7 (t, J=6.2 Hz, 1H) 7.1 (m, 4H).

Example 25 tert-butyl {7-[2-(1,3-dioxolan-2-yl)ethyl]bicyclo[4.2.0]octa-1,3,5-trien-7-yl}methylcarbamate

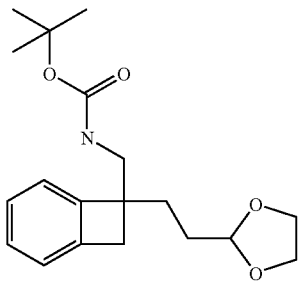

Utilizing the procedure from Example 21 and the product obtained in Example 18, tert-butyl {7-[2-(1,3-dioxolan-2-yl)ethyl]bicyclo[4.2.0]octa-1,3,5-trien-7-yl}methylcarbamate was afforded.

1H NMR (400 MHz, DMSO-D6) δ ppm 1.3 (s, 9H) 1.6 (m, 2H) 1.7 (m, 1H) 2.7 (d, J=14.1 Hz, 1H) 3.0 (d, J=14.3 Hz, 1H) 3.1 (dd, J=13.7, 5.9 Hz, 1H) 3.3 (m, 1H) 3.3 (s, 2H) 3.7 (m, 2H) 3.8 (m, 2H) 4.7 (t, J=4.2 Hz, 1H) 7.0 (m, 1H) 7.1 (m, 3H).

Example 26 tert-butyl {1-[2-(1,3-dioxolan-2-yl)ethyl]-1,2,3,4-tetrahydro-1-naphthalenyl}methylcarbamate

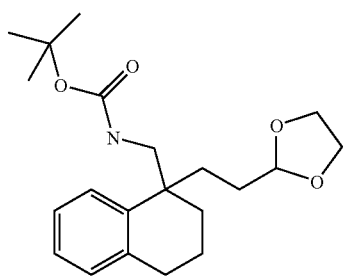

Utilizing the procedure from Example 21 and the product obtained in Example 19, tert-butyl {1-[2-(1,3-dioxolan-2-yl)ethyl]-1,2,3,4-tetrahydro-1-naphthalenyl}methylcarbamate was afforded.

1H NMR (300 MHz, CHLOROFORM-D) δ ppm 1.5 (s, 9H) 1.6 (m, 4H) 1.8 (m, 4H) 2.8 (d, J=6.1 Hz, 2H) 3.4 (m, 2H) 3.9 (m, 2H) 4.0 (m, 2H) 4.4 (s, 1H) 4.8 (t, J=4.6 Hz, 1H) 7.2 (m, 3H) 7.3 (m, 1H).

Example 27 tert-butyl {5-chloro-1-[2-(1,3-dioxolan-2-yl)ethyl]-2,3-dihydro-1H-inden-1-yl}methylcarbamate

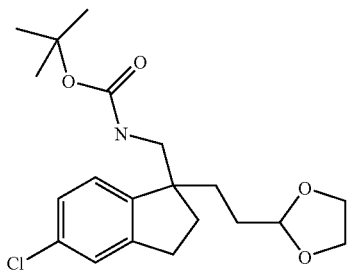

Utilizing the procedure from Example 21 and the product obtained in Example 20, tert-butyl {5-chloro-1-[2-(1,3-dioxolan-2-yl)ethyl]-2,3-dihydro-1H-inden-1-yl}methylcarbamate was afforded in quantity yield.

1H NMR (400 MHz, DMSO-D6) δ ppm 1.3 (m, 1H) 1.3 (m, 9H) 1.4 (m, 1H) 1.6 (m, 2H) 1.8 (m, 1H) 2.0 (m, 1H) 2.8 (m, 2H) 3.0 (m, J=13.6, 6.1 Hz, 1H) 3.1 (m, 1H) 3.7 (m, 2H) 3.8 (m, 2H) 4.7 (t, J=4.6 Hz, 1H) 6.8 (t, J=6.2 Hz, 1H) 7.0 (d, J=8.1 Hz, 1H) 7.1 (m, J=8.1 Hz, 1H) 7.2 (s, 1H).

Example 28 tert-butyl [1-(1,3-dioxolan-2-ylmethyl)-2,3-dihydro-1H-inden-1-yl]methyl(methyl)carbamate

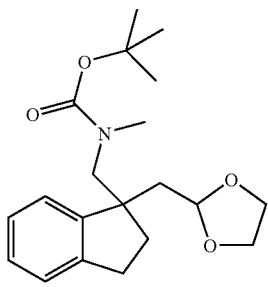

A solution of tert-butyl [1-(1,3-dioxolan-2-ylmethyl)-2,3-dihydro-1H-inden-1-yl]methylcarbamate (13.50 g, 38.9 mmole) in THF was cooled to 0° C. To this was added iodomethane (7.27 ml, 117 mmole) followed by 1M NaHMDS in THF (58 ml, 58 mmole). The reaction was then warmed to room temperature and stirred until no U16370/185/2 remained by TLC. The THF was evaporated and the residue dissolved in Et₂O. The ether was washed with water and evaporated to afford 14.33 g of tert-butyl [1-(1,3-dioxolan-2-ylmethyl)-2,3-dihydro-1H-inden-1-yl]methyl(methyl)carbamate as a crude oil, which was used, with no further purification.

1H NMR (400 MHz, CHLOROFORM-D) δ ppm 1.4 (m, 9H) 2.2 (m, J=5.0 Hz, 2H) 2.2 (m, 3H) 2.6 (s, 3H) 3.0 (m, 2H) 3.2 (m, 1H) 3.8 (m, 2H) 4.0 (m, 2H) 4.8 (d, J=4.5 Hz, 1H) 7.2 (m, 4H).

Example 29 tert-butyl [7-(1,3-dioxolan-2-ylmethyl)bicyclo[4.2.0]octa-1,3,5-trien-7-yl]methyl(methyl)carbamate

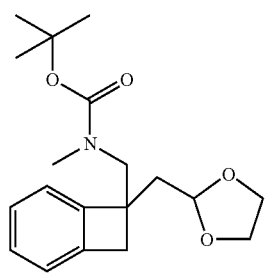

Utilizing the procedure from Example 28 and the product obtained in Example 22, tert-butyl [7-(1,3-dioxolan-2-ylmethyl)bicyclo[4.2.0]octa-1,3,5-trien-7-yl]methyl(methyl)carbamate was afforded.

1H NMR (400 MHz, DMSO-D6) δ ppm 1.3 (m, 9H) 2.0 (m, 2H) 2.6 (s, 3H) 3.1 (m, J=10.3 Hz, 1H) 3.5 (m, 1H) 3.5 (m, 1H) 3.7 (m, 3H) 3.8 (m, 2H) 4.8 (m, 1H) 7.1 (m, J=6.4, 6.4 Hz, 1H) 7.1 (m, 3H).

Example 30 tert-butyl [1-(1,3-dioxolan-2-ylmethyl)-1,2,3,4-tetrahydro-1-naphthalenyl]methyl(methyl)carbamate

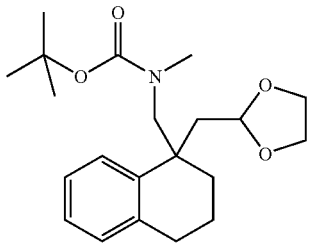

Utilizing the procedure from Example 28 and the product obtained in Example 23, tert-butyl [1-(1,3-dioxolan-2-ylmethyl)-1,2,3,4-tetrahydro-1-naphthalenyl]methyl(methyl)carbamate was afforded.

¹H-NMR (300 MHz, CDCl₃) δ 7.38-7.22 (m, 1H), 7.19-7.12 (m, 3H), 4.58 (br s, 1H), 3.98-3.82 (m, 2H), 3.79-3.64 (m, 2H), 3.33 (br m, 1H), 2.79 (br s, 3H), 2.70 (s, 1H), 2.60 (br s, 1H), 2.46-2.41 (m, 1H), 2.08-1.85 (m, 5H), 1.70-1.60 (m, 1H), 1.43 (s, 9H). ES-LCMS m/z 384 (M+Na)⁺.

Example 31 tert-butyl {1-[2-(1,3-dioxolan-2-yl)ethyl]-2,3-dihydro-1H-inden-1-yl}methyl(methyl)carbamate

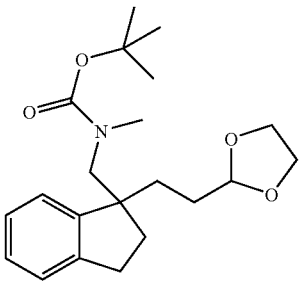

Utilizing the procedure from Example 28 and the product obtained in Example 24, tert-butyl {1-[2-(1,3-dioxolan-2-yl)ethyl]-2,3-dihydro-1H-inden-1-yl}methyl(methyl)carbamate was afforded.

1H NMR (400 MHz, CHLOROFORM-D) δ ppm 1.4 (m, 9H) 1.5 (m, 1H) 1.6 (m, 1H) 1.8 (m, 2H) 1.9 (m, 1H) 2.1 (m, 1H) 2.5 (m, J=57.2 Hz, 3H) 2.8 (m, 2H) 3.0 (m, 1H) 3.7 (m, 1H) 3.8 (m, 2H) 3.9 (m, 2H) 4.8 (m, 1H) 7.1 (m, 4H).

Example 32 tert-butyl {7-[2-(1,3-dioxolan-2-yl)ethyl]bicyclo[4.2.0]octa-1,3,5-trien-7-yl}methyl(methyl)carbamate

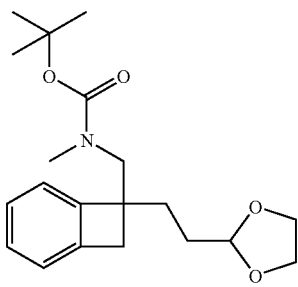

Utilizing the procedure from Example 28 and the product obtained in Example 25, tert-butyl {7-[2-(1,3-dioxolan-2-yl)ethyl]bicyclo[4.2.0]octa-1,3,5-trien-7-yl}methyl(methyl)carbamate was afforded.

1H NMR (400 MHz, DMSO-D6) δ ppm 1.4 (m, 9H) 1.6 (m, 3H) 1.7 (m, 1H) 2.7 (s, 3H) 2.8 (m, J=10.3 Hz, 1H) 3.1 (m, 1H) 3.4 (m, 1H) 3.6 (m, 1H) 3.7 (m, 2H) 3.8 (m, 2H) 4.7 (s, 1H) 7.1 (m, 4H).

Example 33 tert-butyl {1-[2-(1,3-dioxolan-2-yl)ethyl]-1,2,3,4-tetrahydro-1-naphthalenyl}methyl(methyl)carbamate

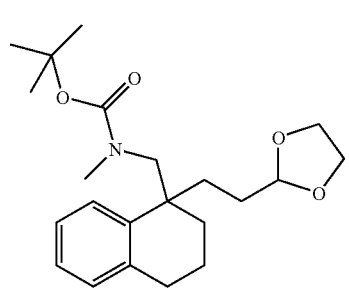

Utilizing the procedure from Example 28 and the product obtained in Example 26, tert-butyl {1-[2-(1,3-dioxolan-2-yl)ethyl]-1,2,3,4-tetrahydro-1-naphthalenyl}methyl(methyl)carbamate was afforded.

1H NMR (300 MHz, CHLOROFORM-D) δ ppm 1.3 (m, 1H) 1.5 (m, 9H) 1.8 (m, 9H) 2.7 (d, J=17.9 Hz, 3H) 3.3 (s, 1H) 3.8 (m, 1H) 3.9 (m, 4H) 4.8 (t, J=4.6 Hz, 1H) 7.2 (m, 4H).

Example 34 tert-butyl {5-chloro-1-[2-(1,3-dioxolan-2-yl)ethyl]-2,3-dihydro-1H-inden-1-yl}methyl(methyl)carbamate

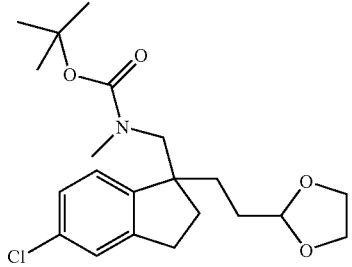

Utilizing the procedure from Example 28 and the product obtained in Example 27, tert-butyl {5-chloro-1-[2-(1,3-dioxolan-2-yl)ethyl]-2,3-dihydro-1H-inden-1-yl}methyl(methyl)carbamate was afforded in quantity yield.

1H NMR (400 MHz, DMSO-D6) δ ppm 1.3 (m, 10H) 1.5 (m, J=33.3 Hz, 1H) 1.7 (m, 2H) 1.8 (s, 1H) 2.0 (s, 1H) 2.5 (m, 3H) 2.8 (m, J=6.6 Hz, 2H) 3.1 (m, J=6.2 Hz, 1H) 3.6 (m, 1H) 3.7 (d, J=19.0 Hz, 2H) 3.8 (m, 2H) 4.7 (s, 1H) 7.2 (m, 3H).

Example 35 tert-butyl methyl{[1-(2-oxoethyl)-2,3-dihydro-1H-inden-1-yl]methyl}carbamate (Intermediate Example A)

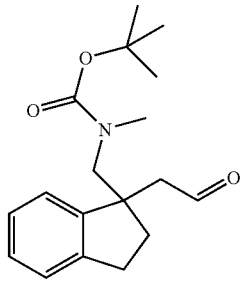

An acetone solution of tert-butyl [1-(1,3-dioxolan-2-ylmethyl)-2,3-dihydro-1H-inden-1-yl]methyl(methyl)carbamate (14.33 g, 41.24 mmole), para-toluene sulfonic acid (1 equivalent) and 50 ml of water were stirred overnight at room temperature. Evaporation of the acetone resulted in an oily slurry. Ether was added and washed with water, followed by NaHCO$_3$ sat. and dried over MgSO$_4$. Evaporation of the ether followed by flash chromatography on silica with 15% EtOAc and hexanes afforded 6.9383 g of tert-butyl methyl{[1-(2-oxoethyl)-2,3-dihydro-1H-inden-1-yl]methyl}carbamate as an oil.

1H NMR (400 MHz, CHLOROFORM-D) δ ppm 1.4 (m, 9H) 2.0 (m, J=16.2 Hz, 1H) 2.3 (m, 1H) 2.5 (m, J=17.8 Hz, 3H) 2.7 (m, 1H) 2.8 (m, 1H) 2.9 (m, 2H) 3.0 (m, 1H) 3.3 (d, J=14.3 Hz, 1H) 7.2 (m, 4H) 9.6 (s, 1H).

Example 36 tert-butyl methyl{[7-(2-oxoethyl)bicyclo[4.2.0]octa-1,3,5-trien-7-yl]methyl}carbamate

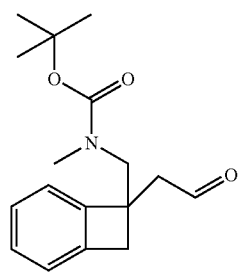

Utilizing the procedure from above Example 35 (Intermediate Example A) and the product obtained in Example 29, tert-butyl methyl{[7-(2-oxoethyl)bicyclo[4.2.0]octa-1,3,5-trien-7-yl]methyl}carbamate was afforded in 47% yield.

1H NMR (400 MHz, DMSO-D6) δ ppm 1.4 (m, 9H) 2.7 (m, 3H) 2.8 (m, 1H) 3.0 (m, 1H) 3.2 (d, J=14.3 Hz, 1H) 3.6 (m, 3H) 7.1 (m, 4H) 9.6 (m, J=6.8 Hz, 1H).

Example 37 tert-butyl methyl{[1-(2-oxoethyl)-1,2,3,4-tetrahydro-1-naphthalenyl]methyl}carbamate

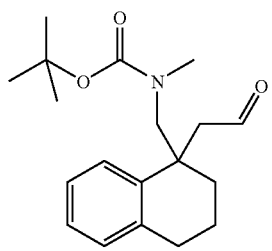

Utilizing the procedure from above Example 35 (Intermediate Example A) and the product obtained in Example 30, tert-butyl methyl{[1-(2-oxoethyl)-1,2,3,4-tetrahydro-1-naphthalenyl]methyl}carbamate was afforded.

$^1$H-NMR (300 MHz, CDCl$_3$) δ 9.43 (br s, 1H), 7.38-7.10 (m, 4H), 3.78-3.62 (m, 1H), 3.33-3.29 (m, 1H), 3.05-3.01 (m, 1H), 2.80-2.74 (m, 2H), 2.79 (br s, 3H), 2.61-2.54 (m, 1H), 2.05-2.02 (m, 1H), 1.89-1.79 (m, 3H), 1.41 (s, 9H). ES-LCMS m/z 340 (M+Na)$^+$.

Example 38 tert-butyl methyl{[1-(3-oxopropyl)-2,3-dihydro-1H-inden-1-yl]methyl}carbamate

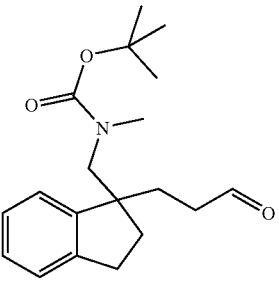

Utilizing the procedure from Example 35 (Intermediate Example A) and the product obtained in Example 31, tert-butyl methyl{[1-(3-oxopropyl)-2,3-dihydro-1H-inden-1-yl]methyl}carbamate was afforded in 48% yield.

1H NMR (400 MHz, CHLOROFORM-D) δ ppm 1.4 (m, 9H) 1.9 (m, 3H) 2.1 (m, J=28.1 Hz, 2H) 2.4 (m, 4H) 2.8 (m, 2H) 3.1 (t, J=13.3 Hz, 1H) 3.7 (dd, J=51.8, 14.2 Hz, 1H) 7.1 (m, 4H) 9.7 (s, 1H).

Example 39 tert-butyl methyl{[7-(3-oxopropyl)bicyclo[4.2.0]octa-1,3,5-trien-7-yl]methyl}carbamate

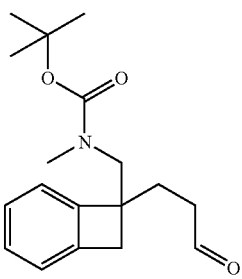

Utilizing the procedure from Example 35 (Intermediate Example A) and the product obtained in Example 32, tert-butyl methyl{[7-(3-oxopropyl)bicyclo[4.2.0]octa-1,3,5-trien-7-yl]methyl}carbamate was afforded in 19% yield.

1H NMR (400 MHz, DMSO-D6) δ ppm 1.3 (m, 9H) 2.0 (s, 2H) 2.5 (m, 2H) 2.7 (s, 3H) 2.9 (m, 1H) 3.1 (m, 1H) 3.4 (m, 1H) 3.6 (m, 1H) 7.1 (m, 4H) 9.6 (s, 1H).

Example 40 tert-butyl methyl{[1-(3-oxopropyl)-1,2,3,4-tetrahydro-1-naphthalenyl]methyl}carbamate

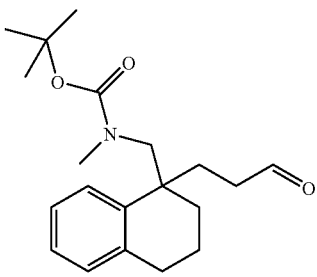

Utilizing the procedure from Example 35 (Intermediate Example A) and the product obtained in Example 33, tert-butyl methyl{[1-(3-oxopropyl)-1,2,3,4-tetrahydro-1-naphthalenyl]methyl}carbamate was afforded.

1H NMR (400 MHz, CHLOROFORM-D) δ ppm 1.4 (s, 9H) 1.6 (m, 2H) 1.8 (m, 4H) 2.2 (m, 3H) 2.7 (m, 4H) 3.3 (m, 1H) 3.6 (m, 1H) 7.1 (m, 4H) 9.7 (s, 1H).

Example 41 tert-butyl [5-chloro-1-(3-oxopropyl)-2,3-dihydro-1H-inden-1-yl]methyl(methyl)carbamate

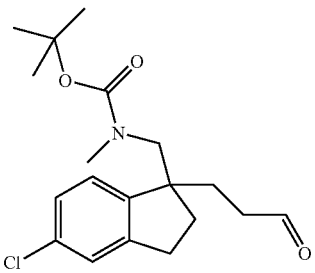

Utilizing the procedure from Example 35 (Intermediate Example A) and the product obtained in Example 34, tert-butyl [5-chloro-1-(3-oxopropyl)-2,3-dihydro-1H-inden-1-yl]methyl(methyl)carbamate was afforded.

1H NMR (400 MHz, DMSO-D6) δ ppm 1.3 (d, J=33.3 Hz, 9H) 1.6 (m, 3H) 2.1 (m, 2H) 2.5 (m, 3H) 2.8 (m, J=6.9, 6.9 Hz, 2H) 3.1 (m, J=14.3 Hz, 1H) 3.7 (m, 2H) 7.2 (m, 3H) 9.6 (s, 1H).

Example 42 tert-butyl methyl[(1-{2-[(1R,5S)-3-(2-methyl-1H-benzimidazol-1-yl)-8-azabicyclo[3.2.1]oct-8-yl]ethyl}-2,3-dihydro-1H-inden-1-yl)methyl]carbamate

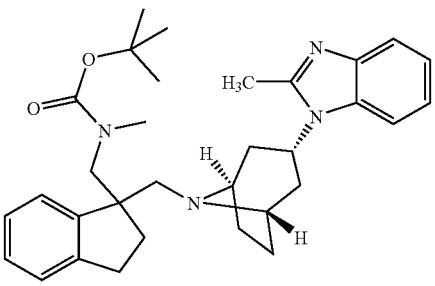

tert-butyl methyl{[1-(2-oxoethyl)-2,3-dihydro-1H-inden-1-yl]methyl}carbamate (600 mg, 1.98 mmole) and 1-[(1R,5S)-8-azabicyclo[3.2.1]oct-3-yl]-2-methyl-1H-benzimidazole (622 mg, 1.98 mmole) was dissolved in 50 ml of DCE to which was added sodium triacetoxyborohydride (839 mg, 3.96 mmole) which was stirred overnight. A saturated solution of NaHCO3 was added to quench the remaining hydride. The organic layer was washed with water and evaporated. The resulting residue was absorbed into silica gel and 100% EtOAc was use to remove impurities followed by Methanol to remove the product affording 0.7425 g of tert-butyl methyl [(1-{2-[(1R,5S)-3-(2-methyl-1H-benzimidazol-1-yl)-8-azabicyclo[3.2.1]oct-8-yl]ethyl}-2,3-dihydro-1H-inden-1-yl)methyl]carbamate (70% yield).

MS ES+ 529 (M+H), 1H NMR (300 MHz, CHLOROFORM-D) δ ppm 0.5-2.7 (m, 20H) 2.7-3.5 (m, 4H) 3.8 (m, 2H) 4.7 (m, 2H) 7.2 (m, 8H).

Example 43

N-methyl(1-{2-[(1R,5S)-3-(2-methyl-1H-benzimidazol-1-yl)-8-azabicyclo[3.2.1]oct-8-yl]ethyl}-2,3-dihydro-1H-inden-1-yl)methanamine

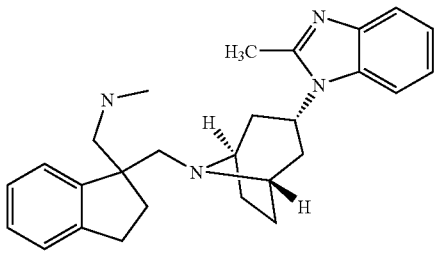

tert-butyl methyl[(1-{2-[(1R,5S)-3-(2-methyl-1H-benzimidazol-1-yl)-8-azabicyclo[3.2.1]oct-8-yl]ethyl}-2,3-dihydro-1H-inden-1-yl)methyl]carbamate (0.7425 g, 1.404 mmole) was dissolved in 2 ml of DCM and 2 ml of 4M HCl in dioxane. After stirring the reaction was neutralized with saturated NaHCO3 and extracted with Et₂O to afford N-methyl (1-{2-[(1R,5S)-3-(2-methyl-1H-benzimidazol-1-yl)-8-azabicyclo[3.2.1]oct-8-yl]ethyl}-2,3-dihydro-1H-inden-1-yl)methanamine (0.21 g, 35% yield).

MS ES+ 429 (M+H)

Example 44

2-chloro-N-methyl-N-[(1-{2-[(1R,5S)-3-(2-methyl-1H-benzimidazol-1-yl)-8-azabicyclo[3.2.1]oct-8-yl]ethyl}-2,3-dihydro-1H-inden-1-yl)methyl]benzenesulfonamide

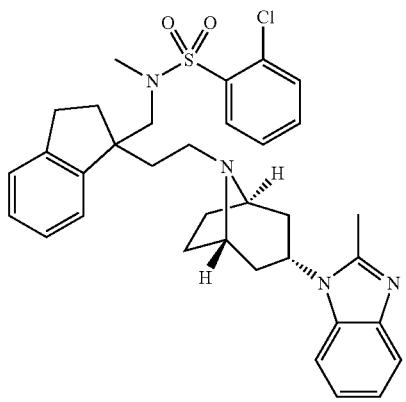

2-chlorophenylsulphonyl chloride (34.5 mg, 0.163 mmole) in 1 ml DCE was added to a solution of U19206/1/5 (70.0 mg, 0.163 mmole) in 1 ml of DCE and diisopropylethylamine (42.2 mg, 0.327 mmole) in 1 ml DCE. The reaction was shaken overnight followed by washing with saturated NaHCO₃ and separated using hydrophobic a frit and the organic evaporated. The residue was absorbed on silica and flashed using 0 to 10% MeOH in EtOAc to afford 2-chloro-N-methyl-N-[(1-{2-[(1R,5S)-3-(2-methyl-1H-benzimidazol-1-yl)-8-azabicyclo[3.2.1]oct-8-yl]ethyl}-2,3-dihydro-1H-inden-1-yl)methyl]benzenesulfonamide.

MS ES+ 603 (M+H), 1H NMR (400 MHz, CHLOROFORM-D) δ ppm 1.6 (m, 2H) 2.0 (s, 4H) 2.1 (m, 4H) 2.2 (m, 1H) 2.2 (s, 3H) 2.4 (m, 3H) 2.6 (d, J=4.4 Hz, 3H) 2.9 (m, 1H) 3.1 (m, 1H) 3.3 (d, J=14.5 Hz, 1H) 3.4 (s, 2H) 3.9 (m, J=14.5 Hz, 1H) 4.7 (m, 1H) 7.2 (m, 6H) 7.3 (m, 1H) 7.4 (m, 1H) 7.5 (td, J=7.5, 1.6 Hz, 1H) 7.5 (m, 1H) 7.7 (m, 1H) 8.0 (dd, J=7.9, 1.5 Hz, 1H).

Example 45

2-chloro-N-methyl-N-[((1S)-1-{2-[(1R,5S)-3-(2-methyl-1H-benzimidazol-1-yl)-8-azabicyclo[3.2.1]oct-8-yl]ethyl}-2,3-dihydro-1H-inden-1-yl)methyl]benzenesulfonamide

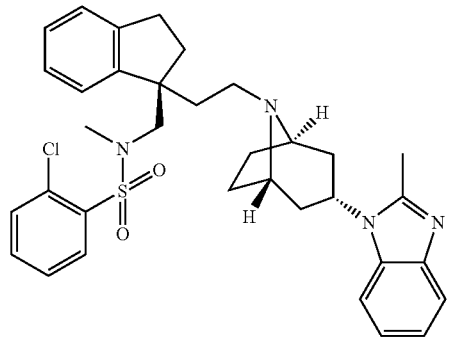

2-chloro-N-methyl-N-[(1-{2-[(1R,5S)-3-(2-methyl-1H-benzimidazol-1-yl)-8-azabicyclo[3.2.1]oct-8-yl]ethyl}-2,3-dihydro-1H-inden-1-yl)methyl]benzenesulfonamide (13 mg) was separated into its enantiomers using chiral SFC. The column was a Chiralcel OJ, 10 micron, using a mobile phase consisting of 93% CO2:7% Methanol (0.2% DEA).

Absolute configuration was determined by AB initio Vibration Circular Dichroism RT 22.642 min 100%.

Example 46

2-chloro-N-methyl-N-[((1R)-1-{2-[(1R,5S)-3-(2-methyl-1H-benzimidazol-1-yl)-8-azabicyclo[3.2.1]oct-8-yl]ethyl}-2,3-dihydro-1H-inden-1-yl)methyl]benzenesulfonamide

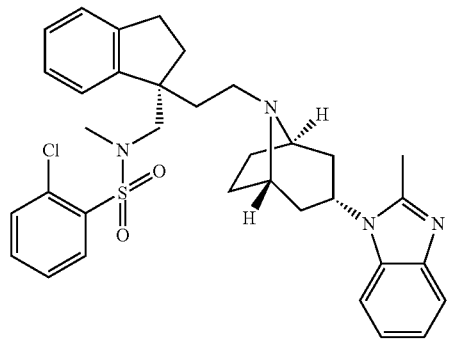

Prepared as in above Example 45, absolute configuration was determined by AB inito Vibration Circular Dichroism RT 25.839 min 100%.

Array Synthesis 2 ml of aldehydes made in Examples 36, 39, 40, and 41 (0.100 mmole/ml) were each pipetted out into 5 test tubes followed by 2 ml of amines 1-(3-methoxyphenyl)-1,3,8-triazaspiro[4.5]decan-4-one, 4-(3-benzyl-1,2,4-oxadiazol-5-yl)piperidine, 1-[3-(trifluoromethyl)phenyl]-1,3,8-triazaspiro[4.5]decan-4-one, 4-phenyl-1,4,8-triazaspiro[4.5]decan-2-one acetic acid salt, and benzyl ethyl(4-piperidinyl)carbamate (0.1005 mmole/ml), each illustrated below, were added to the five tubes for a total of 25 reactions.

1-(3-methoxyphenyl)-1,3,8-triazaspiro[4.5]decan-4-one

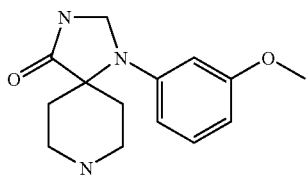

4-(3-benzyl-1,2,4-oxadiazol-5-yl)piperidine

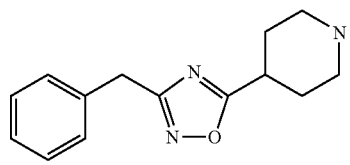

1-[3-(trifluoromethyl)phenyl]-1,3,8-triazaspiro[4.5]decan-4-one

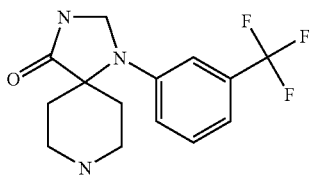

4-phenyl-1,4,8-triazaspiro[4.5]decan-2-one acetic acid salt

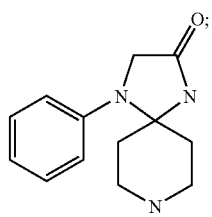

and
benzyl ethyl(4-piperidinyl)carbamate

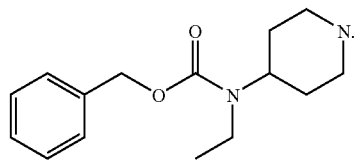

Sodium triacetoxyborohydride (0.600 mmole) was added to each tube and stirred overnight. 2 ml of saturated NaHCO$_3$ was added to each reaction and stirred, followed by separation through hydrophobic frits and evaporated to oils. 2 ml of a 50% solution of TFA in DCM was added to each tube and shaken for 30 min, and evaporated to oils. 2 ml of saturated NaHCO$_3$ was added to each tube and stirred. The aqueous bicarbonate was washed with DCE and separated using hydrophobic frits. The organic was evaporated and re-dissolved in DCE. The resulting solution was divided into two Bohdan MiniBlocks with 3 equivalents of PS-DIEA, followed by the addition of 1 ml of furoyl chloride (0.300 mmole/ml) to one block and 1 ml of benzenesulfonyl chloride (0.300 mmole/ml) to the second. After shaking overnight 4 equivalents of PS-Trisamine were added as a scavenger and shaken for an additional 6 hours. The products were filtered into 2-48 well plates and evaporated to thick oils, which were purified by Prep HPLC-MS.

For example, the following compound:

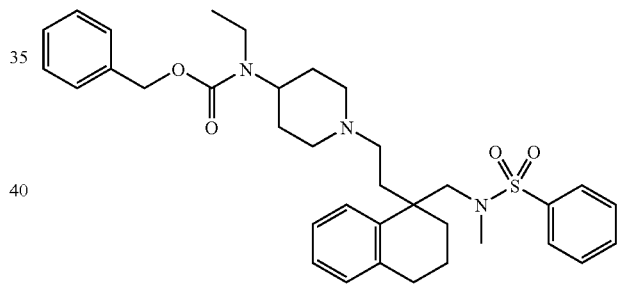

was characterized as
$^1$H NMR (400 MHz, CHLOROFORM-D) δ ppm 1.0 (m, 3H) 1.7 (s, 8H) 1.9 (m, 3H) 2.1 (m, 2H) 2.3 (s, 3H) 2.6 (m, 3H) 2.8 (m, 2H) 3.0 (d, J=14.0 Hz, 1H) 3.1 (m, 3H) 3.9 (m, 1H) 5.0 (s, 2H) 7.0 (m, J=6.4 Hz, 3H) 7.1 (m, 1H) 7.2 (m, 5H) 7.4 (m, 3H) 7.6 (m, 2H).

LAH=lithium aluminum hydride
DCE=dichloroethane
TFA=trifluoroacetic acid
LDA=lithium diisopropylamide
TEA=triethylamine
THF=tetrahydrofuran
DCM=dichloromethane
TLC=thin layer chromatography
DEA=diethylamine
LHMDS=lithium bis(trimethylsilyl)amide
NaHMDS=sodium bis(trimethylsilyl)amide
Boc Anhy=di-tert-butyl dicarbonate
PS-DIEA=polystyrene supported diisopropylethylamine
PS-Trisamine=polystyrene supported trisamine As will be appreciated by those skilled in the art, additional compounds of the present invention may be similarly prepared according to the schemes provided herein.

Biological Data

The following definitions apply:

| | |
|---|---|
| $IC_{50}$ | Concentration of compound that displaces 50% of radioligand |
| $pIC_{50}$ | The determined $IC_{50}$ value expressed as $-\log10(IC_{50})$ |

CC-Chemokine Receptor-5 Binding by Scintillation Proximity Assay (CCR5SPA)

Scintillation Proximity Assay for the Human CC-Chemokine Receptor, CCR-5

This protocol describes a high-throughput screen using SPA binding to identify compounds that inhibit binding of $^{125}$I-MIP1α to the human CCR5 chemokine receptor.

CCR5 is a G protein-coupled receptor that binds the natural chemokine ligands, MIP1α, MIP1β and RANTES. CCR5 acts as a co-receptor with CD4 for entry of HIV-1 into human T-cells and monocytes. Chemokines also play a role in acute and chronic inflammatory processes. Chemokines are soluble proteins produced and released by a wide variety of cell types during the initial phase of a host response to a forgein substance entering the body.

Human CCR5 receptors were expressed in Chinese Hamster Ovary (CHO) cells, registration #12025. Cells were grown in suspension and a 50 to 80 ml CCR5 cell pellet was prepared. Membrane preparation: 1) Weigh pellet; 2) Prepare an ice-cold 50 mM HEPES buffer, containing 0.0025 mg/ml Pefabloc, 0.0001 mg/ml Pepstatin A, 0.0001 mg/ml Leupeptin, 0.0001 mg/ml Aprotinin (protease inhibitor cocktail), pH 7.4; 3) Homogenize pellet in 5 volumes of HEPES buffer; 4) Homogenize again with a glass homogenizer 10 to 20 strokes; 5) Centrifuge homogenate at 18,000 rpm in a F28/36 rotor using a Sorvall RC26 PlUS refrigerated Centrifuge for 30 minutes; 6) Discard supernatant and resuspend pellet in 3 volumes of HEPES buffer; 7) Homogenize and centrifuge again using steps 4-6, 2 more times; 8) Reweigh pellet and homogenize in 3× weight-to-volume of HEPES buffer; 9) Aliquot 0.5 to 1.5 ml of the membrane preparation into small vials and store at −80 degrees Centigrade; 10) Determine the protein concentration of the membrane preparation using the Bio-Rad or BCA method; 11) The membrane homogenate will need to be characterized for the assay conditions a.) Protein concentration; b.) Optimal protein-to-bead ratio in SPA; and c.) Saturation curve to determine Kd and Bmax in SPA.

The saturation curve binding experiment is performed by adding varying amounts of $[^{125}I]$MIP1α (0-8.5 nM to membranes and beads in concentrations chosen from the optimal protein/bead ratio. The data is analyzed using a non-linear curve-fitting program. The $K_d$ and Bmax are derived from the curve.

Bacitracin 50 mg/ml is dissolved in deionized water, brought to a boil for 5 minutes (to destroy protease activity) and cooled. Prepared 1 ml aliquots and store at −80° C.

Protease inhibitor cocktail is prepared by dissolving 25 mg/ml of Pefabloc, 1 mg/ml of Leupeptin, 1 mg/ml of Aprotinin and 1 mg/ml of Pepstatin A in 100% DMSO. The cocktail can be aliquoted and stored frozen at −20° C. until needed.

Sigmacote: Any reagent bottles and reservoirs that come in contact with the radioligand are treated with Sigmacote to reduce sticking. Rinse containers with undiluted Sigmacote; rinse with deionized water several times, and allow to air dry before using.

Color Quench Assay-$[^{125}I]$ SPA PVT color quench kit, Cat. No. RPAQ 4030, Amersham Ltd. A color quench curve is generated for each Packard TopCount and is stored in each counting protocol specific for the assay. This is done to prevent colored compounds from quenching the scintillation counts.

Compounds Preparation:

Compounds for a single concentration determination (One Shots) are delivered in 96 well Packard Optiplates containing 1 μl of compound in 100% DMSO in columns A1-H10 (80 compounds/plate). Column A11 to H11 is used for total binding (Bo) (vehicle-5 μl of the appropriate DMSO concentration) and column A12 to D12 is used for determination of nonspecific binding. No further preparation is required.

Compounds for concentration-response curves (10 points) are delivered in 96-Packard Optiplates containing 1 μl of compound in 100% DMSO in columns A1-H10. A 10-point concentration-response curve is desired for each compound with a starting high concentration of 30 μM (in the assauy final). Column A11 to H11 is used for total binding (Bo) (vehicle-5 μl of the appropriate DMSO concentration) and column A12 to D12 is used for determination of nonspecific binding. No further preparation is required Materials:

1 M HEPES, pH 7.4, Gibco, Cat. No. 15360-080

Bacitracin, Sigma Catalog. Number. B-0125

Bovine Serum Albumin, Sigma, Cat. No. A-7888

$MgCl_2$, J. T. Baker 2444-01

$CaCl_2$, Sigma, Cat. No. C5080

MIP1α, Peprotech, Cat. No. 300-08

Sigmacote, Sigma, Cat. No. SL2

Scintillation Proximity Beads, Wheat Germ Agglutinin, Amersham, Cat No. RPNQ 0001

$[^{125}I]$MIP1α, NEN (#NEX298)

Packard 96 well flat-bottom Optiplate, Cat. No. 6005190

Falcon 96 well round-bottom plate, Cat. No. 3077

TOPSEAL-S, Packard, Cat. No. 6005161

Dimethyl Sulfoxide, EM Science, Cat. No. MX1458-6

Siliconized Pipette tips, Accutip, volume 200-1300 uL, Cat. No. P5048-85

Siliconized Pipette tips, Bio Plas, Inc., volume 1-200 uL, Cat. No. 60828-908

Reagent Reservoir, Elkay, Cat. No. 175-RBAS-000

Assay Buffer Preparation:

50 mM HEPES buffer pH 7.4, 1 mM $CaCl_2$, 5 mM MgCl2 (this can be made ahead as a 100× stock),1% BSA, 0.5 mg/ml Bacitracin, Protease inhibitor Cocktail (see preparation above) 100 uL/100 ml, DMSO is added to equal a final concentration of 2% per well (includes compound % DMSO) if needed.

Experimental Details:

$[^{125}I]$MIP1α Preparation:

Prepared radioligand dilutions in container treated with Sigmacote

Reconstitute each 50 μCi vial with 0.5 ml of deionized water and store at 4° C.

Specific Activity=2,000 Ci/mmol

Add ~60,000 cpm (0.17 nM) to each assay well in 50 uL.

Bo (Control Binding):

Make a 20% DMSO solution and add 5 uls of this to each well in col A11-H11. This gives a final 2% DMSO concentration for the well when added to the 1% in the assay buffer.

NSB (Non-Specific Binding):

Make a stock dilution of MIP1α at 100 uM using deionized water; aliquot and freeze. Dilute the MIP-1α stock solution to a concentration of 2 μM in the same 20% DMSO solution used above and add 5 μl to the wells in column A12 to D12 to give a final assay concentration of 100 nM. Prepare this in a Sigmacote-treated container.

Membrane and SPA Bead Preparation—

The final assay concentration for the membrane is 15 μg per well. SPA beads are prepared by adding 5 ml of assay buffer to a 500 mg vial. The final concentration of SPA beads in the assay is 0.25 mg/well. Membranes and beads are premixed as a 1:1 (membrane:bead) mixture and maintained at mixture at 4° C. with constant stirring. 50 μl of the mixture is added to each assay well. After all reagents have been added to the plates (total assay volume 100 μl), shake plates for 4 hours at room temperature. After 4 hours, place the plates on the TopCount in a count the plates on the TopCount for 30 sec per well using an appropriate program (i.e., one with a quench curve established for the conditions of the assay.

Data Reduction:

Data reduction is performed using the Microsoft Excel Addins Robofit or Robosage.

For single concentration assays (One Shots), the result of each test well is expressed as % inhibition using the following formula: $100*(1-(U1-C2)/(C1-C2))$. Where U1 is the unknown sample in cpm observed in a particular well, C1 is the average of column 12 cpm observed in the absence of any added inhibitor, and C2 is the average of column 11 cpm observed in the presence of 1 μM of MIP1α.

For concentration-response assays, the result of each test well is expressed as % B/Bo (% total specific binding) using the following formula: $100*(U1-C2)/C1-C2)$. Curves were generated by plotting the % B/Bo versus the concentration and the $IC_{50}$ is derived using the equation $y=Vmax*(1-(x^n/(k^n+x^n)))$.

Controls and Standards:

Each plate contains 12 wells of total binding (column A11-H11). The cpm/well are averaged and are used in data reduction as value C1. Each plate also contains 4 wells of non-specific binding (wells A12-D12). The counts of these wells are averaged and used in data reduction as value C2.

A standards plate is included in each experiment. This plate contains a 14-point concentration-response curve (in triplicate) for the standard compound MIP1α at a starting concentration of 1 μM. The average historical $pK_i$ obtained with MIP1α is 7.6.

The relevant biological response field for a single concentration (One Shots) is % inhibition. Inhibition values of >40 or >50% were considered positive responses.

The relevant biological response field for a concentration-response experiment is $pK_I$ HOS Assay (Also Referred to as HOS-LTR-Luciferase Assay).

Materials

DMEM (GibcoBRL#10564-011)

Trpsin-EDTA (GibcoBRL #25300-054)

Heat inactivated Fetal Bovine Serum (FBS) (Hyclone # SH30070.03)

96-well, black-walled, clear-bottom, tissue culture-treated plates (Costar #3904)

96-well, clear-walled, clear-bottom tissue culture-treated plates (Costar #3598)

Phosphate Buffered Saline (PBS) (GibcoBRL #14190-144)

Dimethyl Sulfoxide (DMSO) (Sigma # D2650)

Luclite Luciferase Reporter assay (Packard #6016911)

HOS-CD4.CCR5-LTR-Luciferase (Bioresource Registration #21164): Human

Osteosarcoma cell line engineered to overexpress human CD4 and human CCR5 (AIDS Repository cat#3318) stably transfected with HIV-1-LTR-Luciferase reporter.

Advanced Preparation

Growth and Maintenance of the HOS-CD4.CCR5-LTR-Luciferase cell line:

The cells were propagated in DMEM containing 2% FBS. Cells were split by standard trypsinization when confluency reached 80% (roughly every 2 to 3 days).

Titering of Virus Stocks:

HIV-1 virus stocks were titered in the assay system in order to obtain an estimate of the number of infectious particles per unit volume (described as RLU/ml). Virus stocks were diluted into DMEM containing 2% FBS and assayed as described in the "procedure" section below.

Procedure

Black-walled 96-well tissue culture plates were seeded with HOS-CD4.CCR5-LTR-Luciferase @0.6 to $1.2×10^3$ cells per well in 50 ul DMEM containing 2% FBS and placed in a humidified incubator @37° C., 5% $CO_2$ overnight. The following day, test compounds were titrated 4-fold at 2× the final concentration in DMEM+2% FBS+0.2% DMSO. 50 μl of titrated compound was transferred to the HOS cells and the plates were placed in a humidified incubator at 37° C., 5% $CO_2$ for 1 hr. An additional 60 ul of 2× titrated compound was transferred to a clear-walled 96-well tissue culture plate and 60 ul of HIV (diluted to appropriate m.o.i.) was added to each well and thoroughly mixed. 100 ul of the HIV/compound mixture was transferred to the black-walled plates containing 100 ul of cells/compound. The plates were placed in a humidified incubator at 37° C., 5% $CO_2$ for 72 hr. Following the 72 hour incubation, 150 ul of supernatant was removed and 50 ul of reconstituted LUCLITE (kit reagent) was added to each well. Each plate was sealed and read in a Topcount (Packard) luminometer at 1 s/well.

Data Reduction

Relative Light Units (RLU) were expressed as % control (RLU at drug [ ]/RLU no drug)*100=% Control $IC_{50}$ values were determined by any one of the following four nonlinear regression models:

$$y=Vmax*(1-(x^n/(K^n+x^n)))+Y2$$

$$y=Vmax*(1-(x^n/(K^n+x^n)))$$

$$y=Vmax*(1-(x/(K+x)))+Y2$$

$$y=Vmax*(1-(x/(K+x)))$$

Where: K is $IC_{50}$, Y2 is baseline, and N is Hill Coefficient

Each of the compounds of the present invention provides a $pIC_{50}$ value of at least 5 when tested in each of the above-described assays.

Test compounds are employed in free or salt form.

Although specific embodiments of the present invention have been illustrated and described in detail, the invention is not limited thereto. The above detailed description of preferred embodiments is provided for example only and should not be construed as constituting any limitation of the invention. Modifications will be obvious to those skilled in the art, and all modifications that do not depart from the spirit of the invention are intended to be included within the scope of the appended claims.

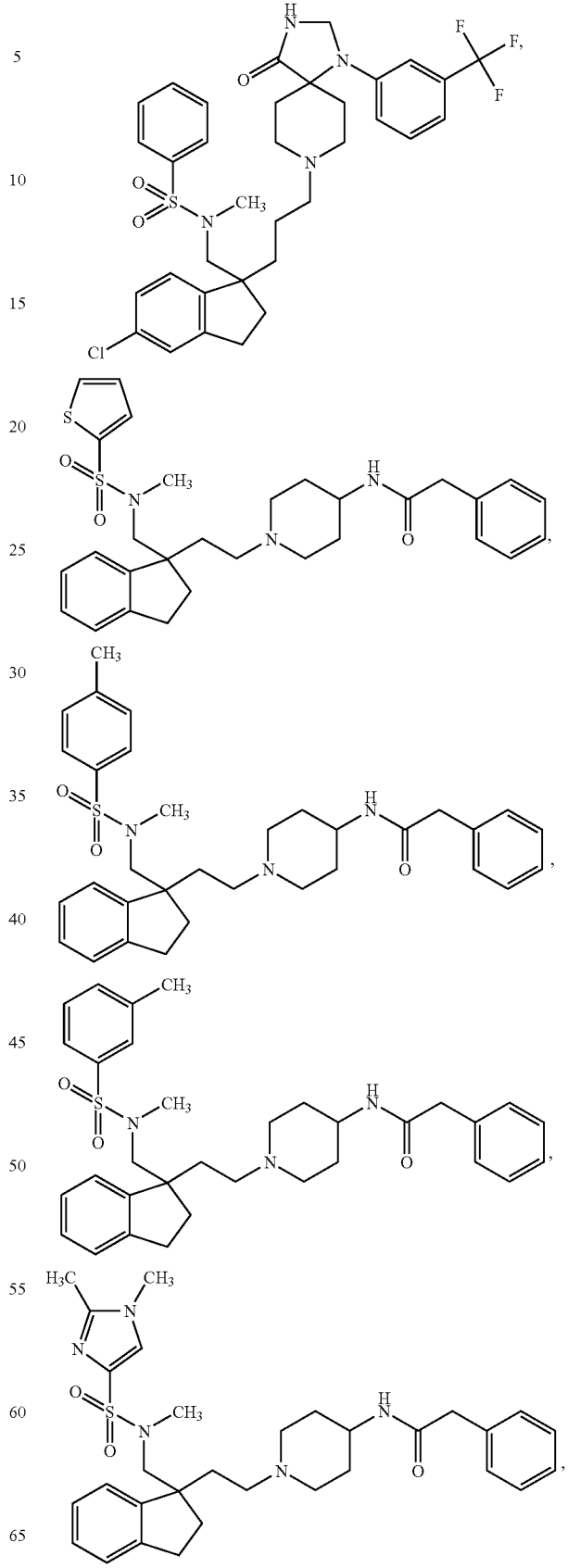

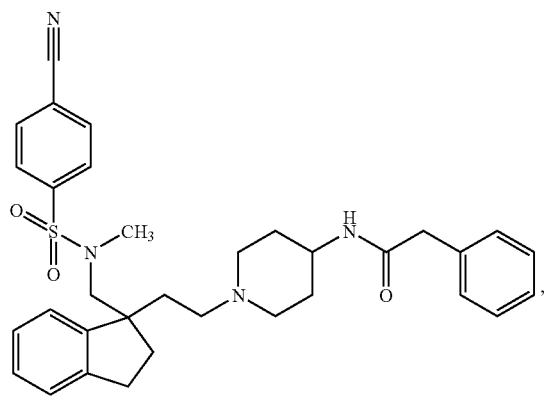
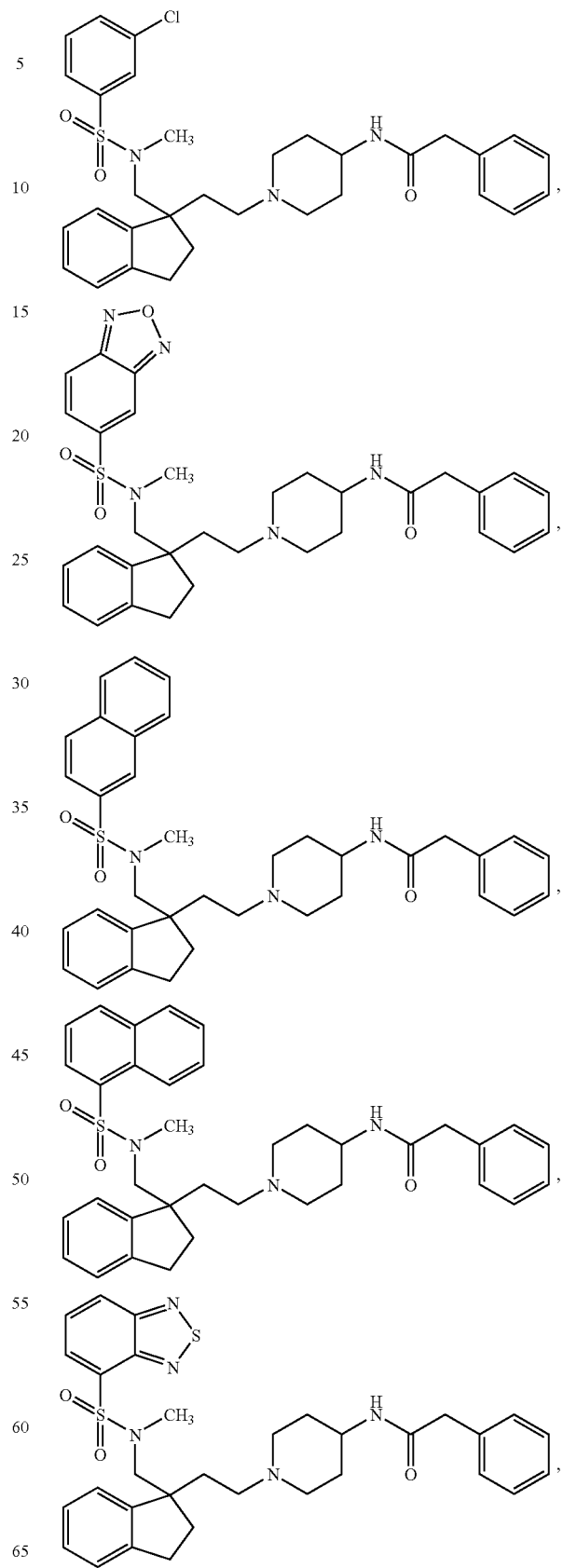

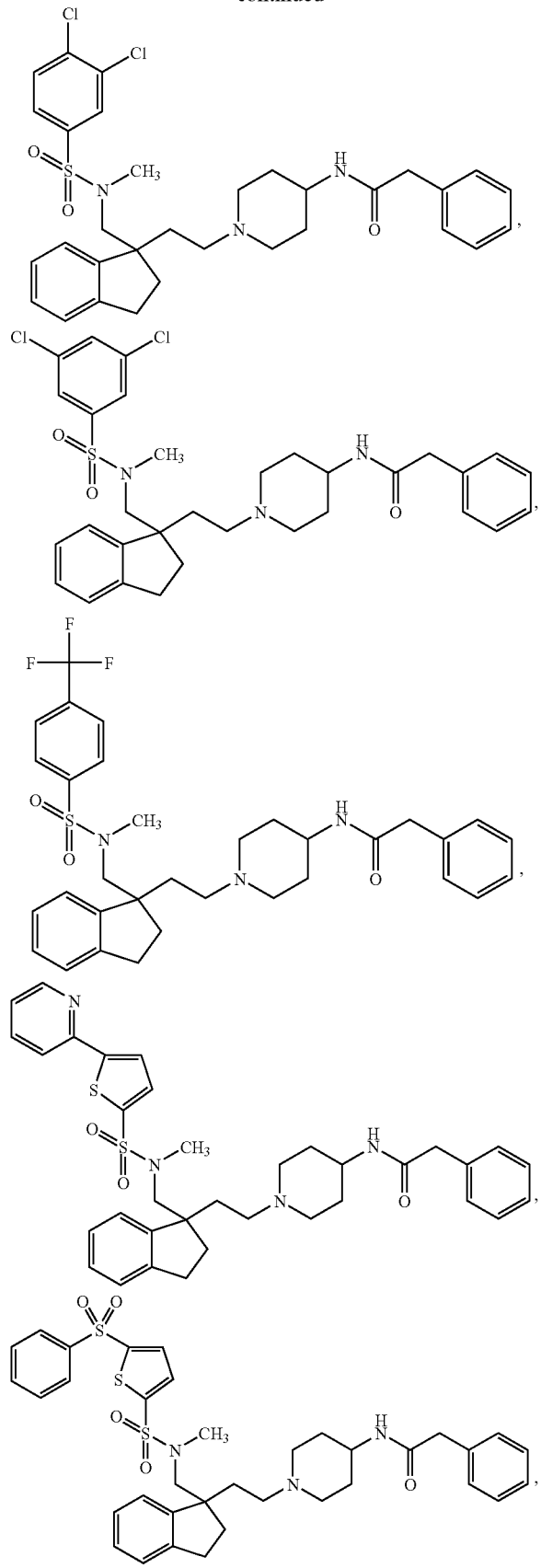
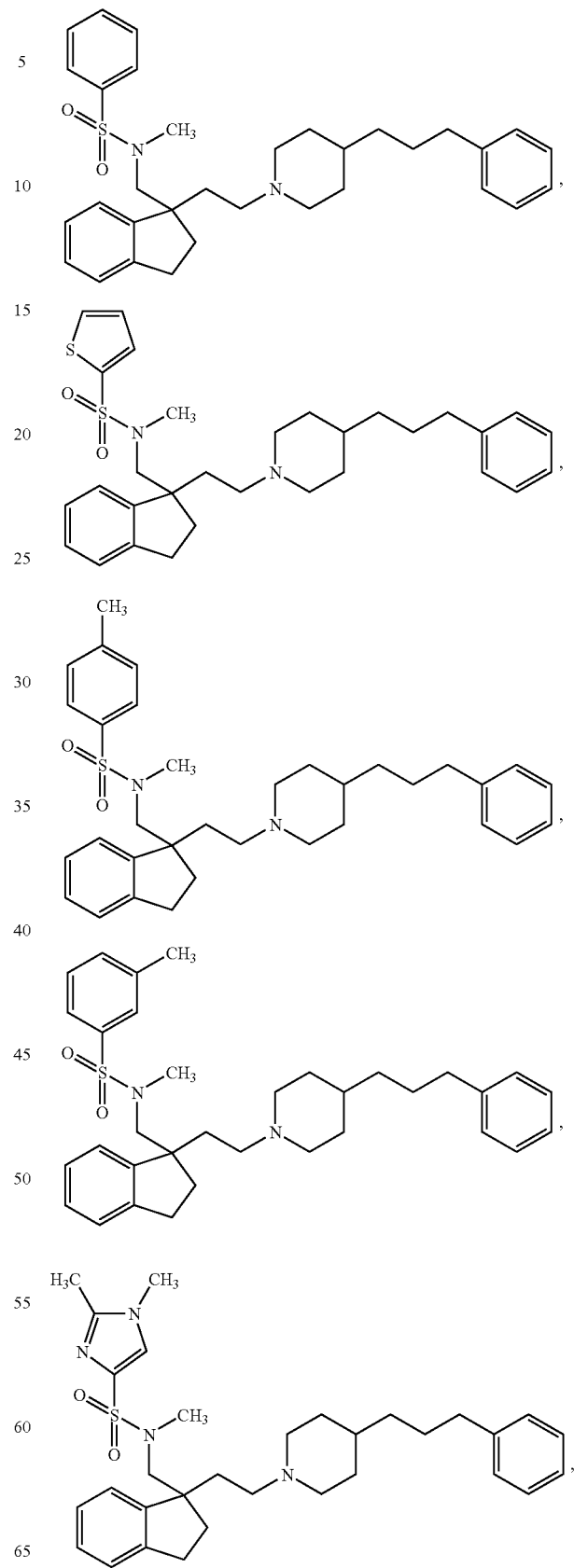

-continued
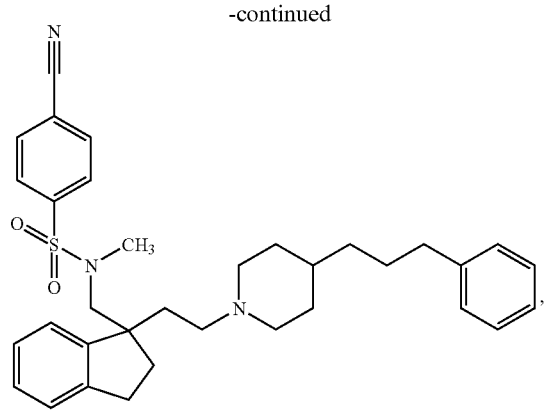
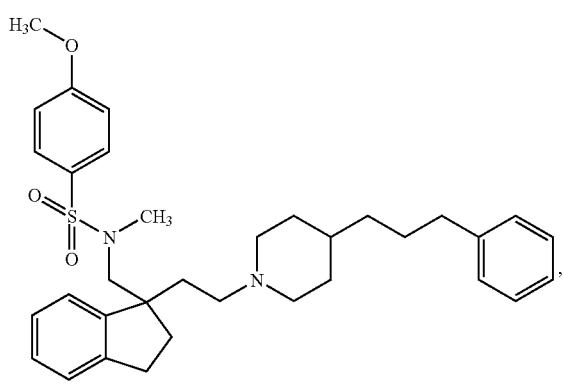
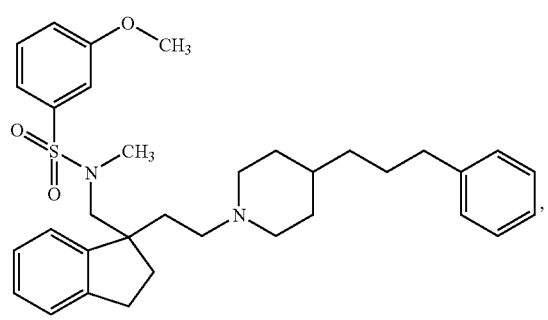
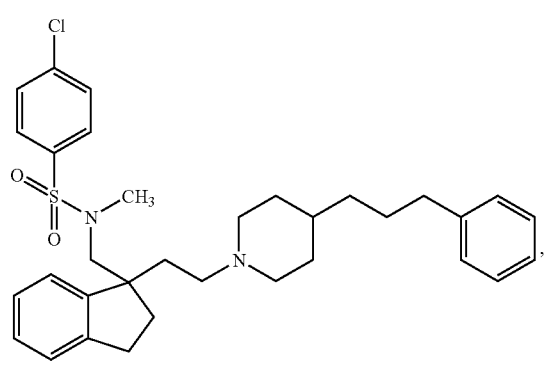
-continued
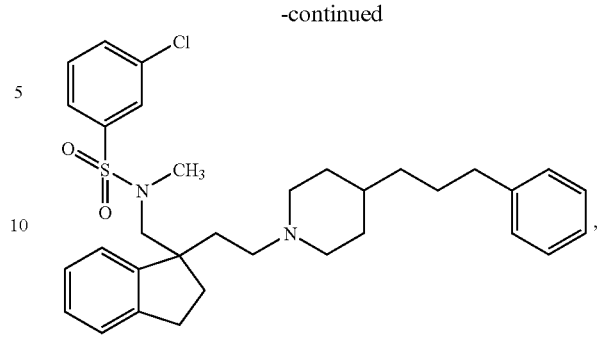
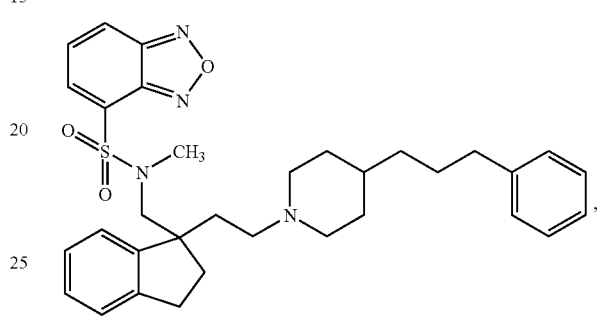
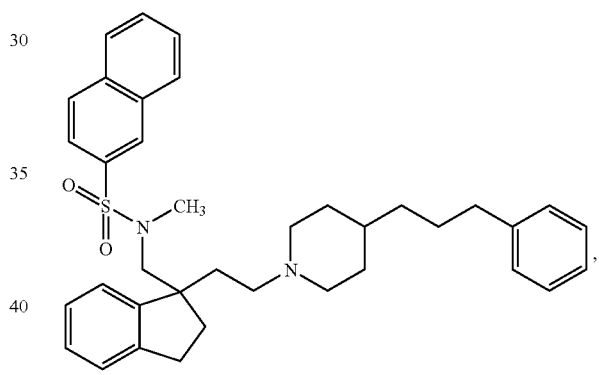
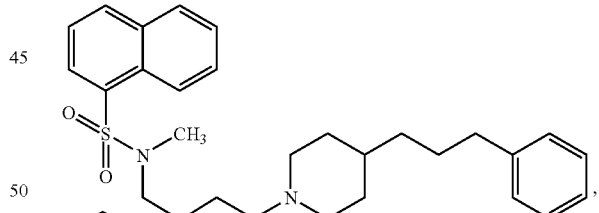
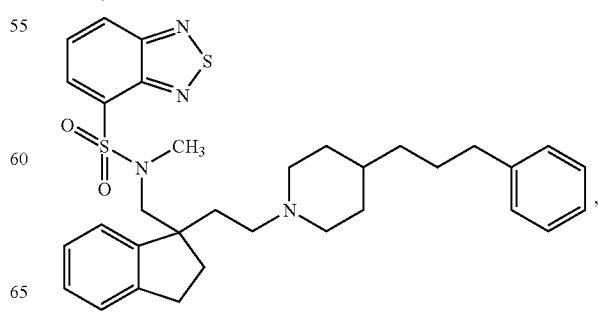

-continued
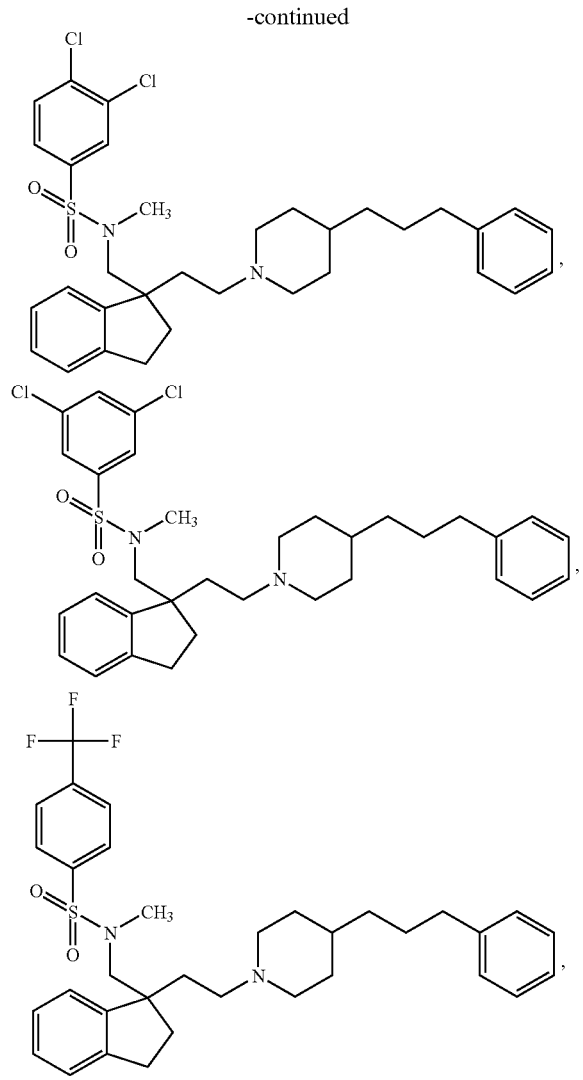
-continued
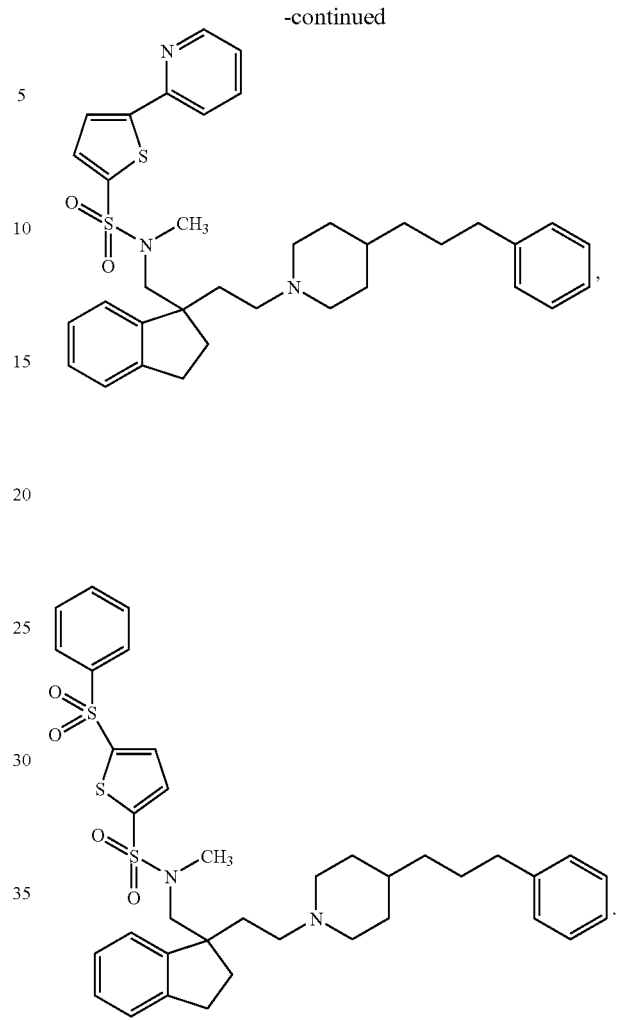

The invention claimed is:

1. A compound or salt thereof selected from the group consisting of

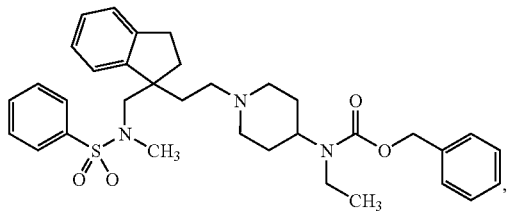,

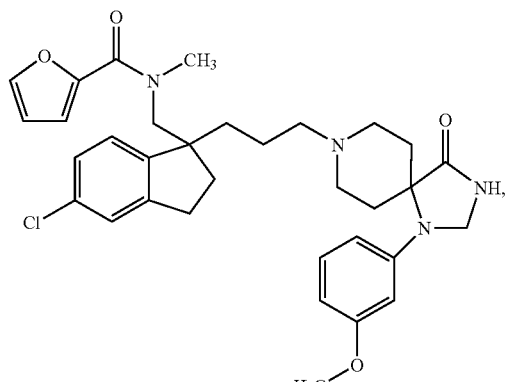,

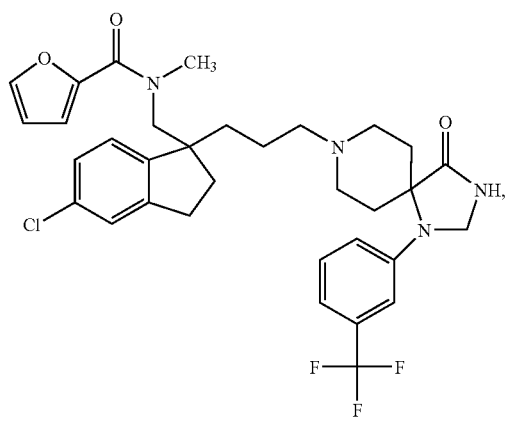,

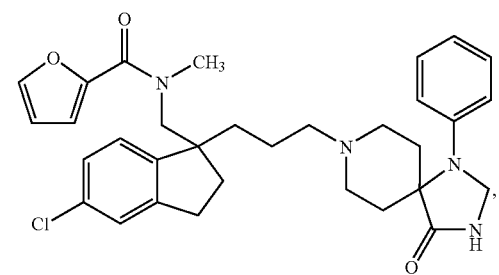,

-continued